US012746120B2

(12) United States Patent
Fung et al.

(10) Patent No.: US 12,746,120 B2
(45) Date of Patent: Sep. 29, 2026

(54) CONTROLLABLY DEPLOYABLE PROSTHETIC VALVE

(71) Applicant: Neovasc Inc., Toronto (CA)

(72) Inventors: Eric Soun-Sang Fung, Vancouver (CA); Kathleen Hung, New Westminster (CA); Karen Tsoek-Ji Wong, Richmond (CA); Aaron J. Chalekian, Savage, MN (US); Connor Lucas Haberl, Vancouver (CA); Anson Wai Chung Cheung, Vancouver (CA); Kellen Bodell, Plymouth, MN (US); Christopher Brodeur, Plymouth, MN (US)

(73) Assignee: NEOVASC INC., Ontario (CA)

( * ) Notice: Subject to any disclaimer, the term of this patent is extended or adjusted under 35 U.S.C. 154(b) by 585 days.

(21) Appl. No.: 18/166,945

(22) Filed: Feb. 9, 2023

(65) Prior Publication Data

US 2023/0255769 A1 Aug. 17, 2023

Related U.S. Application Data

(63) Continuation of application No. 16/837,884, filed on Apr. 1, 2020, now Pat. No. 11,602,429.

(Continued)

(51) Int. Cl.

| | |
|---|---|
| *A61F 2/24* | (2006.01) |
| *A61F 2/06* | (2013.01) |

(52) U.S. Cl.

CPC .......... *A61F 2/2436* (2013.01); *A61F 2/2418* (2013.01)

(58) Field of Classification Search

None

See application file for complete search history.

(56) References Cited

U.S. PATENT DOCUMENTS

| | | |
|---|---|---|
| 2,967,856 A | 1/1961 | Coover, Jr. et al. |
| 5,607,444 A | 3/1997 | Lam |

(Continued)

FOREIGN PATENT DOCUMENTS

| | | | |
|---|---|---|---|
| AU | 2020256195 B2 | 10/2022 | |
| CA | 2715195 A1 * | 9/2009 | ............ A61M 25/06 |

(Continued)

OTHER PUBLICATIONS

"Chinese Application Serial No. 202080033982.8, Office Action mailed Jul. 23, 2024", W English Translation, 7 pgs.

(Continued)

*Primary Examiner* — Ann Hu

(74) *Attorney, Agent, or Firm* — Morrison & Foerster LLP

(57) ABSTRACT

A prosthetic valve may be used to repair a diseased or otherwise damaged heart valve such as the mitral valve. The prosthetic valve may include atraumatic anchor tabs which may be radiopaque or echogenic. A cinching mechanism may also be coupled to the prosthetic valve to control radial expansion of the prosthetic valve. The cinching mechanism may include a wire lasso or a belt. The prosthetic valve may include an expandable frame which has a reduced number of strut connection nodes to allow a lower profile collapsed configuration and tighter crimping. The commissure posts of the prosthetic valve may extend beyond an edge of the ventricular skirt portion of the device.

18 Claims, 58 Drawing Sheets

Related U.S. Application Data

(60) Provisional application No. 62/827,380, filed on Apr. 1, 2019.

(56) References Cited

U.S. PATENT DOCUMENTS

| | | | | |
|---|---|---|---|---|
| 6,352,547 | B1 * | 3/2002 | Brown | B25B 27/146 606/1 |
| 7,381,219 | B2 * | 6/2008 | Salahieh | A61F 2/2418 623/2.11 |
| 8,216,256 | B2 * | 7/2012 | Raschdorf, Jr. | A61B 17/122 606/151 |
| 9,480,559 | B2 * | 11/2016 | Vidlund | C08L 67/04 |
| 9,597,183 | B2 * | 3/2017 | Quadri | A61F 2/2418 |
| 9,622,863 | B2 * | 4/2017 | Karapetian | A61F 2/246 |
| 9,655,722 | B2 | 5/2017 | Morriss et al. | |
| 10,117,741 | B2 * | 11/2018 | Schweich, Jr. | A61F 2/2409 |
| 10,363,130 | B2 * | 7/2019 | Armer | A61F 2/2409 |
| 10,376,364 | B2 * | 8/2019 | Tamir | A61F 2/2436 |
| 10,722,353 | B2 * | 7/2020 | Levi | A61F 2/2418 |
| 10,835,750 | B2 * | 11/2020 | Gross | A61N 1/37518 |
| 11,065,114 | B2 | 7/2021 | Raanani | |
| 11,202,704 | B2 * | 12/2021 | Morriss | A61F 2/2433 |
| 11,298,229 | B2 | 4/2022 | Khairkhahan | |
| 11,602,429 | B2 | 3/2023 | Fung et al. | |
| 12,310,575 | B2 * | 5/2025 | Hacohen | A61F 2/2436 |
| 12,350,152 | B2 * | 7/2025 | Alkhatib | A61F 2/2418 |
| 2001/0021872 | A1 | 9/2001 | Bailey et al. | |
| 2004/0181238 | A1 | 9/2004 | Zarbatany et al. | |
| 2009/0005863 | A1 | 1/2009 | Goetz et al. | |
| 2011/0004299 | A1 * | 1/2011 | Navia | A61F 2/2415 623/2.18 |
| 2014/0257467 | A1 | 9/2014 | Lane et al. | |
| 2015/0257878 | A1 | 9/2015 | Lane et al. | |
| 2015/0265400 | A1 | 9/2015 | Eidenschink et al. | |
| 2016/0074011 | A1 | 3/2016 | Johnson et al. | |
| 2016/0250050 | A1 * | 9/2016 | Lim | A61F 2/95 623/1.12 |
| 2017/0135816 | A1 * | 5/2017 | Lashinski | A61F 2/2466 |
| 2017/0325947 | A1 | 11/2017 | Eidenschink et al. | |
| 2018/0055628 | A1 * | 3/2018 | Patel | A61F 2/2409 |
| 2018/0055629 | A1 * | 3/2018 | Oba | A61F 2/2409 |
| 2018/0296338 | A1 | 10/2018 | Rabito et al. | |
| 2019/0029811 | A1 | 1/2019 | Bishop et al. | |
| 2019/0328515 | A1 | 10/2019 | Peterson et al. | |
| 2020/0297481 | A1 | 9/2020 | Oba et al. | |
| 2020/0306040 | A1 | 10/2020 | Fung et al. | |
| 2020/0306044 | A1 | 10/2020 | Ratz et al. | |
| 2021/0161637 | A1 | 6/2021 | Eigler et al. | |
| 2021/0220137 | A1 | 7/2021 | Noe | |

FOREIGN PATENT DOCUMENTS

| | | | | |
|---|---|---|---|---|
| CA | 2874219 | C | 7/2020 | |
| CA | 3135753 | | 10/2023 | |
| CN | 104203158 | | 12/2014 | |
| CN | 105263444 | | 1/2016 | |
| CN | 108348321 | | 7/2018 | |
| CN | 109419573 | A * | 3/2019 | A61F 2/2418 |
| CN | 113811265 | A | 12/2021 | |
| DE | 10103955 | B4 | 11/2001 | |
| DE | 10033858 | B4 | 1/2002 | |
| DE | 102005052628 | A1 | 5/2007 | |
| DE | 102006013113 | B4 | 12/2008 | |
| DE | 102008015781 | B4 | 9/2011 | |
| DE | 102010051632 | B4 | 9/2013 | |
| DE | 102005032974 | B4 | 11/2013 | |
| DE | 202013011734 | U1 | 4/2014 | |
| DE | 102005052628 | B4 | 6/2014 | |
| DE | 10301026 | B4 | 10/2014 | |
| DE | 212013000104 | U1 | 11/2014 | |
| DE | 102008012438 | B4 | 12/2014 | |
| DE | 102011107551 | B4 | 5/2015 | |
| DE | 102011054176 | B4 | 2/2016 | |
| DE | 102014114762 | B3 | 3/2016 | |
| DE | 102013208038 | B4 | 9/2016 | |
| DE | 102010012677 | B4 | 8/2017 | |
| DE | 202011110951 | U1 | 10/2017 | |
| DE | 202011110985 | U1 | 12/2017 | |
| DE | 202016105963 | U1 | 1/2018 | |
| DE | 10394350 | B4 | 5/2018 | |
| DE | 102009024648 | B4 | 5/2018 | |
| DE | 102015206098 | B4 | 9/2018 | |
| DE | 10065824 | B4 | 10/2018 | |
| DE | 202017104793 | U1 | 11/2018 | |
| DE | 102011106928 | B4 | 2/2019 | |
| DE | 202016008737 | U1 | 4/2019 | |
| DE | 102013205519 | B4 | 5/2019 | |
| DE | 102008014730 | B4 | 7/2019 | |
| DE | 102018102940 | B4 | 10/2019 | |
| DE | 102009009158 | B4 | 11/2020 | |
| EP | 1077072 | B1 | 11/2003 | |
| EP | 1140244 | B1 | 11/2003 | |
| EP | 1214106 | B1 | 11/2003 | |
| EP | 1143864 | B1 | 2/2004 | |
| EP | 1220651 | B1 | 3/2004 | |
| EP | 1265534 | B1 | 6/2004 | |
| EP | 1347785 | B1 | 7/2004 | |
| EP | 1245202 | B1 | 8/2004 | |
| EP | 1161204 | B1 | 9/2004 | |
| EP | 1266641 | B1 | 10/2004 | |
| EP | 1102567 | B1 | 11/2004 | |
| EP | 1117446 | B1 | 11/2004 | |
| EP | 1107710 | B1 | 12/2004 | |
| EP | 1121070 | B1 | 12/2004 | |
| EP | 1217966 | B1 | 12/2004 | |
| EP | 1233731 | B1 | 12/2004 | |
| EP | 1294318 | B1 | 12/2004 | |
| EP | 1237510 | B1 | 1/2005 | |
| EP | 1034753 | B1 | 2/2005 | |
| EP | 1259194 | B1 | 2/2005 | |
| EP | 1121069 | B1 | 3/2005 | |
| EP | 1143879 | B1 | 3/2005 | |
| EP | 1023879 | B1 | 4/2005 | |
| EP | 1339356 | B1 | 4/2005 | |
| EP | 1214022 | B1 | 5/2005 | |
| EP | 1318774 | B1 | 5/2005 | |
| EP | 1088529 | B1 | 6/2005 | |
| EP | 1171060 | B1 | 6/2005 | |
| EP | 1251803 | B1 | 6/2005 | |
| EP | 1259776 | B1 | 6/2005 | |
| EP | 1272123 | B1 | 6/2005 | |
| EP | 1049422 | B1 | 7/2005 | |
| EP | 1230901 | B1 | 8/2005 | |
| EP | 1335683 | B1 | 8/2005 | |
| EP | 1307246 | B1 | 9/2005 | |
| EP | 1267753 | B1 | 10/2005 | |
| EP | 1284688 | B1 | 10/2005 | |
| EP | 1343536 | B1 | 10/2005 | |
| EP | 1027020 | B1 | 11/2005 | |
| EP | 1152780 | B1 | 11/2005 | |
| EP | 1171059 | B1 | 11/2005 | |
| EP | 1237508 | B1 | 11/2005 | |
| EP | 1303234 | B1 | 11/2005 | |
| EP | 1328215 | B1 | 11/2005 | |
| EP | 1341487 | B1 | 11/2005 | |
| EP | 1392197 | B1 | 11/2005 | |
| EP | 1469797 | B1 | 11/2005 | |
| EP | 1255505 | B1 | 12/2005 | |
| EP | 1360942 | B1 | 12/2005 | |
| EP | 1322260 | B1 | 1/2006 | |
| EP | 1359870 | B1 | 1/2006 | |
| EP | 1237586 | B1 | 2/2006 | |
| EP | 1112043 | B1 | 4/2006 | |
| EP | 1309360 | B1 | 4/2006 | |
| EP | 1322259 | B1 | 5/2006 | |
| EP | 1124592 | B1 | 6/2006 | |
| EP | 1237516 | B1 | 6/2006 | |
| EP | 1098673 | B1 | 7/2006 | |
| EP | 1124591 | B1 | 7/2006 | |
| EP | 1083845 | B1 | 8/2006 | |
| EP | 1155666 | B1 | 8/2006 | |
| EP | 1463462 | B1 | 8/2006 | |
| EP | 1684671 | A1 | 8/2006 | |

(56) References Cited

FOREIGN PATENT DOCUMENTS

| | | | |
|---|---|---|---|
| EP | 1519695 | B1 | 9/2006 |
| EP | 1444993 | B1 | 10/2006 |
| EP | 1117350 | B1 | 11/2006 |
| EP | 1212011 | B1 | 11/2006 |
| EP | 1261294 | B1 | 11/2006 |
| EP | 1318775 | B1 | 11/2006 |
| EP | 1429690 | B1 | 11/2006 |
| EP | 1173111 | B1 | 12/2006 |
| EP | 1239795 | B1 | 12/2006 |
| EP | 1299049 | B1 | 12/2006 |
| EP | 1487382 | B1 | 12/2006 |
| EP | 1112044 | B1 | 1/2007 |
| EP | 1482997 | B1 | 1/2007 |
| EP | 1117352 | B1 | 2/2007 |
| EP | 1128849 | B1 | 2/2007 |
| EP | 1392666 | B1 | 2/2007 |
| EP | 1474077 | B1 | 2/2007 |
| EP | 1251805 | B1 | 3/2007 |
| EP | 1117334 | B1 | 4/2007 |
| EP | 1263484 | B1 | 5/2007 |
| EP | 1313410 | B1 | 5/2007 |
| EP | 1370200 | B1 | 5/2007 |
| EP | 1560526 | B1 | 6/2007 |
| EP | 1173117 | B1 | 7/2007 |
| EP | 1434615 | B1 | 7/2007 |
| EP | 1465546 | B1 | 7/2007 |
| EP | 1499366 | B1 | 7/2007 |
| EP | 1225948 | B1 | 8/2007 |
| EP | 1519962 | B1 | 9/2007 |
| EP | 1337285 | B1 | 10/2007 |
| EP | 1112042 | B1 | 11/2007 |
| EP | 1148821 | B1 | 11/2007 |
| EP | 1143882 | B1 | 12/2007 |
| EP | 1330189 | B1 | 12/2007 |
| EP | 1489996 | B1 | 12/2007 |
| EP | 1296618 | B1 | 1/2008 |
| EP | 1401356 | B1 | 1/2008 |
| EP | 1629795 | B1 | 1/2008 |
| EP | 1128786 | B1 | 2/2008 |
| EP | 1616532 | B1 | 2/2008 |
| EP | 1289447 | B1 | 3/2008 |
| EP | 1895942 | A2 | 3/2008 |
| EP | 1115353 | B1 | 5/2008 |
| EP | 1330190 | B1 | 5/2008 |
| EP | 1383448 | B1 | 6/2008 |
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |

(56) References Cited

FOREIGN PATENT DOCUMENTS

| | | | |
|---|---|---|---|
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349098 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |

| | | | |
|---|---|---|---|
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2536353 | A1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |

(56) References Cited

FOREIGN PATENT DOCUMENTS

| | | | |
|---|---|---|---|
| EP | 2241287 | B1 | 1/2013 |
| EP | 2359774 | B1 | 1/2013 |
| EP | 2538878 | A1 | 1/2013 |
| EP | 2538881 | A1 | 1/2013 |
| EP | 2538882 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 2575681 | A1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611388 | A2 | 7/2013 |
| EP | 2611389 | A2 | 7/2013 |
| EP | 2618781 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 2651336 | A1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2670351 | A1 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 2688516 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2777617 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |

(56) References Cited

FOREIGN PATENT DOCUMENTS

| | | | |
|---|---|---|---|
| EP | 2785281 | A1 | 10/2014 |
| EP | 2793743 | A1 | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |
| EP | 2303185 | B1 | 12/2014 |
| EP | 2334857 | B1 | 12/2014 |
| EP | 2365840 | B1 | 12/2014 |
| EP | 2420207 | B1 | 12/2014 |
| EP | 2422750 | B1 | 12/2014 |
| EP | 2707073 | B1 | 12/2014 |
| EP | 1768630 | B1 | 1/2015 |
| EP | 2254515 | B1 | 1/2015 |
| EP | 2641569 | B1 | 1/2015 |
| EP | 2709559 | B1 | 1/2015 |
| EP | 2825203 | A1 | 1/2015 |
| EP | 1903990 | B1 | 2/2015 |
| EP | 2255753 | B1 | 2/2015 |
| EP | 2335649 | B1 | 2/2015 |
| EP | 2522308 | B1 | 2/2015 |
| EP | 2591754 | B1 | 2/2015 |
| EP | 2835112 | A1 | 2/2015 |
| EP | 2838473 | A1 | 2/2015 |
| EP | 1861045 | B1 | 3/2015 |
| EP | 2029057 | B1 | 3/2015 |
| EP | 2193761 | B1 | 3/2015 |
| EP | 2379010 | B1 | 3/2015 |
| EP | 2416737 | B1 | 3/2015 |
| EP | 2849678 | A1 | 3/2015 |
| EP | 1791495 | B1 | 4/2015 |
| EP | 2298252 | B1 | 4/2015 |
| EP | 2536359 | B1 | 4/2015 |
| EP | 2538879 | B1 | 4/2015 |
| EP | 2609894 | B1 | 4/2015 |
| EP | 2693984 | B1 | 4/2015 |
| EP | 2712633 | B1 | 4/2015 |
| EP | 2747707 | B1 | 4/2015 |
| EP | 2856973 | A1 | 4/2015 |
| EP | 2862546 | A1 | 4/2015 |
| EP | 2863842 | A1 | 4/2015 |
| EP | 1465555 | B1 | 5/2015 |
| EP | 1924224 | B1 | 5/2015 |
| EP | 1992369 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2911611 | A1 | 9/2015 |
| EP | 2916781 | A2 | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 2950752 | A2 | 12/2015 |
| EP | 1991168 | B1 | 1/2016 |
| EP | 2254512 | B1 | 1/2016 |
| EP | 2422748 | B1 | 1/2016 |
| EP | 2962664 | A1 | 1/2016 |
| EP | 2964153 | A1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |

(56) References Cited

FOREIGN PATENT DOCUMENTS

| | | | |
|---|---|---|---|
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2621409 | A4 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2991588 | A1 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 2999435 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 3019092 | A1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3038567 | A1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 3043755 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3060171 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 3071149 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2922592 | A4 | 10/2016 |
| EP | 2934387 | B1 | 10/2016 |
| EP | 3076901 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |

(56) References Cited

FOREIGN PATENT DOCUMENTS

| | | | |
|---|---|---|---|
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 3096713 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146937 | A1 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3160396 | A1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |

(56) References Cited

FOREIGN PATENT DOCUMENTS

| | | | |
|---|---|---|---|
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 3220857 | A1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3231395 | A1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3245980 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2670351 | A4 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3266417 | A1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |

(56) References Cited

FOREIGN PATENT DOCUMENTS

| | | | |
|---|---|---|---|
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277222 | A1 | 2/2018 |
| EP | 3280358 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3296979 | A1 | 3/2018 |
| EP | 3298970 | A1 | 3/2018 |
| EP | 3298987 | A1 | 3/2018 |
| EP | 3298988 | A1 | 3/2018 |
| EP | 2209440 | B1 | 4/2018 |
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | B1 | 4/2018 |
| EP | 3095394 | B1 | 4/2018 |
| EP | 3128927 | A4 | 4/2018 |
| EP | 3134033 | B1 | 4/2018 |
| EP | 3137164 | A4 | 4/2018 |
| EP | 3280482 | A4 | 4/2018 |
| EP | 3302297 | A2 | 4/2018 |
| EP | 3302362 | A1 | 4/2018 |
| EP | 3302367 | A1 | 4/2018 |
| EP | 3308745 | A1 | 4/2018 |
| EP | 3310301 | A1 | 4/2018 |
| EP | 3311774 | A1 | 4/2018 |
| EP | 3311783 | A1 | 4/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3322383 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334378 | A1 | 6/2018 |
| EP | 3334380 | A1 | 6/2018 |
| EP | 3334381 | A1 | 6/2018 |
| EP | 3335670 | A1 | 6/2018 |
| EP | 3337412 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |
| EP | 3340923 | A1 | 7/2018 |
| EP | 3340934 | A1 | 7/2018 |
| EP | 3340936 | A1 | 7/2018 |
| EP | 3340945 | A1 | 7/2018 |
| EP | 3342355 | A1 | 7/2018 |
| EP | 3342377 | A1 | 7/2018 |
| EP | 3346952 | A1 | 7/2018 |
| EP | 3347182 | A1 | 7/2018 |
| EP | 3348235 | A1 | 7/2018 |
| EP | 3349693 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |

(56) References Cited

FOREIGN PATENT DOCUMENTS

| | | | |
|---|---|---|---|
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 3370649 | A1 | 9/2018 |
| EP | 3370650 | A1 | 9/2018 |
| EP | 3377000 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 3388027 | A1 | 10/2018 |
| EP | 3389557 | A1 | 10/2018 |
| EP | 3390706 | A1 | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3397206 | A1 | 11/2018 |
| EP | 3398562 | A1 | 11/2018 |
| EP | 3400908 | A1 | 11/2018 |
| EP | 3403616 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3407834 | A1 | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3435919 | A1 | 2/2019 |
| EP | 3441045 | A1 | 2/2019 |
| EP | 3442469 | A1 | 2/2019 |
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3454785 | A1 | 3/2019 |
| EP | 3454786 | A1 | 3/2019 |
| EP | 3454789 | A1 | 3/2019 |

(56) References Cited

FOREIGN PATENT DOCUMENTS

| | | | |
|---|---|---|---|
| EP | 3454794 | A1 | 3/2019 |
| EP | 3457987 | A1 | 3/2019 |
| EP | 3457988 | A1 | 3/2019 |
| EP | 3457990 | A1 | 3/2019 |
| EP | 3458136 | A2 | 3/2019 |
| EP | 3459499 | A2 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 3466373 | A1 | 4/2019 |
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487451 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 3515365 | A1 | 7/2019 |
| EP | 1861043 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |

(56) References Cited

FOREIGN PATENT DOCUMENTS

| | | | |
|---|---|---|---|
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534841 | A1 | 9/2019 |
| EP | 3534845 | A2 | 9/2019 |
| EP | 3535010 | A1 | 9/2019 |
| EP | 3538026 | A1 | 9/2019 |
| EP | 3538027 | A1 | 9/2019 |
| EP | 3539508 | A1 | 9/2019 |
| EP | 3539509 | A1 | 9/2019 |
| EP | 3541316 | A1 | 9/2019 |
| EP | 3541325 | A1 | 9/2019 |
| EP | 3541328 | A1 | 9/2019 |
| EP | 3542758 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |
| EP | 3057522 | B1 | 10/2019 |
| EP | 3067075 | B1 | 10/2019 |
| EP | 3146937 | B1 | 10/2019 |
| EP | 3238777 | B1 | 10/2019 |
| EP | 3359211 | B1 | 10/2019 |
| EP | 3388026 | B1 | 10/2019 |
| EP | 3432806 | B1 | 10/2019 |
| EP | 3496626 | A4 | 10/2019 |
| EP | 3544548 | A1 | 10/2019 |
| EP | 3547936 | A1 | 10/2019 |
| EP | 3547966 | A1 | 10/2019 |
| EP | 3549555 | A1 | 10/2019 |
| EP | 3552585 | A1 | 10/2019 |
| EP | 3554424 | A1 | 10/2019 |
| EP | 3556323 | A1 | 10/2019 |
| EP | 3558165 | A1 | 10/2019 |
| EP | 3558168 | A1 | 10/2019 |
| EP | 3558169 | A2 | 10/2019 |
| EP | 2043559 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| EP | 3572045 | A1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3579788 | A1 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3595588 | A1 | 1/2020 |
| EP | 3600159 | A1 | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3628239 | A1 | 4/2020 |
| EP | 3628274 | A1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |

(56) References Cited

FOREIGN PATENT DOCUMENTS

| | | | |
|---|---|---|---|
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648706 | A1 | 5/2020 |
| EP | 3648709 | A1 | 5/2020 |
| EP | 3656354 | A1 | 5/2020 |
| EP | 1648339 | B2 | 6/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |
| EP | 3060165 | B1 | 6/2020 |
| EP | 3280338 | B1 | 6/2020 |
| EP | 3283010 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3661436 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 2271284 | B1 | 7/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3672532 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 3685802 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |
| EP | 3634255 | B1 | 8/2020 |
| EP | 3689299 | A1 | 8/2020 |
| EP | 3691567 | A1 | 8/2020 |
| EP | 3695810 | A1 | 8/2020 |
| EP | 3697342 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3718509 | A1 | 10/2020 |
| EP | 3720363 | A1 | 10/2020 |
| EP | 3721811 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3737336 | A1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3744291 | A1 | 12/2020 |
| EP | 3749254 | A1 | 12/2020 |
| EP | 3753535 | A1 | 12/2020 |
| EP | 3756623 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |

(56) References Cited

FOREIGN PATENT DOCUMENTS

| | | | |
|---|---|---|---|
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3760164 | A1 | 1/2021 |
| EP | 3763331 | A1 | 1/2021 |
| EP | 3769721 | A1 | 1/2021 |
| EP | 2273951 | B1 | 2/2021 |
| EP | 2379008 | B1 | 2/2021 |
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773271 | A1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3791828 | A1 | 3/2021 |
| EP | 3796872 | A1 | 3/2021 |
| EP | 3796873 | A1 | 3/2021 |
| EP | 3796875 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 2249711 | B1 | 10/2021 |
| EP | 2538883 | B1 | 10/2021 |

(56) References Cited

FOREIGN PATENT DOCUMENTS

| | | | |
|---|---|---|---|
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3892240 | A1 | 10/2021 |
| EP | 3897454 | A1 | 10/2021 |
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 3912596 | A1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3914191 | A1 | 12/2021 |
| EP | 3915493 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3193782 | B1 | 3/2022 |
| EP | 3334380 | B1 | 3/2022 |
| EP | 3355800 | B1 | 3/2022 |
| EP | 3479797 | B1 | 3/2022 |
| EP | 3479800 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |

(56) References Cited

FOREIGN PATENT DOCUMENTS

| | | | | | |
|---|---|---|---|---|---|
| EP | 3796872 | B1 | | 7/2022 | |
| EP | 3796876 | B1 | | 7/2022 | |
| EP | 2313152 | B1 | | 8/2022 | |
| EP | 2688516 | B1 | | 8/2022 | |
| EP | 2849678 | B1 | | 8/2022 | |
| EP | 2950751 | B1 | | 8/2022 | |
| EP | 2964153 | B1 | | 8/2022 | |
| EP | 3019092 | B1 | | 8/2022 | |
| EP | 3184082 | B1 | | 8/2022 | |
| EP | 3231395 | B1 | | 8/2022 | |
| EP | 3266417 | B1 | | 8/2022 | |
| EP | 3407834 | B1 | | 8/2022 | |
| EP | 3458136 | B1 | | 8/2022 | |
| EP | 3459499 | B1 | | 8/2022 | |
| EP | 3471662 | B1 | | 8/2022 | |
| EP | 3484412 | B1 | | 8/2022 | |
| EP | 3534841 | B1 | | 8/2022 | |
| EP | 3541328 | B1 | | 8/2022 | |
| EP | 3672532 | B1 | | 8/2022 | |
| EP | 3718509 | B1 | | 8/2022 | |
| EP | 3769721 | B1 | | 8/2022 | |
| EP | 3789077 | B1 | | 8/2022 | |
| EP | 3908228 | B1 | | 8/2022 | |
| EP | 3915493 | B1 | | 8/2022 | |
| EP | 3967274 | B1 | | 8/2022 | |
| EP | 2670351 | B1 | | 9/2022 | |
| EP | 2777617 | B1 | | 9/2022 | |
| EP | 2810620 | B1 | | 9/2022 | |
| EP | 2922592 | B1 | * | 9/2022 | A61F 2/2433 |
| EP | 3038567 | B1 | | 9/2022 | |
| EP | 3096713 | B1 | | 9/2022 | |
| EP | 3448315 | B1 | | 9/2022 | |
| EP | 3481335 | B1 | | 9/2022 | |
| EP | 3520715 | B1 | | 9/2022 | |
| EP | 3946163 | | | 12/2022 | |
| FR | 2815844 | B1 | | 1/2003 | |
| FR | 2826863 | B1 | | 9/2003 | |
| FR | 2828091 | B1 | | 11/2003 | |
| FR | 2863160 | A1 | * | 6/2005 | A61F 2/95 |
| FR | 2858543 | B1 | | 2/2006 | |
| FR | 2828263 | B1 | | 5/2007 | |
| FR | 2847800 | B1 | | 5/2007 | |
| FR | 2874812 | B1 | | 6/2007 | |
| FR | 2874813 | B1 | | 6/2007 | |
| FR | 2883721 | B1 | | 6/2007 | |
| FR | 2894131 | B1 | | 12/2008 | |
| FR | 2899096 | B1 | | 12/2008 | |
| FR | 2910269 | B1 | | 2/2009 | |
| FR | 2909857 | B1 | | 3/2009 | |
| FR | 2906454 | B1 | | 4/2009 | |
| FR | 2906998 | B1 | | 4/2009 | |
| FR | 2913879 | B1 | | 6/2009 | |
| FR | 2916959 | B1 | | 9/2009 | |
| FR | 2892939 | B1 | | 1/2010 | |
| FR | 2915678 | B1 | | 4/2010 | |
| FR | 2930137 | B1 | | 4/2010 | |
| FR | 2915903 | B1 | | 6/2010 | |
| FR | 2916627 | B1 | | 9/2010 | |
| FR | 2920664 | B1 | | 9/2010 | |
| FR | 2932376 | B1 | | 4/2011 | |
| FR | 2947716 | B1 | | 9/2011 | |
| FR | 2945440 | B1 | | 12/2012 | |
| FR | 2951549 | B1 | | 8/2013 | |
| FR | 2964855 | B1 | | 10/2013 | |
| FR | 2977792 | B1 | | 10/2013 | |
| FR | 2980968 | B1 | | 12/2013 | |
| FR | 2986149 | B1 | | 12/2014 | |
| FR | 2997288 | B1 | | 1/2015 | |
| FR | 2998167 | B1 | | 1/2015 | |
| FR | 2996747 | B1 | | 2/2015 | |
| FR | 2996748 | B1 | | 2/2015 | |
| FR | 3004638 | B1 | | 5/2015 | |
| FR | 2982763 | B1 | | 7/2015 | |
| FR | 2991162 | B1 | | 7/2015 | |
| FR | 3006582 | B1 | | 7/2015 | |
| FR | 3001121 | B1 | | 1/2016 | |
| FR | 2998166 | B1 | | 2/2016 | |
| FR | 3021862 | B1 | | 5/2016 | |
| FR | 3004917 | B1 | | 6/2016 | |
| FR | 3006884 | B1 | | 6/2016 | |
| FR | 3023704 | B1 | | 8/2016 | |
| FR | 3008885 | B1 | | 12/2016 | |
| FR | 3033494 | B1 | | 3/2017 | |
| FR | 3060292 | A1 | | 6/2018 | |
| FR | 3057154 | B1 | | 10/2018 | |
| FR | 3058631 | B1 | | 1/2019 | |
| FR | 3058632 | B1 | | 1/2019 | |
| FR | 3060292 | B1 | | 1/2019 | |
| FR | 3063631 | B1 | | 3/2019 | |
| FR | 3020265 | B1 | | 9/2019 | |
| FR | 3072013 | B1 | | 9/2019 | |
| GB | 243370 | A | | 8/1926 | |
| GB | 2407146 | B | | 4/2006 | |
| GB | 2398245 | B | | 3/2007 | |
| GB | 2433700 | B | | 12/2007 | |
| GB | 2478498 | B | | 7/2012 | |
| GB | 2491478 | A | * | 12/2012 | A61F 2/9517 |
| GB | 2530487 | B | | 12/2016 | |
| GB | 2517609 | B | | 5/2017 | |
| GB | 2538749 | B | | 8/2017 | |
| GB | 2538072 | B | | 11/2017 | |
| GB | 2536538 | B | | 7/2018 | |
| GB | 2548891 | B | | 7/2018 | |
| JP | 2013525039 | | | 6/2013 | |
| JP | 2016518211 | A | | 6/2016 | |
| JP | 2019504709 | A | | 2/2019 | |
| JP | 2022519948 | A | | 3/2022 | |
| JP | 7438236 | | | 2/2024 | |
| WO | WO-2005062980 | A2 | | 7/2005 | |
| WO | WO-2009134701 | A2 | | 11/2009 | |
| WO | WO-2015006139 | A1 | | 1/2014 | |
| WO | WO-2017139380 | A1 | | 8/2017 | |
| WO | WO-2018195215 | A2 | * | 10/2018 | A61F 2/2442 |
| WO | WO-2019014473 | A1 | * | 1/2019 | A61F 2/2418 |
| WO | WO-2020206012 | A1 | | 10/2020 | |

OTHER PUBLICATIONS

"Chinese Application Serial No. 202080033982.8, Response filed Sep. 19, 2024 to Office Action mailed Jul. 23, 2024", W English Claims, 12 pgs.
"Australian Application Serial No. 2022291665, First Examination Report mailed Jan. 12, 2024", 5 pgs.
"Chinese Application Serial No. 202080033982.8, Office Action mailed Jan. 8, 2024", w English Translation, 21 pgs.
"U.S. Appl. No. 16/837,884, Non Final Office Action mailed Jun. 8, 2022", 9 pgs.
"U.S. Appl. No. 16/837,884, Notice of Allowance mailed Nov. 9, 2022", 9 pgs.
"U.S. Appl. No. 16/837,884, Response filed Feb. 28, 2022 to Restriction Requirement mailed Dec. 27, 2021", 10 pgs.
"U.S. Appl. No. 16/837,884, Response filed Sep. 7, 2022 to Non Final Office Action mailed Jun. 8, 2022", 15 pgs.
"U.S. Appl. No. 16/837,884, Restriction Requirement mailed Dec. 27, 2021", 9 pgs.
"U.S. Appl. No. 16/837,884, Supplemental Notice of Allowability mailed Feb. 10, 2023", 2 pgs.
"Australian Application Serial No. 2020256195, First Examination Report mailed Jul. 12, 2022", 4 pgs.
"Australian Application Serial No. 2020256195, Response filed Sep. 19, 2022 to First Examination Report mailed Jul. 12, 2022", 25 pgs.
"Canadian Application Serial No. 3,135,753, Office Action mailed Dec. 15, 2022", 5 pgs.
"Canadian Application Serial No. 3,135,753, Response filed Apr. 13, 2023 to Office Action mailed Dec. 15, 2022", 34 pgs.
"European Application Serial No. 20784615.5, Extended European Search Report mailed Nov. 17, 2022", 4 pgs.
"European Application Serial No. 20784615.5, Response filed May 4, 2022 to Communication mailed Nov. 18, 2021", 11 pgs.

(56) References Cited

OTHER PUBLICATIONS

"International Application Serial No. PCT/US2020/026236, International Preliminary Report on Patentability mailed Oct. 14, 2021", 14 pgs.
"International Application Serial No. PCT/US2020/026236, International Search Report mailed Jun. 15, 2020", 2 pgs.
"International Application Serial No. PCT/US2020/026236, Written Opinion mailed Jun. 15, 2020", 12 pgs.
"Japanese Application Serial No. 2021-558833, Notification of Reasons for Refusal mailed Jan. 31, 2023", w/ English Translation, 9 pgs.
"Japanese Application Serial No. 2021-558833, Response filed May 1, 2023 to Notification of Reasons for Refusal mailed Jan. 31, 2023", w/ English Claims, 7 pgs.
Extended European Search Report and Opinion received for European Patent Application No. 25196294.0 mailed on Jan. 23, 2026, 6 pages.
"Australian Application Serial No. 2020256195, Response filed Oct. 13, 2022 to First Examination Report mailed Jul. 12, 2022", 25 pgs.
Notice of Allowance received for European Patent Application No. 20784615.5 mailed on Mar. 14, 2025, 9 pages.
U.S. Appl. No. 16/837,884 U.S. Pat. No. 11,602,429, Apr. 1, 2020, Controllably Deployable Prosthetic Valve.
"European Application Serial No. 20784615.5, Response filed Jun. 16, 2023 to Extended European Search Report mailed Nov. 17, 2022", 15 pgs.
"Japanese Application Serial No. 2021-558833, Notification of Reasons for Refusal mailed Aug. 24, 2023", w English Translation, 11 pgs.
"Chinese Application Serial No. 202080033982.8, Response filed May 22, 2024 to Office Action mailed Jan. 8, 2024", w current English claims, 20 pgs.
"Japanese Application Serial No. 2021-558833, Response filed Oct. 18, 2023 to Notification of Reasons for Refusal mailed Aug. 24, 2023", w/ current English claims, 8 pgs.

* cited by examiner

CONTROLLABLY DEPLOYABLE PROSTHETIC VALVE

CLAIM OF PRIORITY

The present application is a continuation of U.S. Non-Provisional patent application Ser. No. 16/837,884 filed on Apr. 1, 2020, which is a non-provisional of, and claims the benefit of U.S. Provisional Patent Application No. 62/827,380 filed on Apr. 1, 2019; the entire contents of which are incorporated herein by reference.

BACKGROUND

The heart of vertebrate animals is divided into four chambers, and is equipped with four valves (the mitral, aortic, pulmonary and tricuspid valves) that ensure that blood pumped by the heart flows in a forward direction through the cardiovascular system without backflow. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (also referred to as regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or reshaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

BRIEF DESCRIPTION OF THE DRAWINGS

In the drawings, which are not necessarily drawn to scale, like numerals may describe similar components in different views or similar steps. Like numerals having different letter suffixes may represent different instances of similar components. The drawings illustrate generally, by way of example, but not by way of limitation, various examples discussed in the present document.

DETAILED DESCRIPTION

While some of the surgical and less invasive treatments for valvar regurgitation are promising, they can be difficult to deliver, expensive to manufacture, or may not be indicated for all patients. Therefore, it would be desirable to provide improved devices and methods for the treatment of valvar insufficiency such as mitral insufficiency. At least some of these objectives will be met by the devices and methods disclosed.

Specific examples of the disclosed device, delivery system, and method will now be described with reference to the drawings. Nothing in this detailed description is intended to imply that any particular component, feature, or step is essential to the invention.

Cardiac Anatomy

Figure 1:
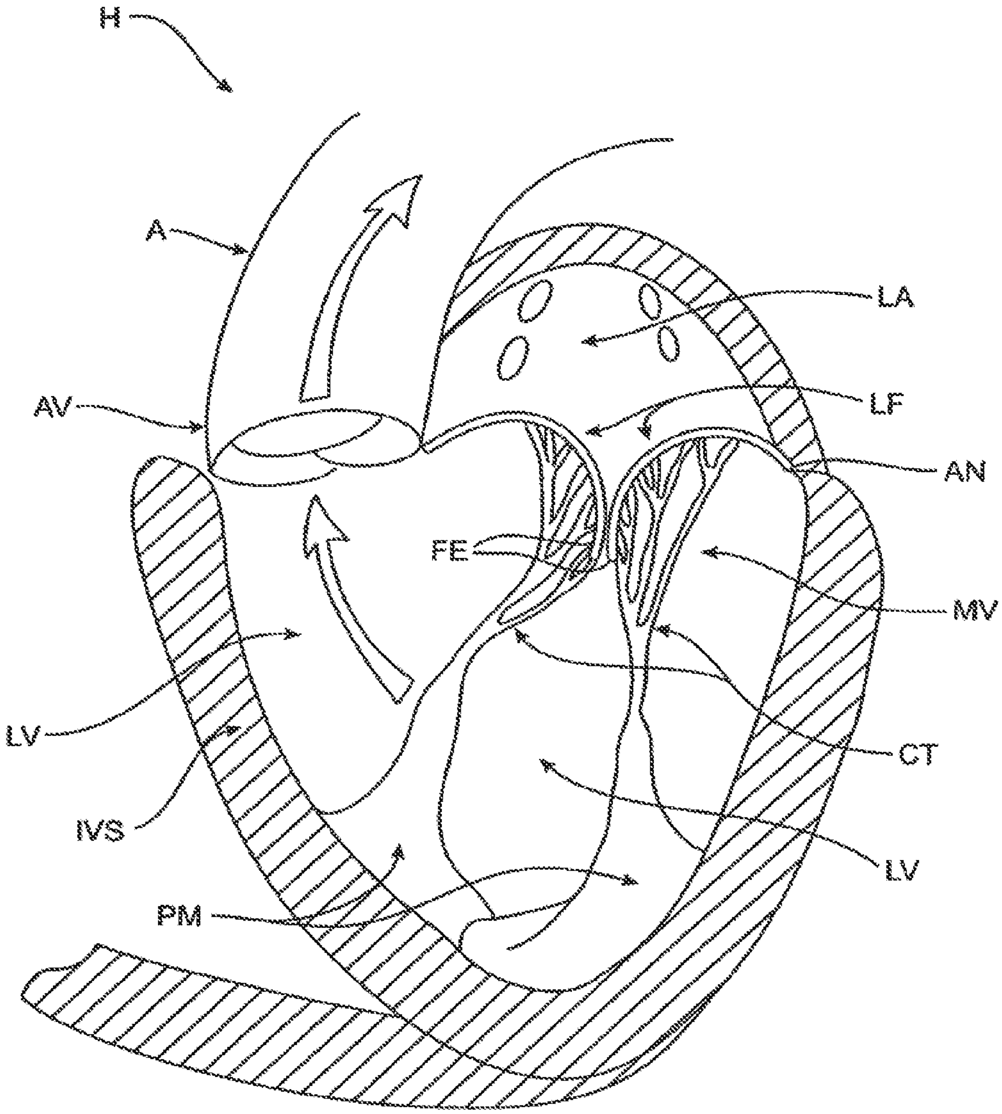
FIG. 1 is a schematic illustration of the left ventricle of a heart showing blood flow during systole with arrows.

The left ventricle LV of a normal heart H in systole is illustrated in FIG. 1. The left ventricle LV is contracting and blood flows outwardly through the aortic valve AV which is a tricuspid valve, in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
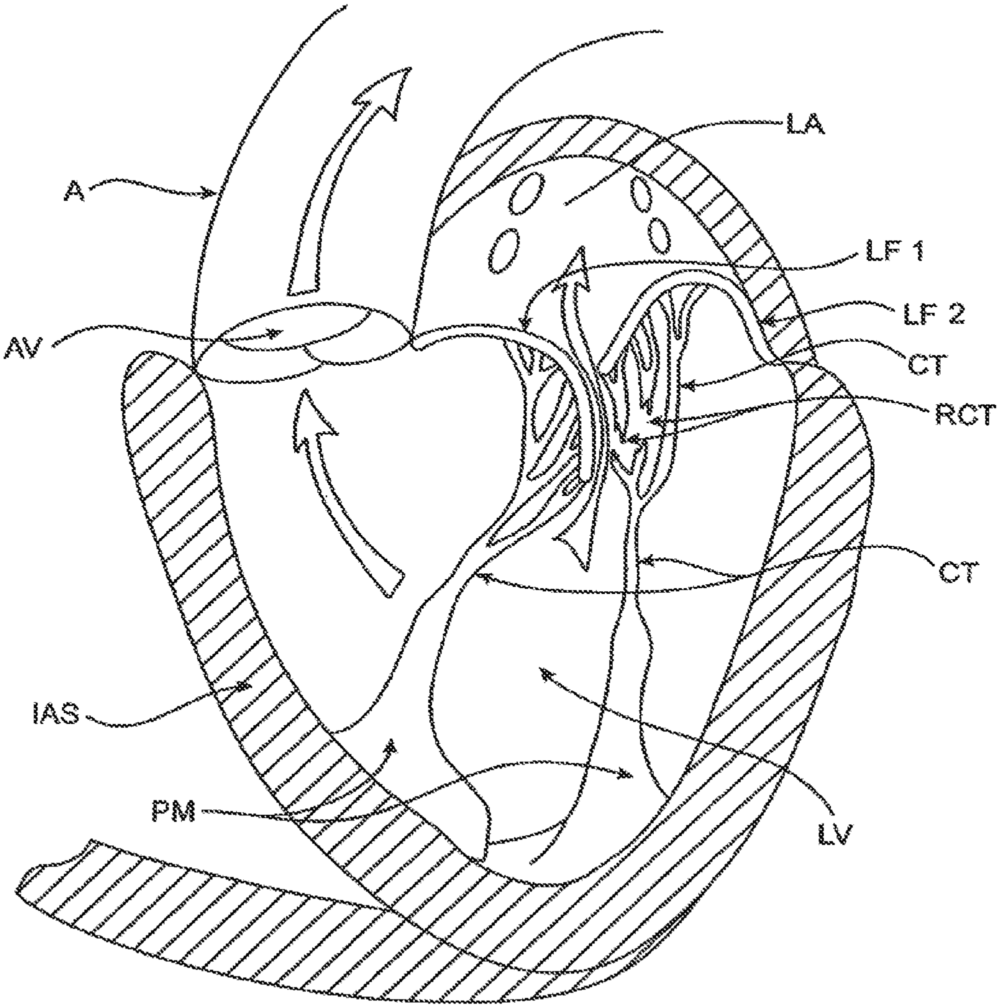
FIG. 2 is a schematic illustration of the left ventricle of a heart having prolapsed leaflets in the mitral valve.
Figure 3:
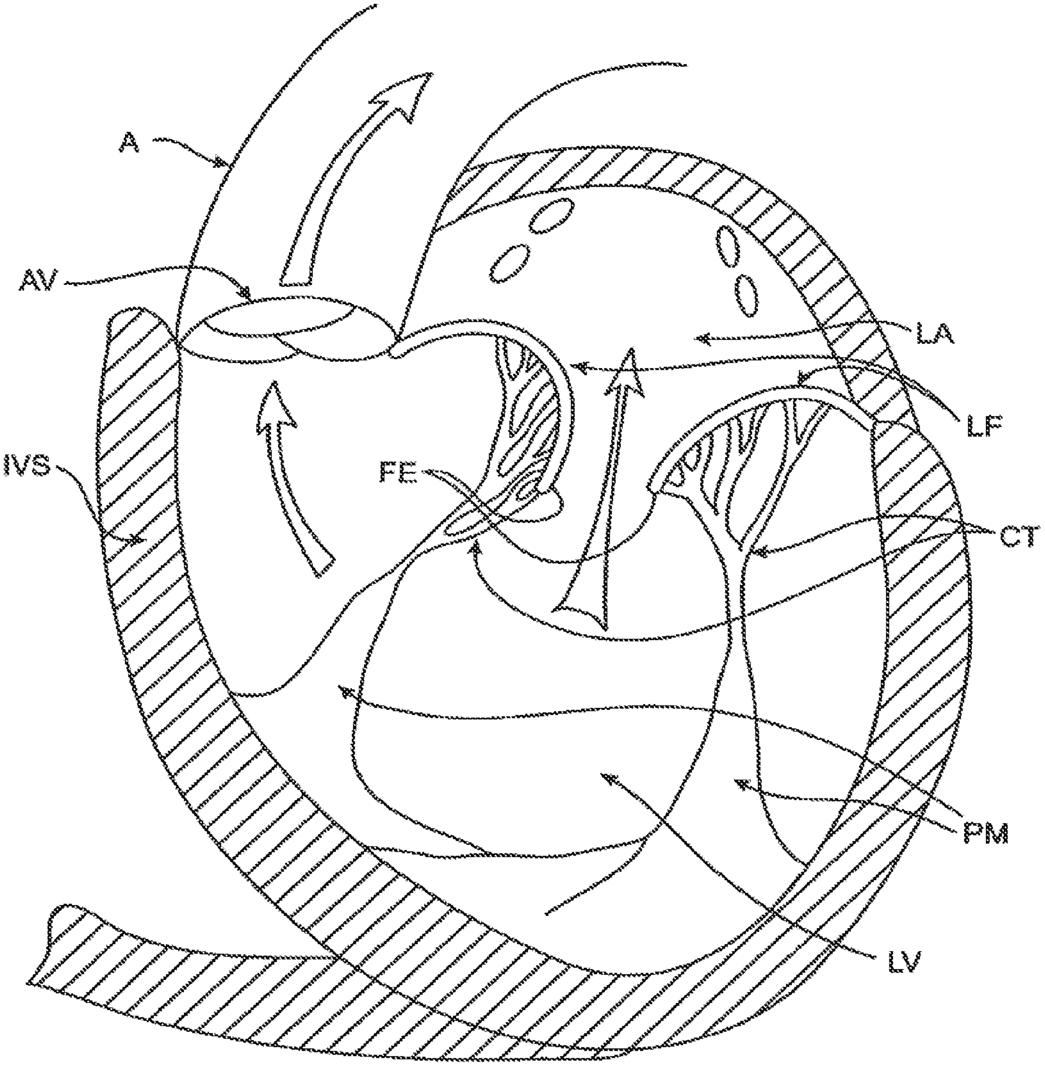
FIG. 3 is a schematic illustration of a heart in a patient suffering from cardiomyopathy where the heart is dilated, and the leaflets do not meet.
Figure 4:
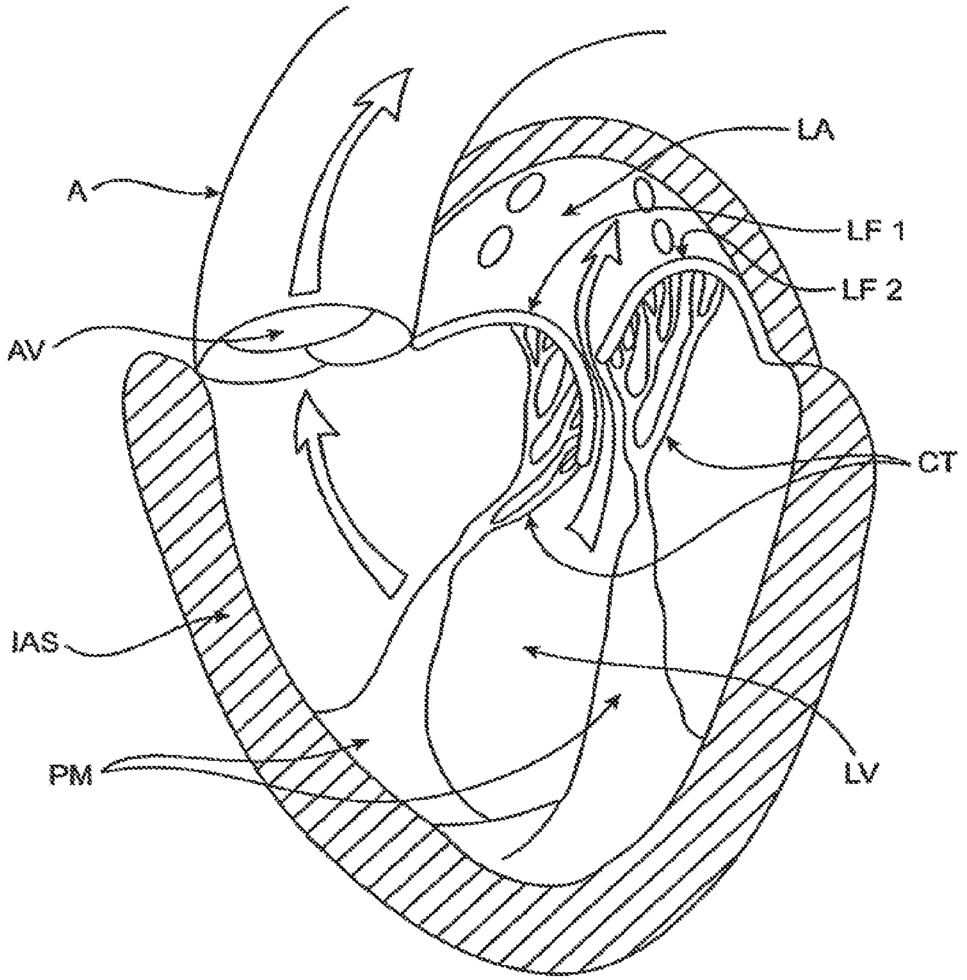
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
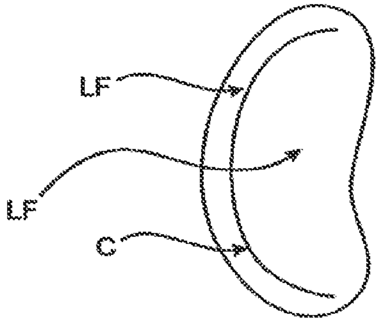
FIG. 3A shows, normal closure of the leaflets.
Figure 3B:
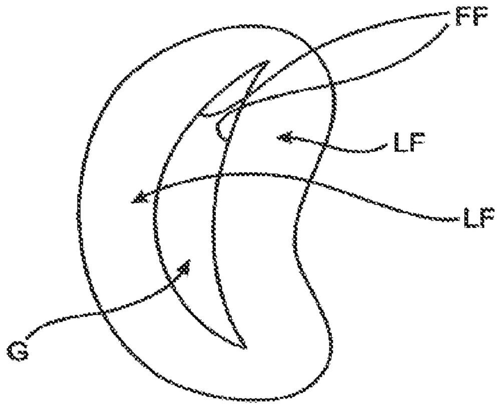
FIG. 3B shows abnormal closure in the dilated heart.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
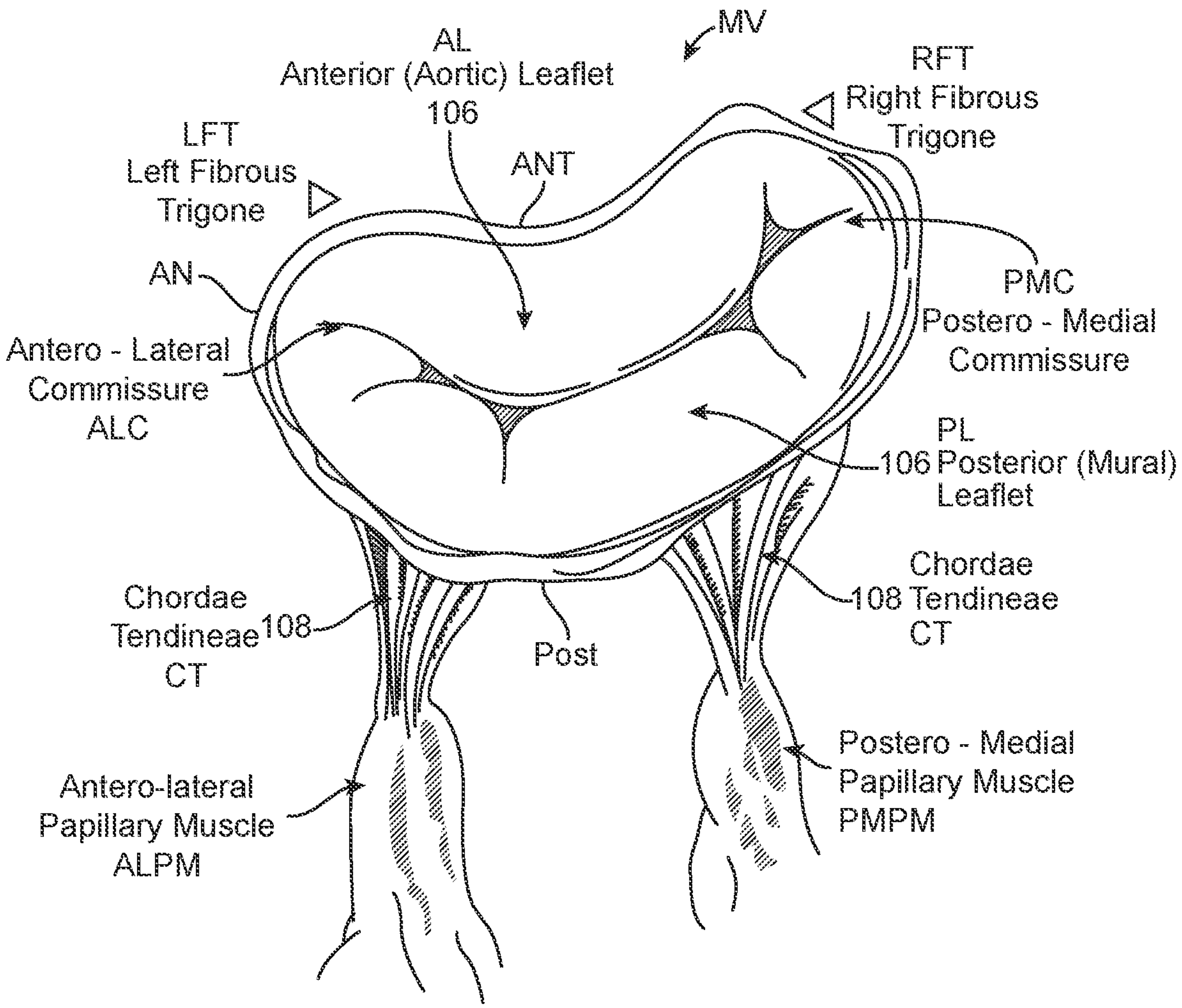
FIGS. 5A-5B illustrate basic mitral valve anatomy.
Figure 5B:
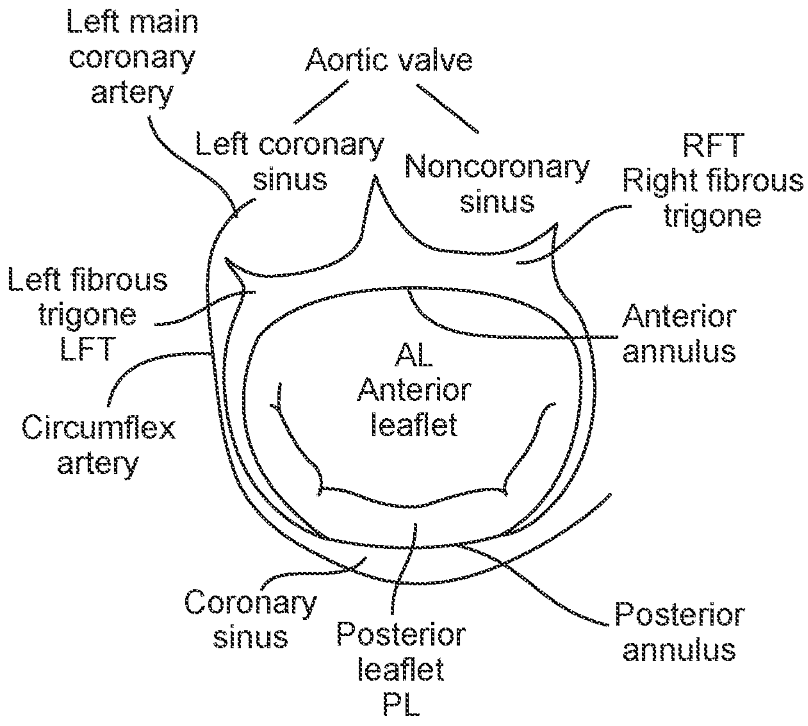

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the examples disclosed herein are directed to an implantable prosthetic mitral valve for treating mitral regurgitation, one of skill in the art will appreciate that this is not intended to be limiting, and the device and methods disclosed herein may also be used to treat other valves such as cardiac valves like the tricuspid valve, aortic valve, pulmonary valve, etc, as well as other valves in the body such as venous valves.

Prosthetic Valve

Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue or a synthetic material, or combinations thereof. The prosthetic valve once implanted, takes over for malfunctioning native valve, thereby reducing or eliminating valvar insufficiency. While some of these valves appear promising, there still is a need for improved valves. The following discloses examples of a prosthetic valve, a delivery system for the prosthetic valve, and methods of delivering the valve that may overcome some of the challenges associated with existing prosthetic valves.

Figure 6:
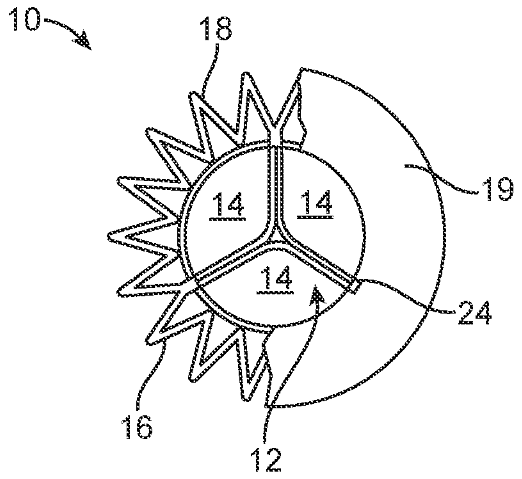
FIG. 6 illustrates a bottom, partial cross-sectional view of an example prosthetic mitral valve.
Figure 7:
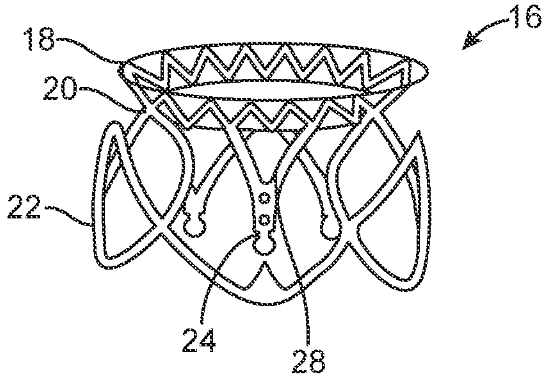
FIG. 7 is a perspective view of the anchor portion of the prosthetic mitral valve seen in FIG. 6.

Referring now to FIGS. 6-7, examples of a mitral valve prosthesis generally designated with reference numeral 10 comprise tricuspid tissue-type prosthetic one-way valve structure 12 comprising leaflets 14 affixed within self-expanding or expandable anchor portion 16 having a geometry that expands into low profile atrial skirt region 18, annular region 20, ventricular skirt region 22, and a plurality of leaflet commissures 24 (also referred to herein as commissure posts) extending axially in a cantilevered fashion downstream into the sub-annular space defined by ventricular skirt region 22.

FIG. 6 shows a partial cross-section of the valve 10 from the patient's left ventricle looking upward toward the right atrium. The atrial skirt region 18 is anchored to a lower portion of the right atrium 19. The valve leaflets 14 have an open position (not illustrated) and a closed position illustrated in FIG. 6. In the open position, the leaflets 14 are displaced away from one another to allow blood flow therepast, and in the closed position, the leaflets 14 engage one another to close the valve and prevent retrograde blood flow therepast. The valve commissures 24 may be configured to optimize the efficiency of the prosthetic valve structure 12 and the load distribution on the leaflets 14 by providing for the attachment of the leaflets 14 along arcuate seams 28 (best seen in FIG. 7), and by being made selectively flexible at different points or zones along their axial length through the addition/deletion of reinforcing struts.

FIG. 7 shows a perspective view of the anchor portion 16 of the valve 10 which has been formed from a series of interconnected struts. The atrial skirt region 18 forms an annular flanged region on the anchor to help secure an upper portion of the prosthetic valve in the atrium, and the annular region 20 is a cylindrical region for anchoring the valve along the native valve annulus. The ventricular skirt region 22 similarly is cylindrically shaped and helps anchor a lower portion of the valve in the patient's left ventricle. Any portion, or all of the anchor may be covered with tissue such as pericardium or other tissues disclosed herein, or a synthetic material such as Dacron or ePTFE may be used to cover the anchor. The covering helps to seal the anchor to the native valve, and this helps funnel blood into and through the prosthetic valve, rather than around the valve. In some examples, the anchor may remain uncovered. The prosthetic valve has an expanded configuration and a collapsed configuration. The collapsed configuration has a low profile cylindrical shape that is suitable for mounting on a delivery system and delivery may be made either transluminally on a catheter, or transapically through the heart wall. The expanded configuration (as illustrated) allows the prosthetic valve to be anchored into a desired position.

Figure 8A:
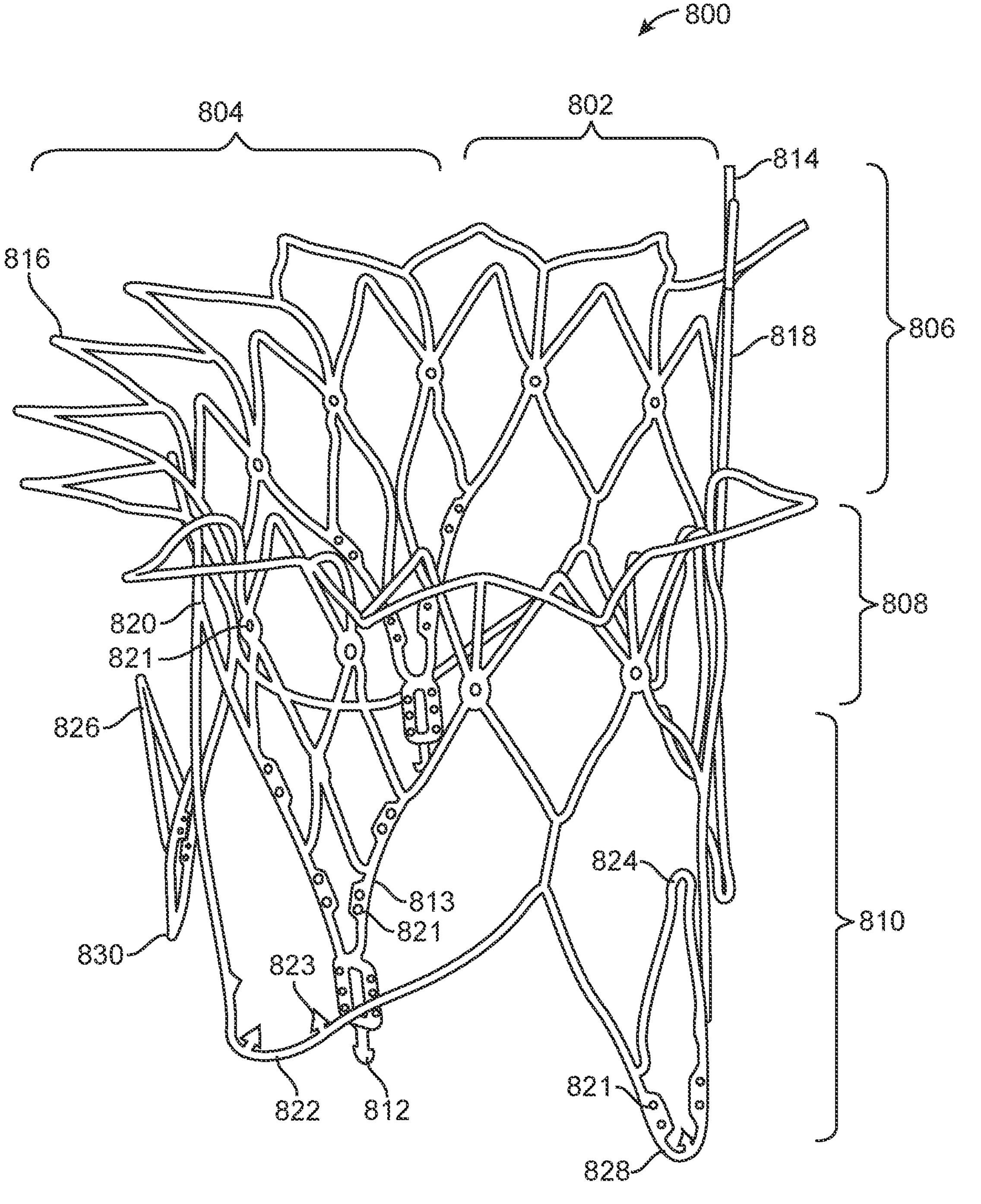
FIG. 8A is a perspective view of a prosthetic mitral valve.
Figure 8B:
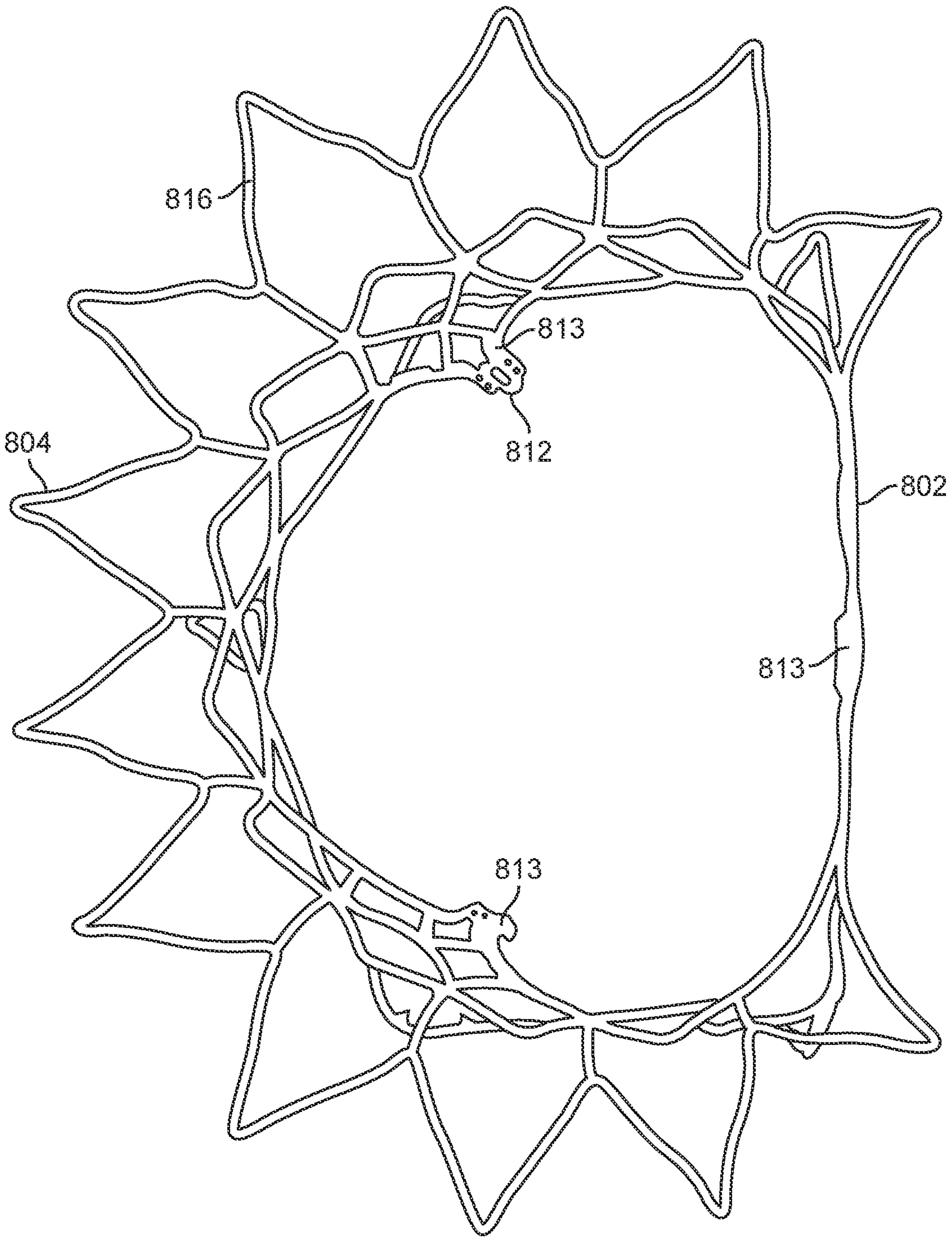
FIG. 8B is a top view from the atrium of the prosthetic valve in FIG. 8A.

FIG. 8A illustrates a perspective view of an example of a prosthetic mitral valve with optional coverings removed to allow visibility of the anchor struts. FIG. 8B illustrates a top view of the prosthetic valve in FIG. 8A from the atrium looking down into the ventricle. The valve 800 includes an asymmetrical expanded anchor portion having a D-shaped cross-section. As shown, the anchor portion generally comprises anterior 802 and posterior 804 aspects along the longitudinal axis thereof, as well as atrial 806, annular 808 and ventricular 810 regions that correspond generally to the atrial skirt 18, annular 20 and ventricular skirt 22 regions of the example described above in FIGS. 6-7. Commissures (also referred to herein as commissure posts) 813 also correspond generally to the leaflets 14 of the examples in FIGS. 6-7. The prosthetic valve 800 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the diseased or damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other examples, the anchor may be expandable with an expandable member such as a balloon. In any example, the anchor is fabricated by laser cutting, electrical discharge machining (EDM), or photochemically etching a tube such as hypodermic needle tubing. The anchor may also be fabricated by photochemically etching a flat sheet of material which is then rolled up with the opposing ends welded together.

The atrial skirt portion 816 forms a flanged region that helps to anchor the prosthetic valve to the atrium, above the mitral valve. The atrial skirt includes a plurality of triangular fingers which extend radially outward from the anchor to form the flange. The posterior 804 portion of the atrial skirt 816 is generally round or circular, while a portion of the anterior 802 part of the atrial skirt 816 is flat. Thus, the atrial skirt region may have a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some examples, the atrial skirt lies in a plane that is substantially perpendicular to the central axis of the valve. The anterior portion 802 of the atrial skirt 806 optionally includes an alignment element 814 which may be one or more struts which extend vertically upward and substantially parallel to the prosthetic valve. The alignment element 814 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 820 which also has a collapsed configuration for delivery, and an expanded configuration for anchoring the prosthetic valve along the native valve annulus. The annular region is also comprised of a plurality of interconnected struts that form a series of cells, either closed cells or open cells. Suture holes 821 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in any example may have a posterior portion 804 which is circular, and an anterior portion 802 which is flat, thereby forming a D-shaped cross-section. This D-shaped cross-section conforms better to the native mitral valve anatomy without obstructing blood flow in other areas of the heart such as by impinging on the left ventricular outflow tract.

The lower portion of the prosthetic valve includes the ventricular skirt region 828. The ventricular skirt region also has a collapsed configuration for delivery, and an expanded configuration for anchoring. It is formed from a plurality of interconnected struts that form a series of cells, that may be closed, that can radially expand. The ventricular skirt in the expanded configuration anchors the prosthetic valve to the ventricle by expanding against the native mitral valve leaflets. Optional barbs 823 in the ventricular skirt may be used to further help anchor the prosthetic valve into the ventricular tissue. Barbs may optionally also be included in the atrial skirt portion as well as the annular region of the anchor. Additionally, optional suture holes 821 in the ventricular skirt may be used to help suture tissue or another material to the ventricular skirt region, similarly as discussed above. The anterior 802 portion of the ventricular skirt may be flat, and the posterior 804 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal anchor tabs and posterior anchor tab have expanded, as will be explained in greater detail below.

The ventricular skirt portion may optionally also include a pair of ventricular trigonal tabs 824 on the anterior portion of the anchor (only 1 visible in this view) for helping to anchor the prosthetic valve as will be discussed in greater detail below. The ventricular skirt may also optionally include a posterior tab 826 on a posterior portion 804 of the ventricular skirt for anchoring the prosthetic valve to a posterior portion of the annulus. The trigonal tabs 824 or the posterior tab 826 are tabs that extend radially outward from the anchor, and they are inclined upward in the upstream direction.

The actual valve mechanism is formed from three commissure posts (also referred to as commissures) 813 which extend radially inward toward the central axis of the anchor in a funnel or cone-like shape. The commissures 813 are formed from a plurality of interconnected struts that create the triangular shaped commissures. The struts of the commissures may include one or more suture holes 821 that allow tissue or a synthetic material to be attached to the commissures. In this example, the valve is a tricuspid valve, therefore it includes three commissures 813. The tips of the commissures may include a commissure tab 812 (also referred to as a tab) for engaging a delivery catheter. In this example, the tabs have enlarged head regions connected to a narrower neck, forming a mushroom-like shape. The commissures may be biased in any position, but may angle inward slightly toward the central axis of the prosthetic valve so that retrograde blood flow forces the commissures into apposition with one another to close the valve, and antegrade blood flow pushes the commissures radially outward, to fully open the valve. FIG. 8B is a top view illustrating the prosthetic valve of FIG. 8A from the atrial side, and shows the D-shaped cross-section.

Figure 9A:
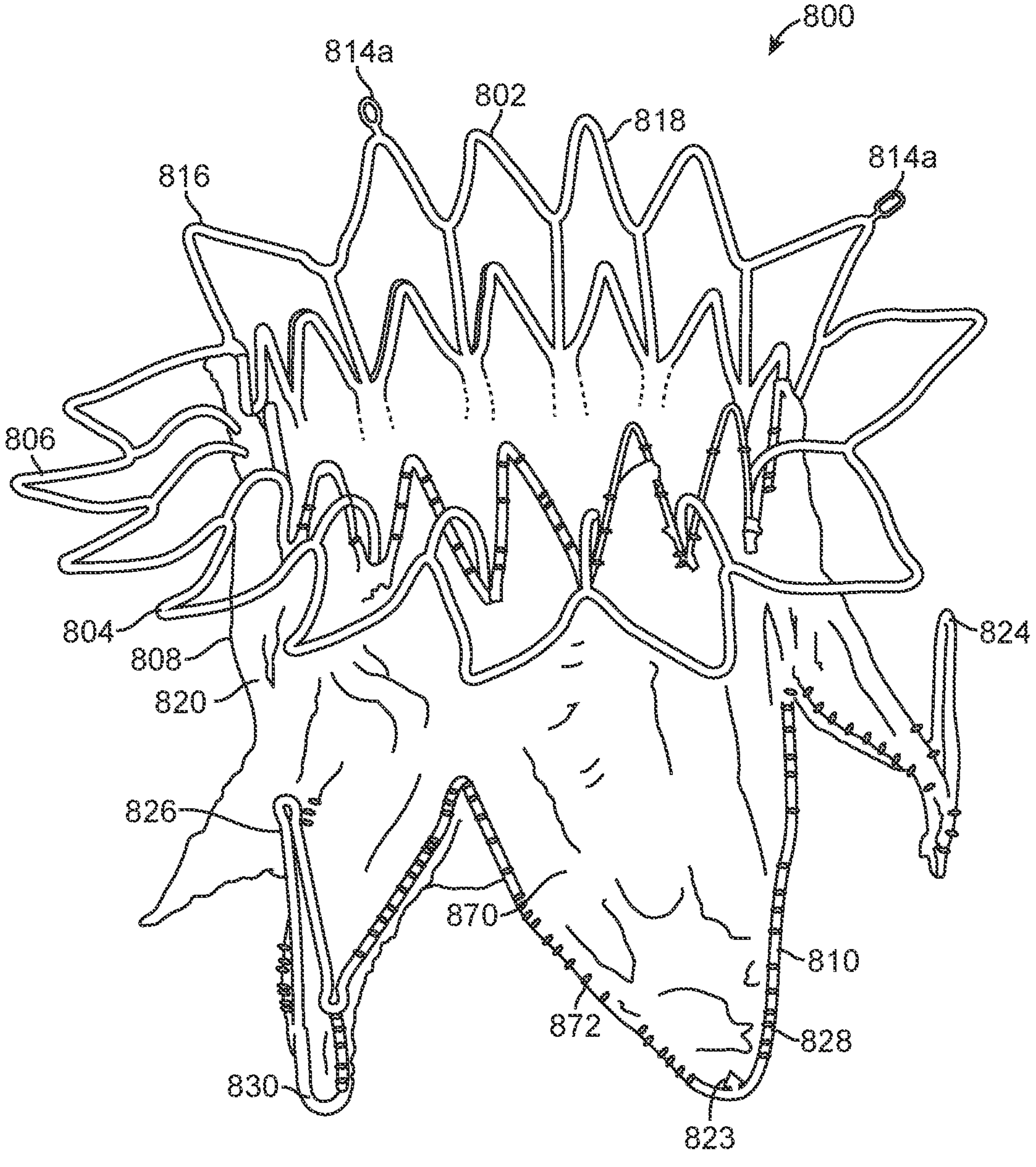
FIG. 9A illustrates a perspective view of the prosthetic valve in FIG. 8A from the atrium.

FIG. 9A illustrates the prosthetic mitral valve of FIGS. 8A-8B with a covering 870 coupled to portions of the anchor with suture 872. This view is taken from an atrial perspective. In this example, the covering may be pericardium which may come from a number of sources as disclosed elsewhere in this specification. In alternative examples, the covering may be a polymer such as Dacron polyester, ePTFE, or another synthetic material. The covering may be disposed over the annular region 820 and the ventricular skirt region 828, and in some examples the anterior ventricular trigonal 824 tabs and the ventricular posterior tab 830 may also be covered with the same or a different material. The covering helps seal the anchor against the adjacent tissue so that blood funnels through the valve mechanism. In this example, the atrial skirt is left uncovered, as well as tabs 824, 830 but they may be covered if desired. Additionally, radiopaque markers 814*a* form a portion of the alignment element and facilitate visualization of the prosthetic valve under fluoroscopy which is important during alignment of the valve.

Figure 9B:
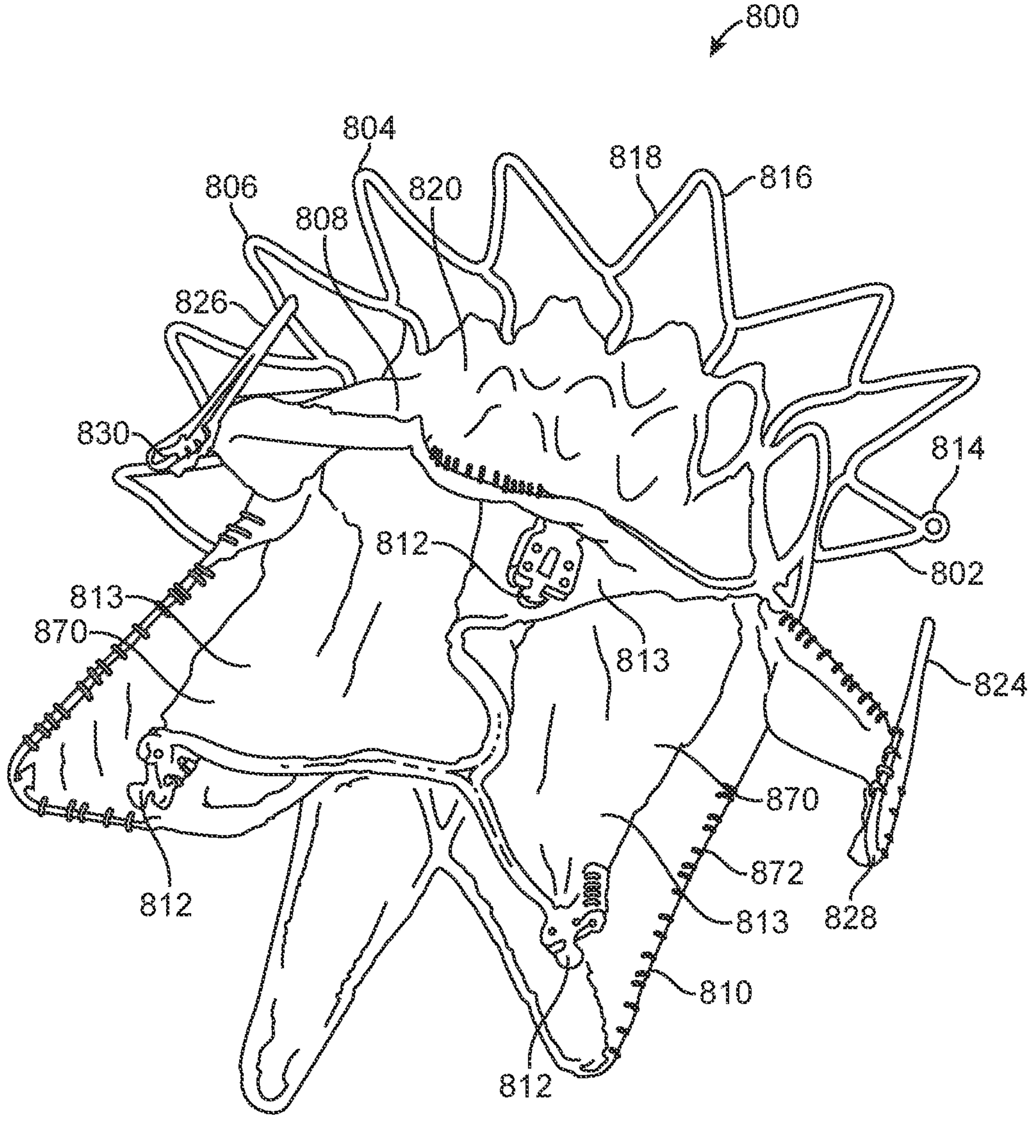
FIG. 9B illustrates a perspective view of the prosthetic valve in FIG. 8A from the ventricle.

FIG. 9B is a perspective view of the prosthetic mitral valve seen in FIG. 9A, as seen from the ventricle. The struts of the valve commissures are covered with the same material or a different material as the annular and ventricular regions as discussed above, thereby forming the tricuspid valve leaflets 813. FIG. 9B shows the valve in the closed configuration where the three leaflets are engaged with one another preventing retrograde blood flow. Commissure tabs 812 remain uncovered and allow the commissures to be coupled with a delivery device as will be explained below. The prosthetic valve in FIGS. 9A-9B may be sterilized so they are suitable for implantation in a patient using methods known in the art.

Figure 10:
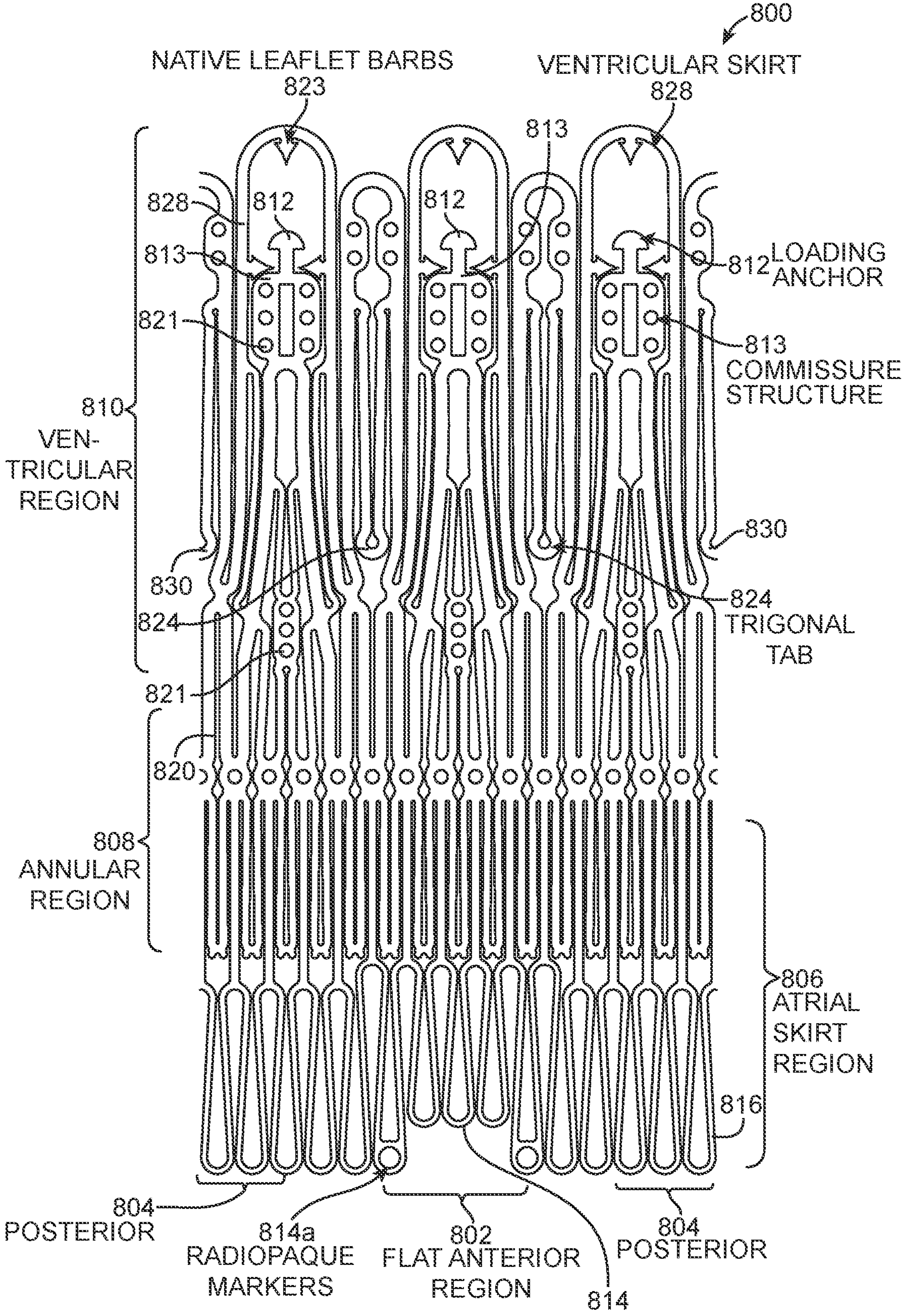
FIG. 10 illustrates the prosthetic valve of FIG. 8A uncovered and unrolled in a flat pattern.

FIG. 10 illustrates the prosthetic valve of FIG. 9A with the covering removed, and the remaining anchor unrolled and flattened out. The prosthetic valve 800 is formed from a plurality of interconnected struts. For example, the atrial skirt region 806 includes a plurality of interconnected struts that form a series of peaks and valleys. The flat anterior region 802 of the prosthetic valve has its peaks and valleys axially offset from those of the remaining portion of the atrial skirt, and this region becomes a part of the alignment element 814. Radiopaque markers 814*a* are disposed on either side of the offset peaks and valleys and help with visualization during implantation of the valve. An axially oriented connector joins the struts of the skirt region 806 with the struts of the annular region 808. The annular region is also comprised of a plurality of axially oriented and interconnected struts that form peaks and valleys. Connector struts couple struts of the annular region with the struts of the ventricular region 810. The ventricular region also includes a plurality of interconnected struts that form peaks and valleys. Additionally, the struts form the leaflet commissures 813, the ventricular skirt 828, as well as the trigonal and posterior tabs 824, 830. Suture holes 821 are disposed along the struts of the annular region as well as the ventricular region to allow attachment of a cover such as pericardium or a polymer such as Dacron or ePTFE. Optional barbs 823 are disposed along the ventricular skirt 828 to help anchor the prosthetic valve to adjacent tissue.

Commissure tabs or tabs 812 are disposed on the tips of the commissures 813 and may be used to releasably couple the prosthetic valve with a delivery system as will be described below. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

Once the flat anchor pattern has been formed by EDM, laser cutting, photochemical etching, or other techniques known in the art, the anchor is radially expanded into a desired geometry. The anchor is then heat treated using known processes to set the shape. Thus, the anchor may be loaded onto a delivery catheter in a collapsed configuration and constrained in the collapsed configuration with a constraining sheath. Removal of the constraining sheath will allow the anchor to self-expand into its unbiased pre-set shape. In other examples, an expandable member such as a balloon may be used to radially expand the anchor into its expanded configuration.

Delivery Systems

FIGS. 11-15C show a delivery apparatus 1124 fashioned to deliver a prosthetic mitral valve to the heart transapically. However, one of skill in the art will appreciate that the delivery system may be modified and relative motion of the various components adjusted to allow the device to be used to deliver a prosthetic mitral valve transseptally. The delivery apparatus is generally comprised of a handle 1101 that is the combination of a handle section 1102 and a handle section 1103 (best seen in FIG. 12), as well as a flexible tip 1110 that can smoothly penetrate the apex of the heart, and a sheath catheter 1109 which houses several additional catheters that are designed to translate axially and will be described in detail below.

The handle 1101 includes a female threaded Luer adaptor 1113 which connects to a Tuohy Borst adaptor 1114 in order to provide a hemostatic seal with a 0.035" diameter guide wire (not shown). The female threaded Luer adaptor 1113 is in threaded contact with the proximal section of the handle 1101 through a threaded port 1131 (best seen in FIG. 12).

Figure 11:
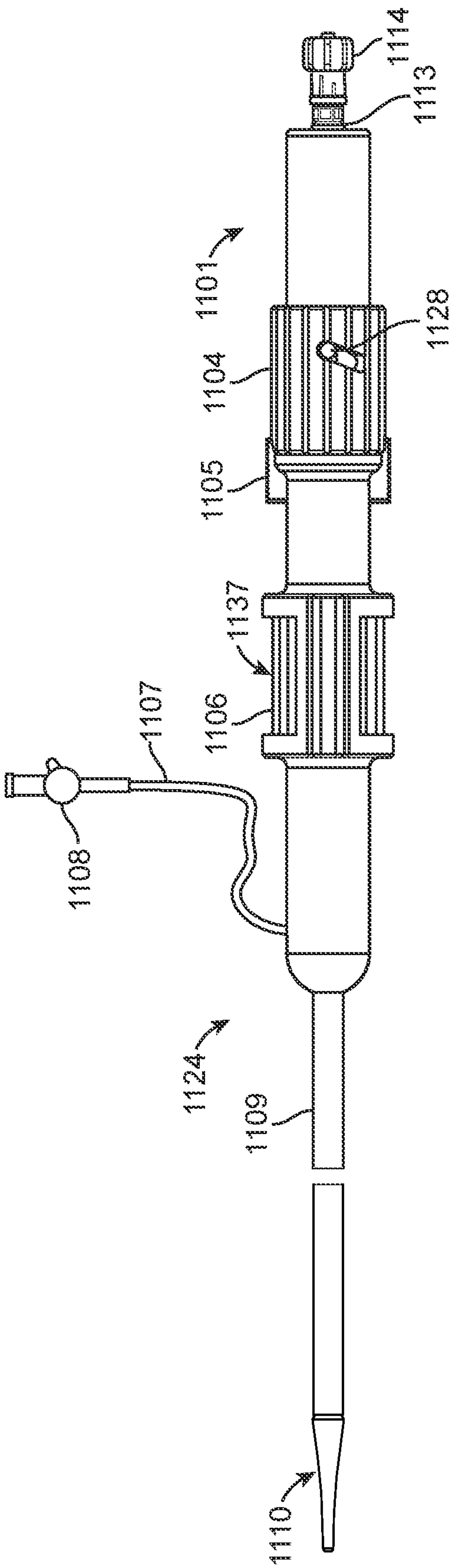
FIG. 11 is a side view of a delivery device for implantation of a prosthetic valve.

As can be seen in FIG. 11, the handle 1101 provides location for the control mechanisms used to position and deploy a prosthetic mitral valve. The handle 1101 provides housing for a thumbwheel 1106 that can be accessed through a window 1137 that appears on both the top and bottom of the handle 1101. The thumbwheel 1106 internally mates with a threaded insert 1115 (best seen in FIG. 12) that actuates the sheath catheter 1109, and the mechanics of this interaction will be explained in detail below.

FIG. 11 also shows a deployment thumbwheel 1104 that provides linear translation to a deployment catheter 1120 (best seen in FIG. 12) when turned, since the turning motion of the deployment thumbwheel 1104 acts as a power screw, pushing the peg 1128 forward and distally from the user. The mechanics behind the peg 1128 will be further detailed below. The thumbwheel lock 1105 provides a security measure against unwanted rotation of the deployment thumbwheel 1104 by acting as a physical barrier to rotation. In order to turn the deployment thumbwheel 1104 the user must push forward the thumbwheel lock 1105, disengaging it from two slots 1147 (seen in FIG. 12) in the deployment thumbwheel 1105.

As can also be seen in FIG. 11, a bleed valve 1108 and fluid line 1107 are connected to an internal mechanism in the distal portion of the handle 1101, which provides a hemostatic seal for the sheath catheter 1109. The details of this connection will be described below.

Figure 12:
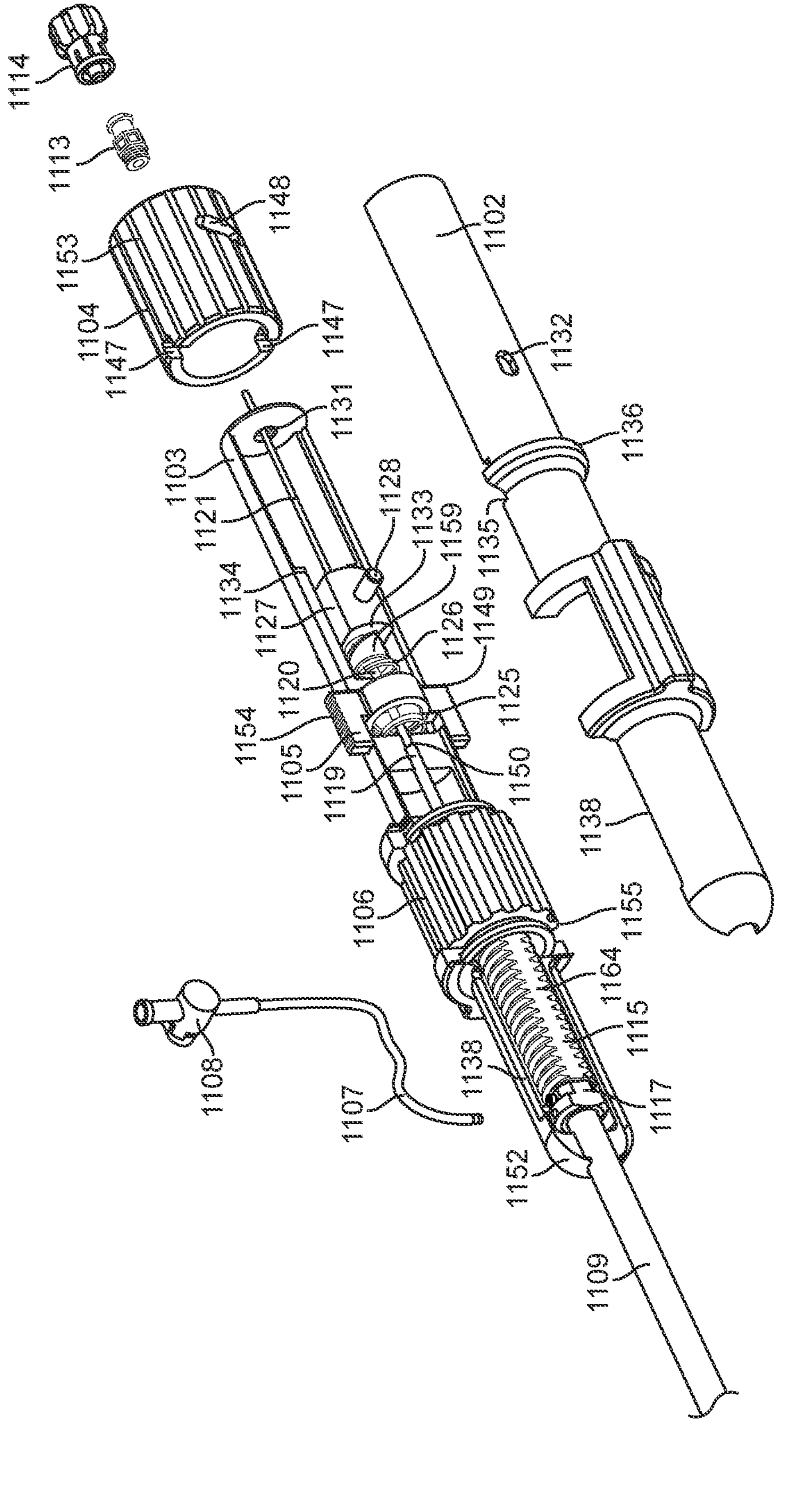
FIG. 12 is a partially exploded view of a proximal portion of the delivery device in FIG. 11.

Internal mechanics of the delivery apparatus 1124 are illustrated in detail in FIG. 12, and the following descriptions will reveal the interactions between individual components, and the manner in which those components combine in order to achieve a prosthetic heart valve delivery apparatus.

As seen in FIG. 12, a handle section 1103 and handle section 1102 combine to create a handle 1101 that forms the basis of the delivery apparatus 1124. In order to advance the sheath catheter 1109 during valve loading, or retract the sheath catheter 1109 during deployment, a rotatable thumbwheel 1106 is in threaded contact (internal threads 1129 seen in FIG. 14) with a threaded insert 1115 (external threads 1130 of FIG. 13) that translates linearly along the axis of the delivery apparatus, from a proximal position to a distal position. The sheath catheter 1109 is in mating contact with the threaded insert 1115 and is fastened through the use of a collar 1117 that aligns and mates the collar with the insert. The collar 1117 is fastened with screws 1116 (best seen in DETAIL A in FIG. 14) to the threaded insert 1115 and contains a fluid port 1142 (best seen in DETAIL A in FIG. 14) that provides location for the fluid line 1117 so that hemostasis can be maintained between the patient and delivery apparatus. An O-ring 1118 (best seen in DETAIL A in FIG. 14) seals the stationary catheter 1119 (best seen in FIG. 14) against the sheath catheter 1109. The fluid line 1107 also provides a means of visually locating the sheath catheter 1109 with respect to position, as a slot 1138 in the handle 1101 allows the fluid line 1107 to translate with the sheath catheter 1109 (through a hole 1151 (best seen in DETAIL A in FIG. 14) during operation, and this translation is highly visible. In order to prevent rotation of the threaded insert during translation, a flat face 1164 has been machined onto both sides of the threaded insert 1115. The flat faces 1164 remain in contact with bosses 1139 and 1140 that are located on both handle section 1102 and handle section 1103 so that the bosses 1139 and 1140 act to grip the threaded insert 1115 and prevent rotation. A textured pattern 1155 allows the user to easily turn the thumbwheel 1106 in the surgical field. Detents 1141 (best seen in FIG. 14) locate flanges 63 (seen in FIG. 14) on the thumbwheel 1116 in order to allow for rotation.

The manner in which individual catheters (there are four catheters) move with respect to each other is illustrated in FIG. 12. Sheath catheter 1109 provides housing for the stationary catheter 1119, which in turn provides housing for the movable hub catheter 1120. The hub catheter 1120 translates linearly with respect to the nose catheter 1121 which can also be translated with respect to each previous catheter, and the handle 1101. The stationary catheter 1119 is mated to a handle section 1103 in an internal bore 1150 which also forms a seal between the stationary catheter 1119 and the hub catheter 1120. The distal portion of the stationary catheter 1119 is formed in the shape of a bell 1122 (see DETAIL A in FIG. 15A) which acts as a housing to retain the hub capture 1123 (seen in DETAIL A in FIG. 15A).

As previously stated a thumbwheel lock 1105 prevents rotation of the deployment thumbwheel 1104. In order to provide a seating force that keeps the thumbwheel lock 1105 in a locked position until manipulated, a spring 1125 is housed in an internal bore 62 (best seen in FIG. 14) and abuts against a shoulder 1161 (best seen in FIG. 14) that is located inside the thumbwheel lock 1105. This spring 1125 maintains the leading edge 1149 of the thumbwheel lock 1105 in a locked position within the two slots 1147 of the deployment thumbwheel 1104. Gripping texture 1154 is provided on the thumbwheel lock 1105 for ease of use. In order to locate and retain the thumbwheel lock 1105 inside of the handle 1101, a slot 1135 has been provided in both a handle section 1102 and a handle section 1103.

As shown in FIG. 12, a sliding block 1127 is housed inside of flat parallel faces 1134 which appear on the inside of the handle 1101. This sliding block 1127 is in mating contact with hub catheter 1120 and is the physical mechanism that linearly actuates the catheter. A spring 1126 is mounted on an external post 1159 and abuts against a shoulder 1133 that is located on the distal end of the sliding block 1127. This spring 1126 forces a peg 1128 (located inside a thru-hole 1156 of FIG. 14) into contact with the proximal edge of an angled slot 1148 that is cut into the deployment thumbwheel 1104. The deployment thumbwheel 1104 is contained between a shoulder 1136 and a snap ring (not shown), both of which are features of the handle 1101. Gripping texture 1153 on the deployment thumbwheel 1104 allows the user to easily rotate the thumbwheel in a clockwise direction, actuating the peg 1128 to ride distally along the slot 1148 and move the sliding block 1127, which pushes the hub catheter 1120 and hub 1123 (best seen in DETAIL A of FIG. 15A) forward and out of the bell 1122 (seen in DETAIL A of FIG. 15A). A slot 1132 appears in a handle section 1102 and a handle section 1103 and prevents the peg 1128 from translating beyond a desired range.

A nose catheter 1121 extends from a Tuohy Borst adaptor 1114 on the proximal end of the handle 1101, and internally throughout the handle and the respective catheters (sheath catheter 1109, stationary catheter 1119, and hub catheter 1120), terminating inside the rigid insert 1112 (seen in FIG. 15A) of the flexible tip 1110 (seen in FIG. 15A) that abuts with the distal end of the sheath catheter 1109.

Figure 13:
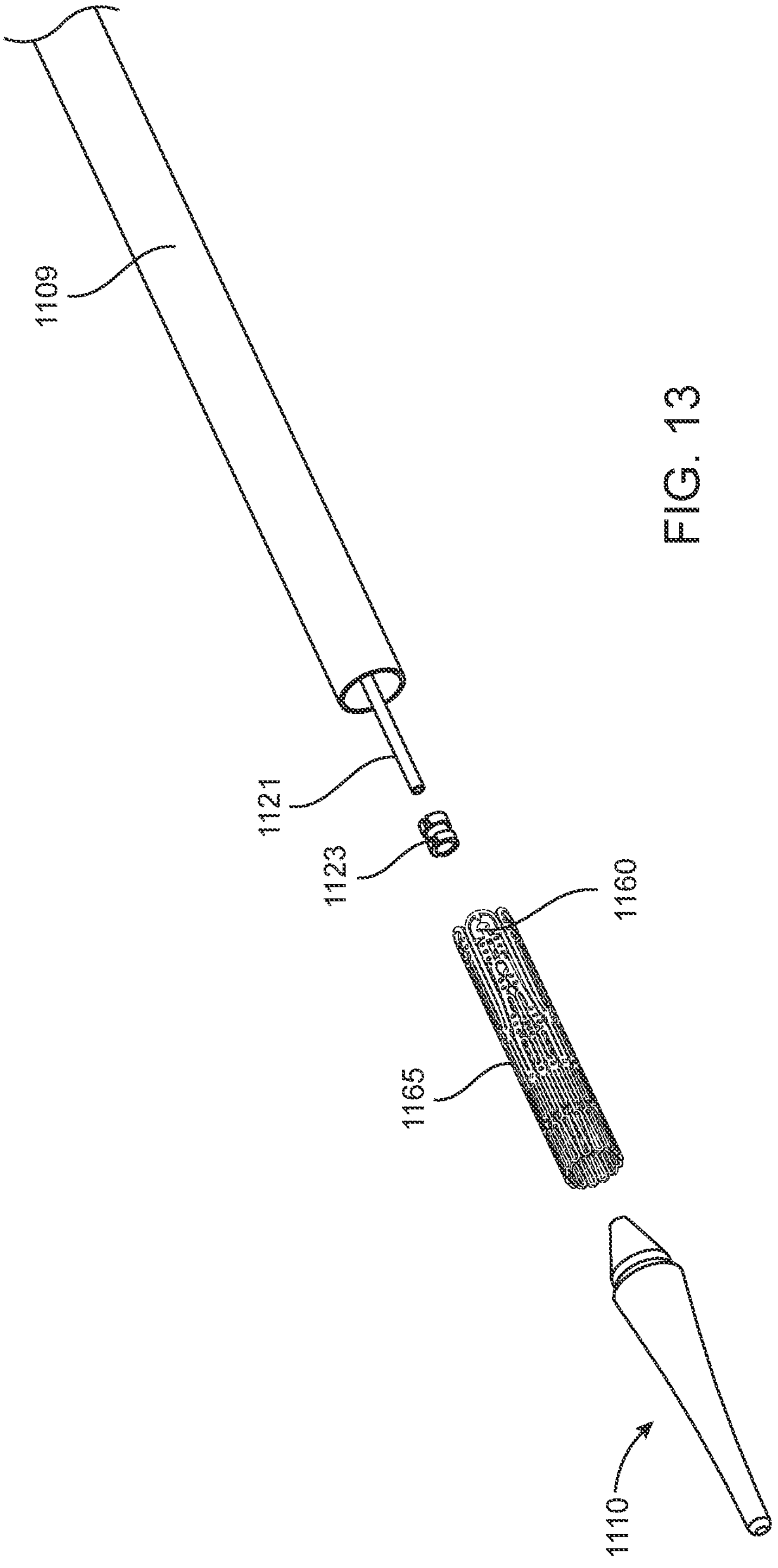
FIG. 13 is a partially exploded view of a distal portion of the delivery device in FIG. 11.
Figure 14:
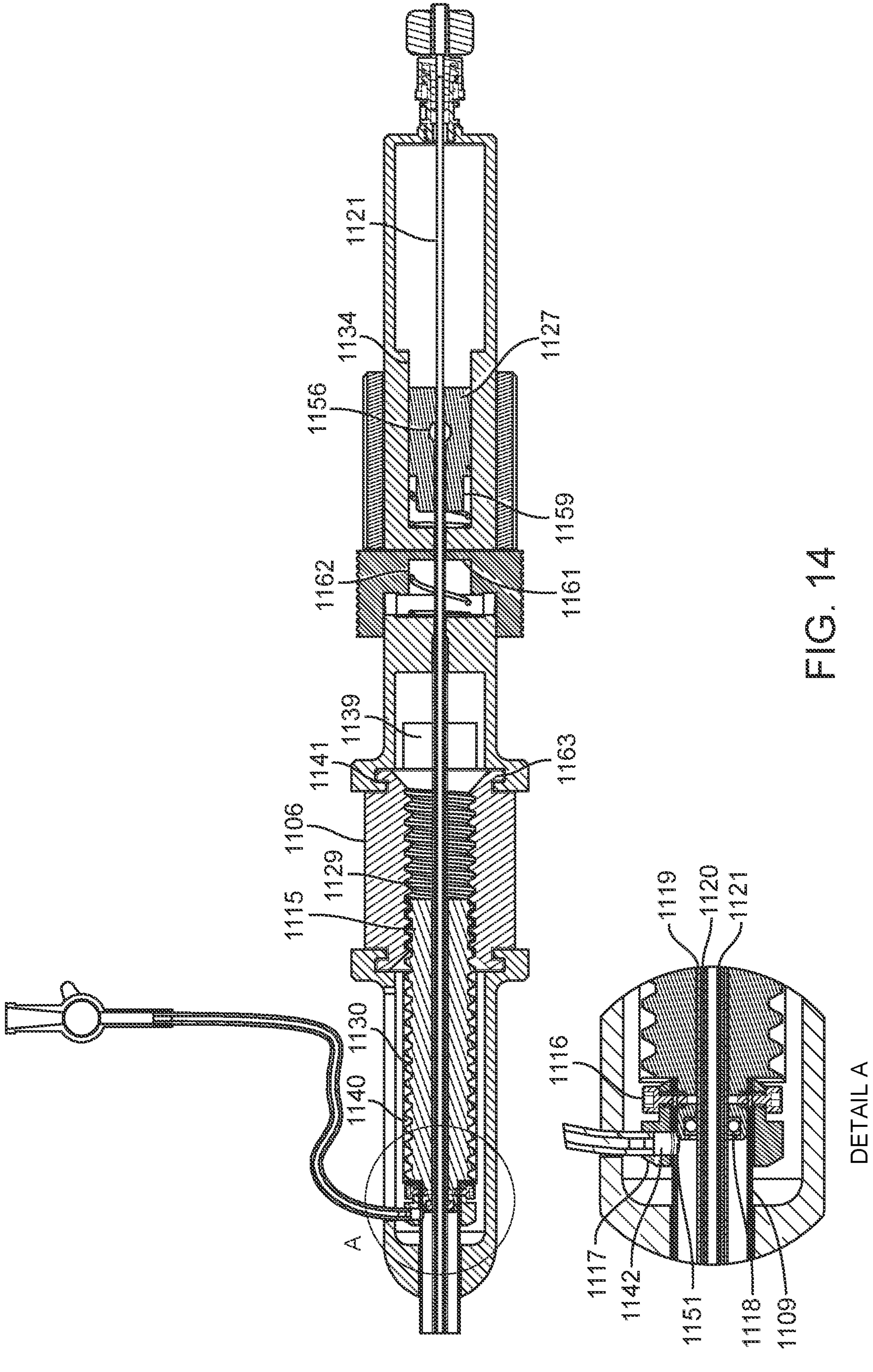
FIG. 14 is a cross-section of a proximal portion of the delivery device in FIG. 11.

FIG. 13 displays an exploded view of the tip section of the delivery apparatus 1124, and shows the relation between prosthetic mitral valve 1165 and the internal and external catheters. When crimped and loaded, the prosthetic mitral valve 1165 is encased between the internal surface of the sheath catheter 1109 and the external surface of the nose catheter 1121. In order to capture and anchor the prosthetic mitral valve 1165 within the delivery apparatus 1124, three commissure tabs 1160 (circumferentially spaced at about 120 degrees apart) appearing on the proximal end of the prosthetic mitral valve 1165 provide points of contact between the valve and three slots 1143 (seen in FIG. 15A) that are machined into the outer surface of the hub 1123 (circumferentially spaced at about 120 degrees apart). After first advancing the hub catheter 1120 (FIG. 15A) by rotating the deployment thumbwheel 1104 (seen in FIG. 12) clockwise, the three commissure tabs 1160 can be captured within the three slots 1143 (seen in FIG. 15A). The hub 1123 can then be retracted into the bell 1122 by releasing the deployment thumbwheel 1104 (seen in FIG. 12). In this position the prosthetic mitral valve 1165 is anchored to the delivery apparatus 1124, and further crimping of the valve will allow the sheath catheter 1109 to be advanced over the valve.

Figure 15A:
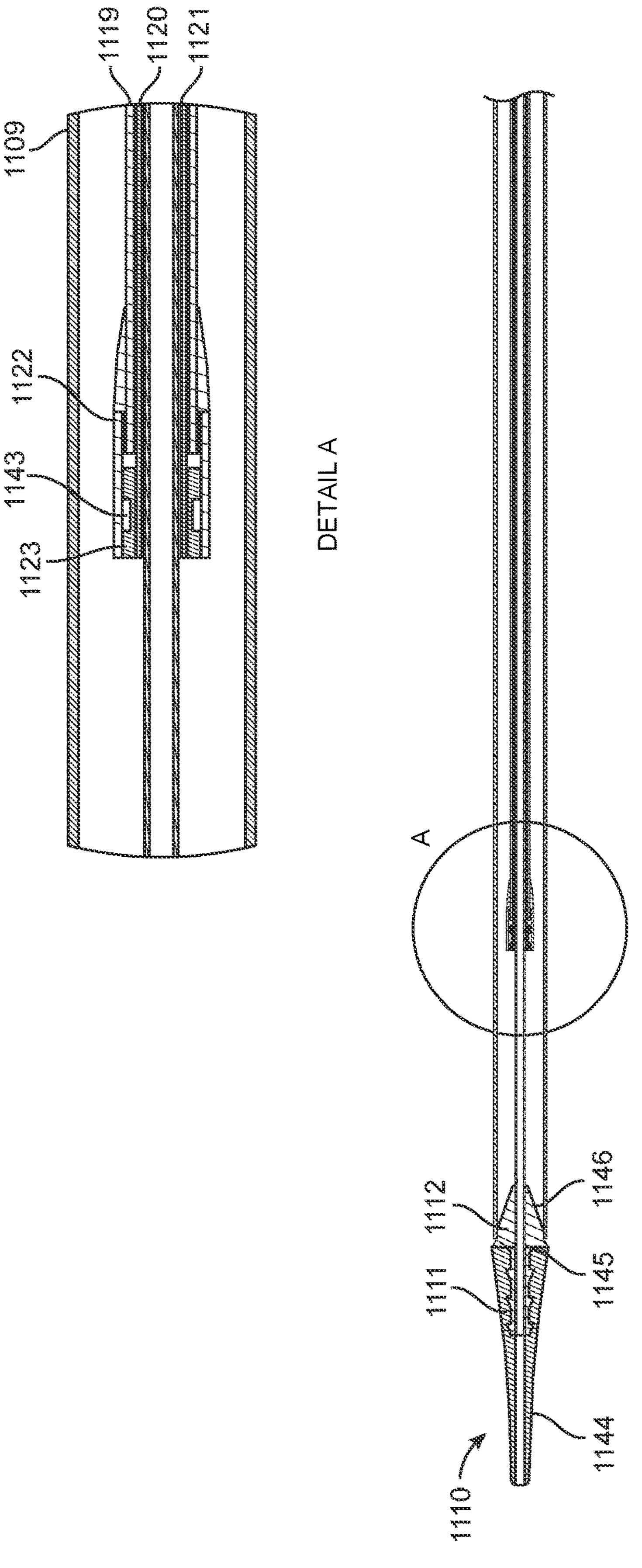
FIGS. 15A-15C are cross-sectional views of a distal portion of the delivery device in FIG. 11.
Figure 15B:
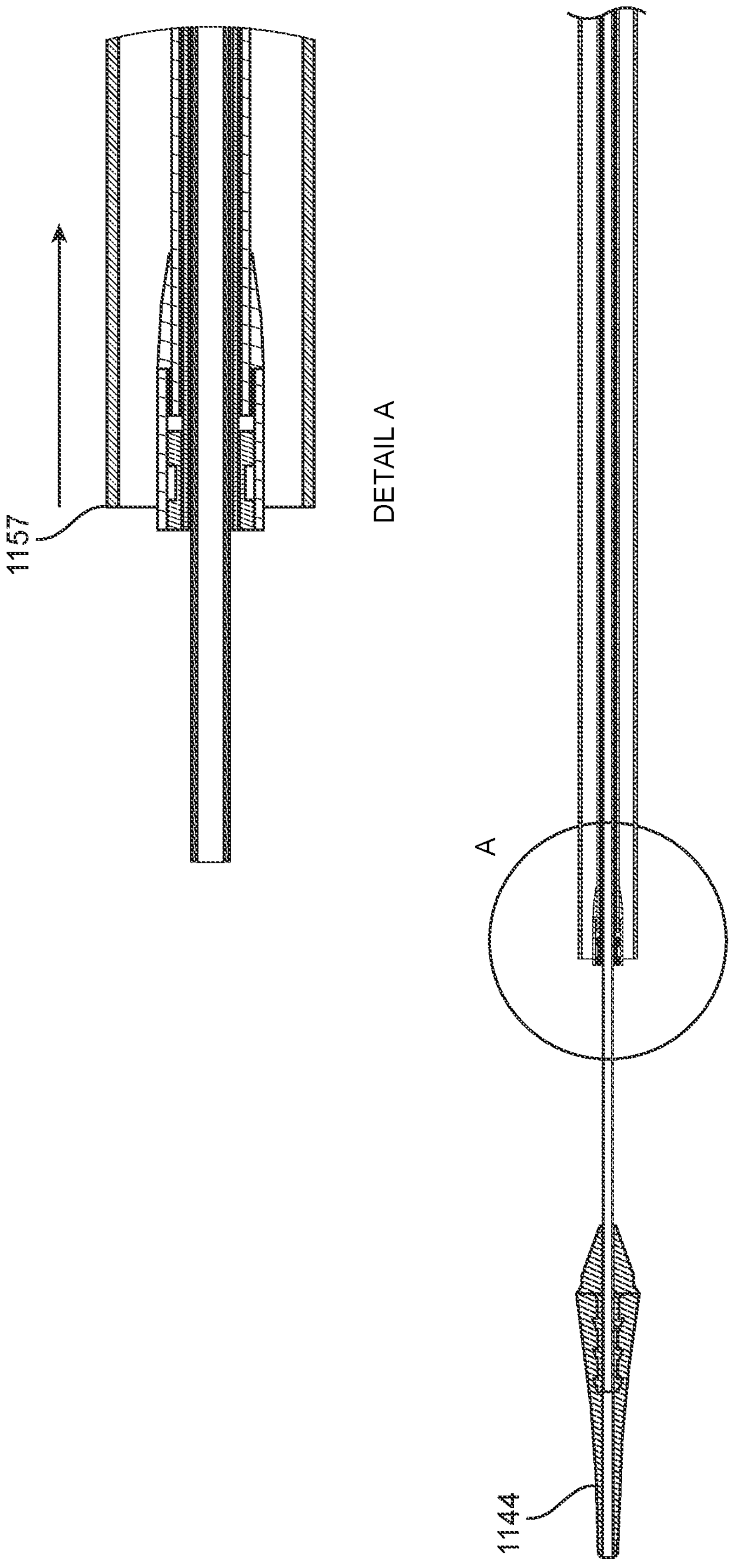
Figure 15C:
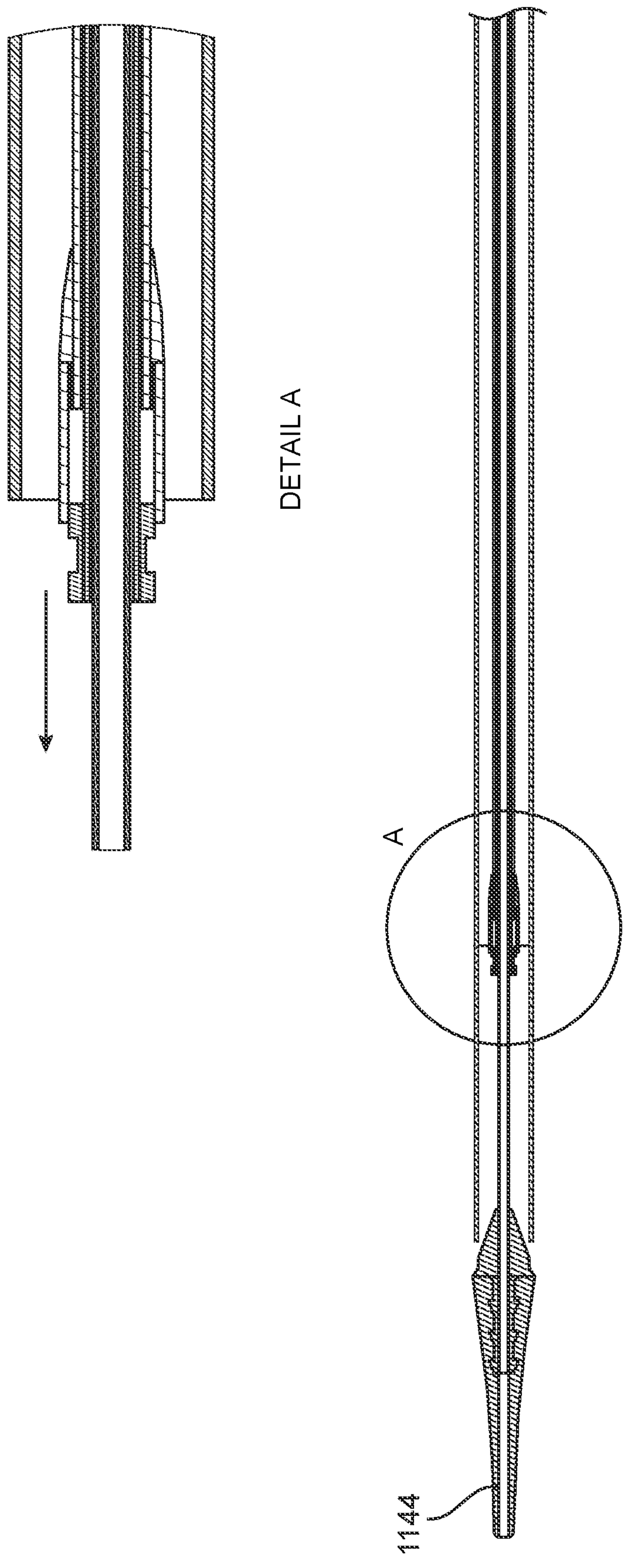

FIGS. 15A-15C further detail the manner in which loading of the prosthetic mitral valve 1165 (seen in FIG. 13) into the delivery apparatus 1124 can be achieved. Initially, the flexible tip 1110 is abutted against the distal edge 1157 of the sheath catheter 1109. The flexible tip 1110 is comprised of a rigid insert 1112, and a soft and flexible tip portion 1111 which is over-molded onto the rigid insert 1112. The shoulder 1145 and tapered face 1146 of the rigid insert 1112 act to guide and locate the distal edge 1157 of the sheath catheter 1109, so that the catheter may rest against and be stiffened by the flexible tip 1110, and be more easily introduced into the apex of the heart.

An initial position from which loading can be achieved is illustrated in FIG. 15A. As a first step in the loading of a prosthetic mitral valve 1165 (seen in FIG. 13) into the delivery apparatus 1124, the sheath catheter 1109 is withdrawn by rotation of the thumbwheel 1106 in a clockwise direction. The distal edge 1157 of the sheath catheter 1109 is retracted until it passes the distal edge of the bell 1122, as illustrated in DETAIL A of FIG. 15B. As a second step in the loading of a prosthetic mitral valve 1165 (seen in FIG. 13) into the delivery apparatus 1124, the hub 1123 is advanced from beneath the bell 1122 by clockwise turning of the deployment thumbwheel 1104 (seen in FIG. 12), as illustrated in DETAIL A of FIG. 15C. The deployment thumbwheel may only be turned once the thumbwheel lock 1105 (see FIG. 12) has been set in the forward position, disengaging it from contact with the thumbwheel. Advancement of the hub 1123 uncovers three slots 1143 into which three commissure tabs 1160 of the prosthetic mitral valve 1165 (seen in FIG. 13) will fit and be anchored. After anchoring of the commissure tabs 1160 into the slots 1143 by retraction of the hub 1123 has been achieved, a third step in the loading of a prosthetic mitral valve 1165 (seen in FIG. 13) into the delivery apparatus 1124 may be performed. The prosthetic mitral valve 1165 (seen in FIG. 13) can be crimped down to a minimum diameter by a loading mechanism (not shown), and then the sheath cannula 1109 can be advanced forward so as to cover the valve, by rotation of the thumbwheel 1106 in a counter-clockwise direction. The delivery apparatus 1124 and prosthetic mitral valve 1165 are then ready for deployment.

FIGS. 16-19B illustrate another example of a delivery device for implanting a prosthetic valve in the heart transapically. However, one of skill in the art will appreciate that the delivery system may be modified and relative motion of the various components adjusted to allow the device to be used to deliver a prosthetic transseptally. The delivery apparatus is generally comprised of a handle 1601 that is the combination of two halves (1610 and 1635), as well as a tip 1603 that can smoothly penetrate the apex of the heart, and a flexible sheath 1602 which is comprised of concentric catheters that are designed to translate axially and will be described in detail below.

The handle 1601 includes a handle cap 1611 which connects to a female threaded Luer adaptor 1612 in order to provide a sealable exit for a 0.035" diameter guide-wire (not shown). The handle cap 1611 is attached to the handle 1601 with threaded fasteners 1613. The female threaded Luer adaptor 1612 is in threaded contact with the handle cap 1611 through a tapped port, and when fully inserted squeezes against an O-ring (1636 best seen in FIG. 18) which seals against the outer diameter of a guide-wire catheter (1621 best seen in FIG. 18).

Figure 17:
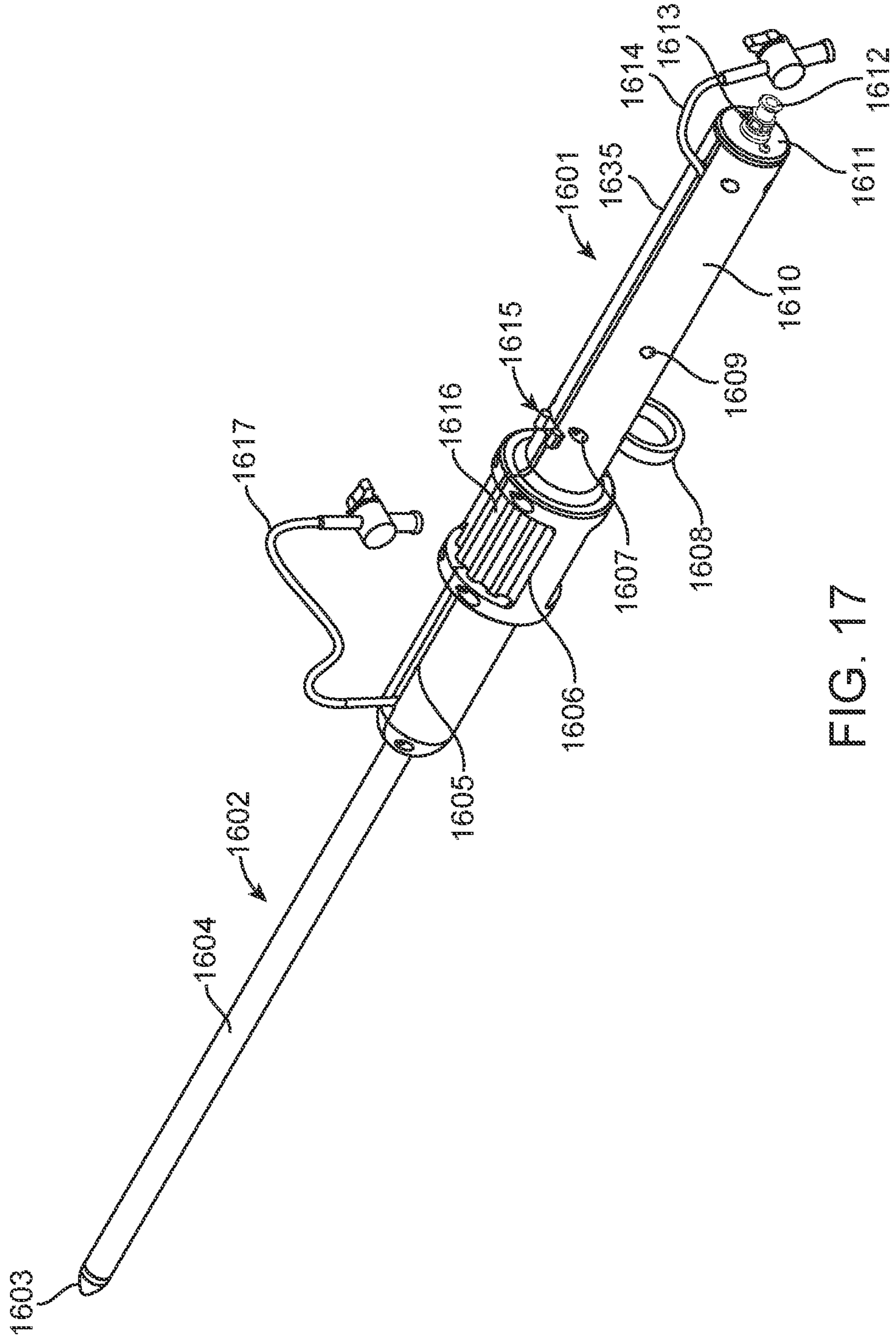
FIG. 17 is a perspective view of the delivery device in FIG. 16.

As can be seen in FIG. 17, the handle 1601 provides location for the control mechanisms used to position and deploy a prosthetic mitral valve. The handle 1601 provides housing for a thumbwheel 1616 that can be accessed through a window 1606 that appears on both the top and bottom of the handle 1601. The thumbwheel 1616 internally mates with a threaded insert (1627 in FIG. 18) that actuates the sheath catheter 1604, and the mechanics of this interaction will be explained in detail below.

Figure 18:
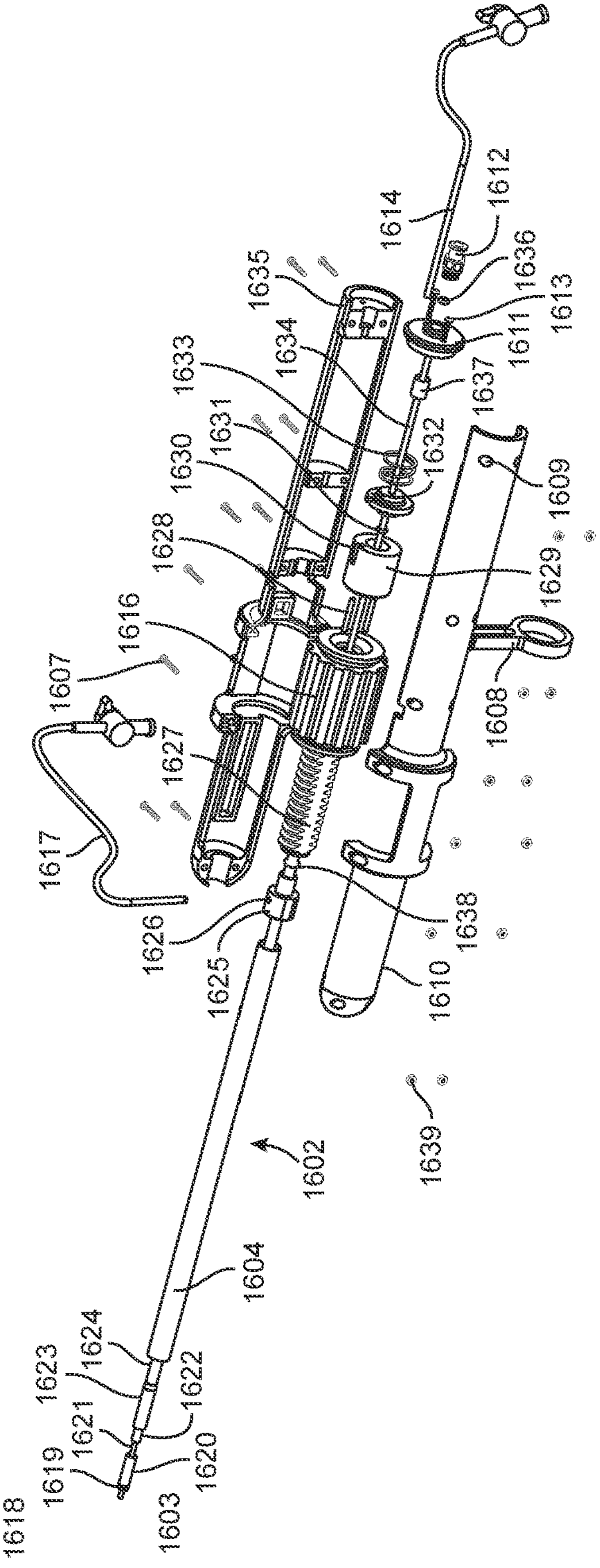
FIG. 18 is a partially exploded view of the delivery device in FIG. 16.

FIG. 17 also shows a first hemostasis tube 1617 that is inserted internally through a slot 1605, and that mates with a first hemo-port through a hole (1625 and 1626 in FIG. 18 respectively). The first hemostasis tube 1617 allows for fluid purging between internal catheters. The position of the first hemostasis tube 1617 along the slot 1605 provides a visual cue as to the position of the sheath catheter 1604, and relative deployment phase of a prosthetic mitral valve (not shown). The relationship between the connection of the first hemostasis tube 1617 and the sheath catheter 1604 will be described below.

As can also be seen in FIG. 17, a second hemostasis tube 1614 is inserted into the handle 1601 and mated to a second hemo-port (1629 in FIG. 18) in order to allow fluid purging between internal catheters, and details of this insertion will be described below. Finally, a pin lock 1608 provides a security measure against premature release of a prosthetic mitral valve, by acting as a physical barrier to translation between internal mechanisms. Pin lock prongs 1615 rely on spring force to retain the pin lock 1608 in the handle 1601, and a user must first pull out the pin lock 1608 before final deployment of a prosthetic valve.

FIG. 17 also shows how the handle 1601 is fastened together by use of threaded fasteners and nuts (1607 and 1639 of FIG. 18 respectively), and countersunk locator holes 1609 placed throughout the handle length.

Internal mechanisms of the delivery system are illustrated in detail in FIG. 18, and the following descriptions will reveal the interactions between individual components, and the manner in which those components combine in order to create a system that is able to deliver a prosthetic mitral valve transapically or by other routes.

As seen in FIG. 18, the flexible sheath 1602 is comprised of four concentrically nested catheters. In order from smallest to largest in diameter, the concentrically nested catheters will be described in detail. The innermost catheter is a guide-wire catheter 1621 that runs internally throughout the entire delivery system, beginning at the tip 1603 and terminating in the female threaded Luer adaptor 1612. The guide-wire catheter 1621 is composed of a lower durometer, single lumen Pebax extrusion and is stationary. It provides a channel through which a guidewire (not shown) can communicate with the delivery system. The next catheter is the hub catheter 1622 which provides support for the hub 1620 and is generally comprised of a higher durometer, single lumen PEEK extrusion. The hub catheter 1622 is in mating connection with both the hub 1622 at the distal end, and a stainless steel support rod 1634 at the proximal end. The stainless steel support rod 1634 is held fixed by virtue of a stopper 1637 that is encased in the handle 1601. The hub catheter 1622 is stationary, and provides support and axial rigidity to the concentrically nested catheters. The next catheter is the bell catheter 1624, which provides housing to the hub 1620 and is generally comprised of a medium durometer, single lumen Pebax extrusion, including internal steel braiding and lubricious liner, as well as a radiopaque marker band (not shown). The bell catheter 1624 translates axially, and can be advanced and retracted with respect to the hub 1620. The bell catheter 1624 is in mating connection with the second hemo-port 1629 at the proximal end, and hemostasis between the bell catheter 1624 and the stainless steel support rod 1634 can be achieved by purging the second hemostasis tube 1614. The bell catheter 1624 is bumped up to a larger diameter 1623 on the distal end in order to encapsulate the hub 1620. The outermost and final catheter is the sheath catheter 1604 which provides housing for a prosthetic mitral valve (not shown), and which is able to penetrate the apex of the heart (not shown), by supporting and directing a tip 1603 and assisting in the dilation of an incision in the heart wall muscle. The sheath catheter 1604 is generally comprised of a medium durometer, single lumen Pebax extrusion, including internal steel braiding and lubricious liner, as well as radiopaque marker band (not shown). The sheath catheter 1604 translates axially, and can be advanced and retracted with respect to the hub 1620. The sheath catheter 1604 is in mating connection with the first hemo-port 1625 at the proximal end, and hemostasis between the sheath catheter 1604 and the bell catheter 1624 can be achieved by purging the first hemostasis tube 1617.

As seen in FIG. 18, the proximal end of the sheath catheter 1604 is in mating contact with a first hemo-port 1625. The first hemo-port is in mating contact with a threaded insert 1627, and an O-ring 1638, which is entrapped between the first hemo-port 1625 and the threaded insert 1627 in order to compress against the bell catheter 1624, creating a hemostatic seal. As the thumbwheel 1616 is rotated, the screw insert 1627 will translate, and the sheath catheter 1624 can be retracted or advanced by virtue of attachment. In order to provide adequate stiffness to dilate heart wall tissue, the distal edge of the sheath catheter 1604 will abut against a shoulder 1618 located on the tip 1603. This communication allows the tip 1603 to remain secure and aligned with the sheath catheter 1604 during delivery, and creates piercing stiffness.

FIG. 18 also details the mechanism through which the bell catheter 1624 can be retracted or advanced with respect to the hub 1620. The thumbwheel 1616 can be rotated to such an extent that the screw insert 1627 will be brought into contact with two pins 1628 that are press fit into the second hemo-port 1629. As the bell catheter 1624 is in mating contact with the second hemo-port 1629, further rotation of the thumbwheel 1616 will cause the second hemo-port 1629 to translate and press against a spring 1633 by virtue of connection to a second hemo-port cap 1632. This advancement will cause the bumped larger diameter section 1623 of the bell catheter 1624 to be retracted from the hub 1620. As the thumbwheel 1616 is rotated in the opposite direction, restoring force produced by the spring 1633 will cause the second hemo-port 1629 to be pushed in the opposite direction, drawing the bumped larger diameter section 1623 of the bell catheter 1624 back over the hub 1620, an action that is necessary during the initial loading of a valve prosthesis.

FIG. 18 further details the manner in which hemostasis is achieved between the stainless steel support rod 1634 and the bell catheter 1624. An O-ring 1631 is compressed between the second hemo-port 1629 and the second hemo-port cap 1632, creating a seal against the stainless steel support rod 1634. Hemostasis between the bell catheter 1624 and the stainless steel support rod 1634 can be achieved by purging the second hemostasis tube 1614, which is in communication with the void to be purged through a slot and hole 1630.

Figure 19A:
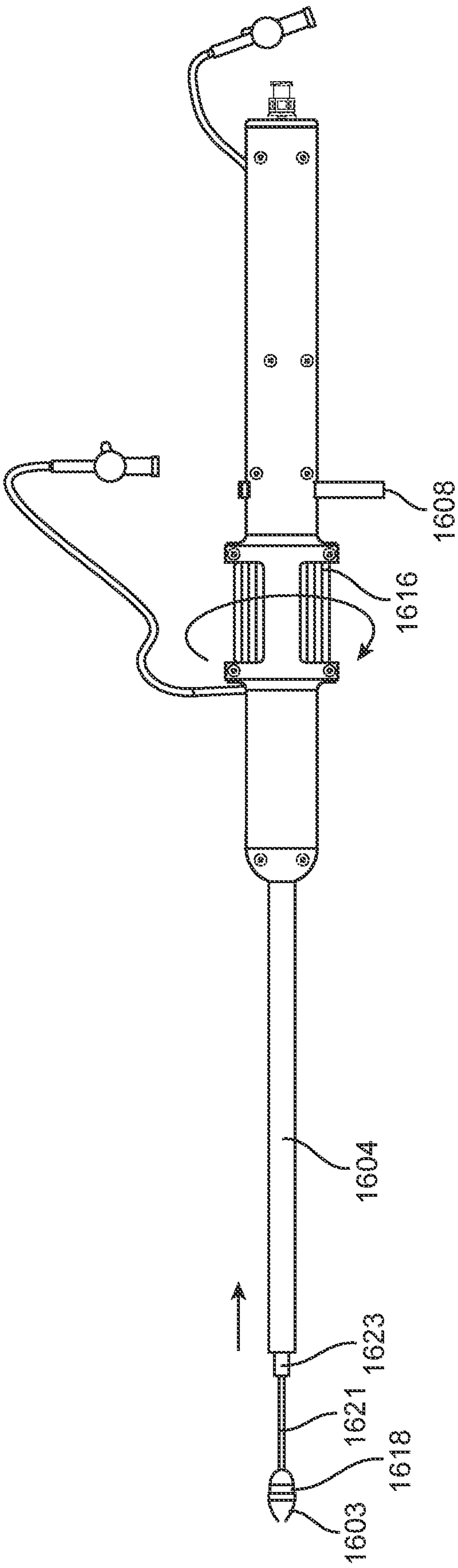
FIGS. 19A-19B are side views of the delivery device in FIG. 16 during various stages of operation.
Figure 19B:
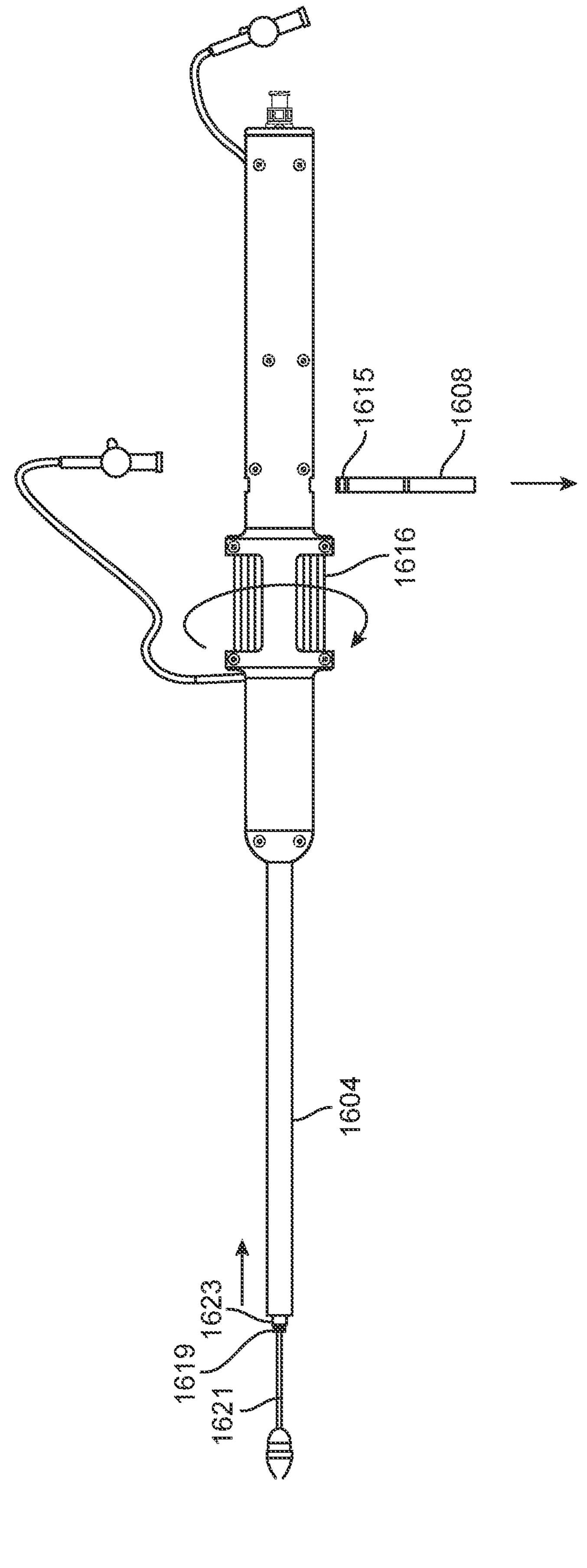

The deployment process and actions necessary to activate the mechanisms responsible for deployment are detailed in FIGS. 19A-19B. When performed in the reverse order, these actions also necessitate the first loading of a valve (not shown) prior to surgery.

As seen in FIG. 19A, manipulation of the thumbwheel 1616 will provide translational control of the sheath catheter 1604. In order to effect the deployment of a heart valve (not shown), the user must withdraw the sheath catheter 1604 from contact with the shoulder 1618 of the tip 1603 until it passes the larger diameter section 1623 of the bell catheter 1624. A heart valve (not shown) will reside concentrically above the guide-wire catheter 1621 in the position indicated by the leader for 1621 in FIG. 19A, similarly as to the example illustrated in FIG. 13. The sheath catheter 1604 can be withdrawn until the screw insert 1627 comes into contact with the pin lock 1608. The pin lock 1608 must then be removed before further travel of the screw insert 1627 can be achieved.

As seen in FIG. 19B, the pin lock 1608 is removed from the handle 1601 in order to allow further translation of the sheath catheter 1604. When the sheath catheter 1604 is fully retracted, the larger diameter section 1623 of the bell catheter 1624 is also fully retracted, which completely frees the heart valve (not shown) from the delivery system. Three hub slots 1619, spaced circumferentially at about 120 degrees from each other provide the anchoring mechanism and physical link between delivery system and heart valve. Once the larger diameter section 1623 of the bell catheter 1624 has been withdrawn, the hub slots 1619 become uncovered which allows the heart valve anchor (not shown) to fully expand.

Figure 16:
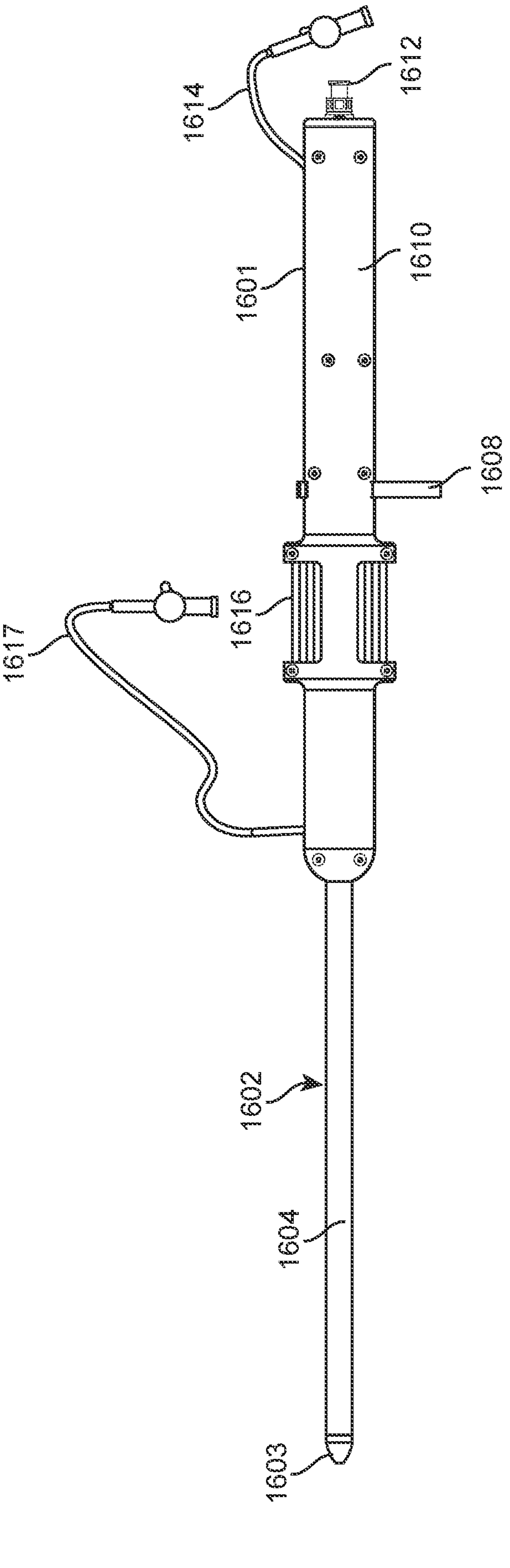
FIG. 16 is a side view of another example of a delivery device for implantation of a prosthetic valve.
Figure 20:
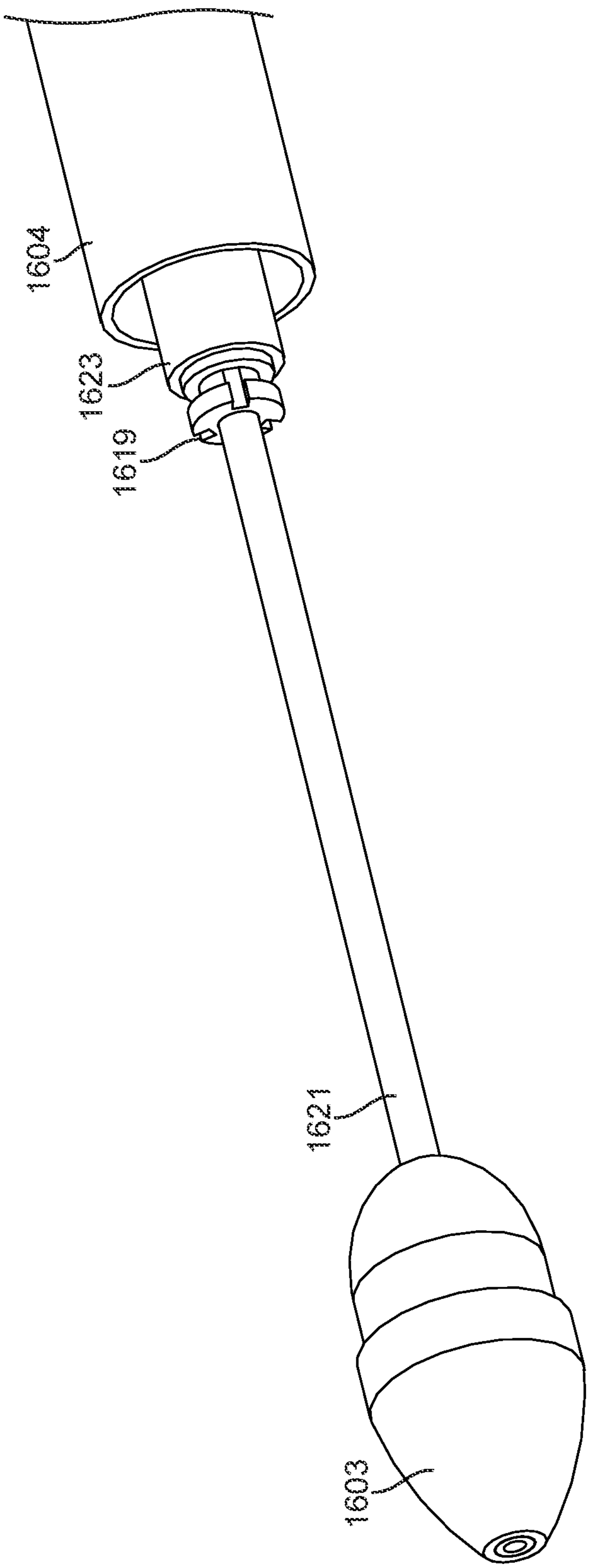
FIG. 20 illustrates a distal portion of the delivery device in FIG. 16 that is adapted to engage a portion of a prosthetic valve.

FIG. 20 illustrates a distal portion of the delivery device in FIG. 16. Three hub slots 1619 are slidably disposed distally relative to the large diameter tip 1623 of bell catheter 1624. These slots allow engagement with a prosthetic valve. The valve may be releasably held by the slots by disposing the commissure tabs or tabs 812 of the prosthetic valve into slots 1619 and then retracting the slots 1619 under tip 1623 of bell catheter 1624. The prosthetic valve may be released from the delivery catheter by advancing the slots distally relative to the bell catheter so that the loading anchors or tabs 812 may self-expand out of and away from slots 1619 when the constraint of tip 1623 on bell catheter 1624 has been removed.

Figure 21:
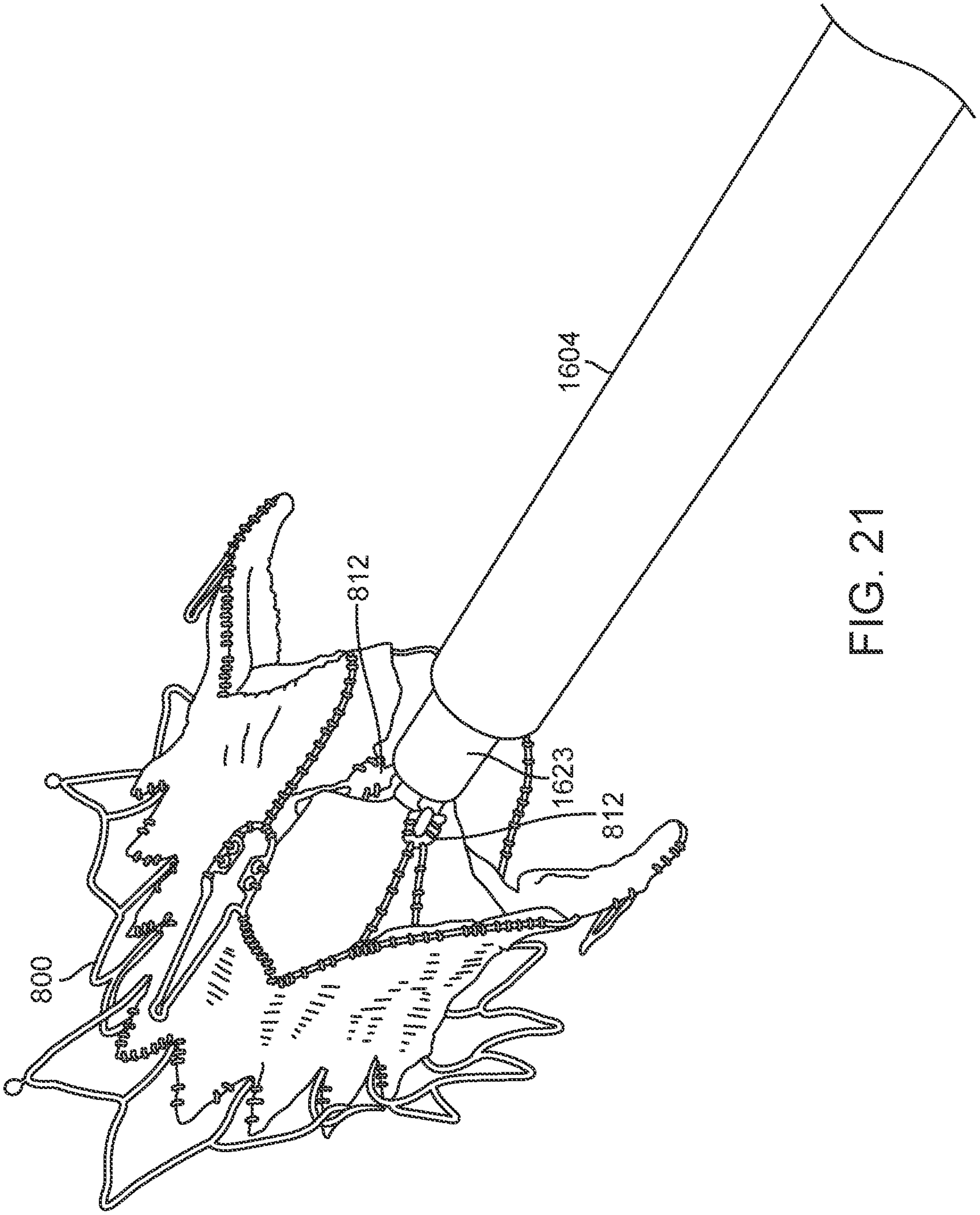
FIG. 21 illustrates engagement of the delivery device in FIG. 16 with the prosthetic valve of FIG. 8A.

FIG. 21 illustrates a prosthetic mitral valve 800 (as discussed above with reference to FIG. 8A) with the anchor tabs 812 disposed in the hub slots (not visible), and bell catheter 1623 advanced thereover. Thus, even though most of the prosthetic valve 800 has self-expanded into its expanded configuration, the valve commissures remain in a collapsed configuration with the tabs 812 captured in slots

1619. Once the constraint provided by bell catheter 1623 has been removed from the slots 1619, the tabs 812 may self-expand out of slots 1619, the commissures will open up to their unbiased position. The prosthetic valve is then disconnected and free from the delivery device.

Transapical Delivery Methods

Figure 22A:
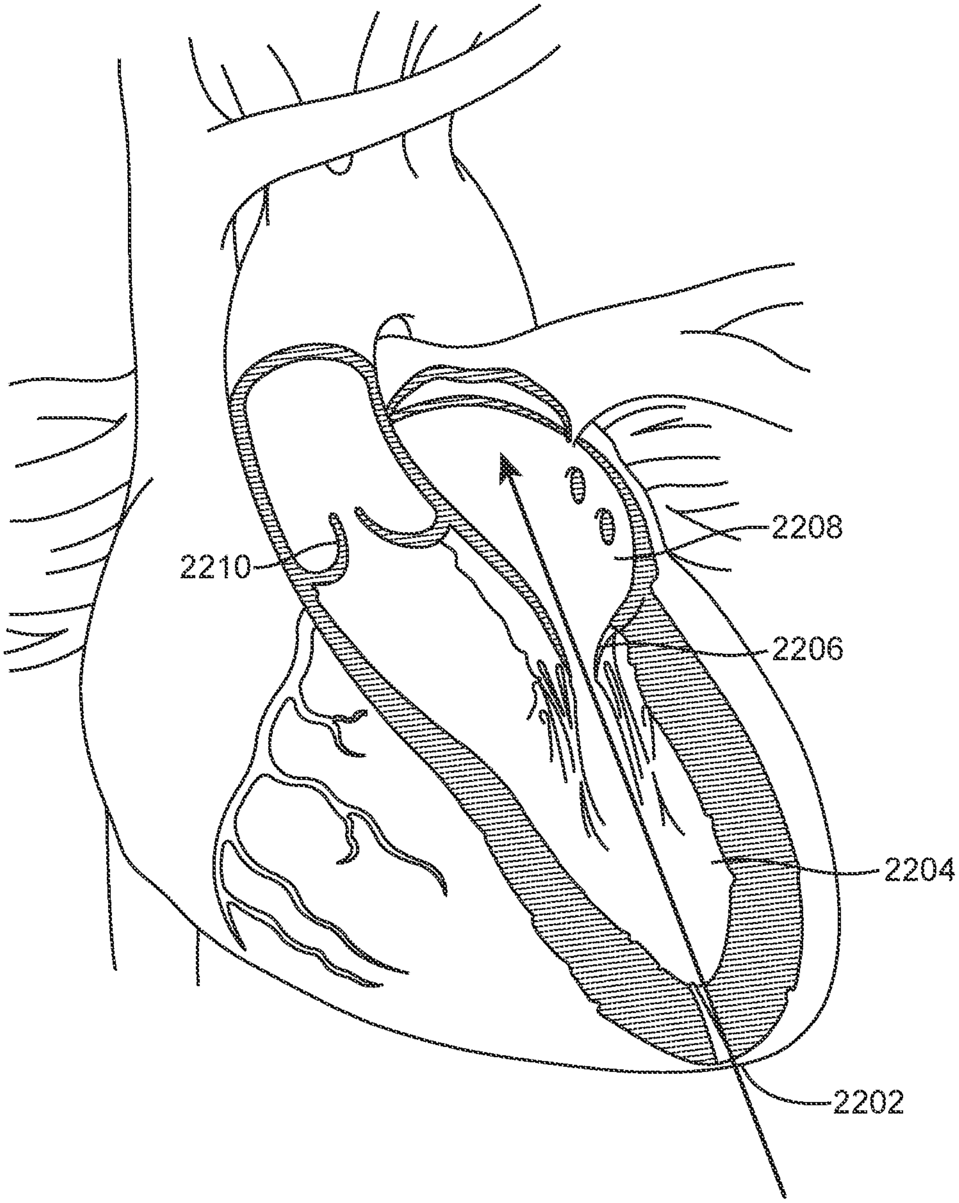
FIGS. 22A-22G illustrate an example of a method of transapically delivering a prosthetic mitral valve.

FIGS. 22A-22G illustrate an example of a method of transapically delivering a prosthetic mitral valve. This example may use any of the prosthetic valves described herein, and may use any of the delivery devices described herein. FIG. 22A illustrates the general transapical pathway that is taken with entry into the heart at the apex 2202, through the left ventricle 2204, across the mitral valve 2206 and into the left atrium 2208. The aortic valve 2210 remains unaffected. Transapical delivery methods have been described in the patent and scientific literature, such as in International PCT Publication No. WO2009/134701, the entire contents of which are incorporated herein by reference.

Figure 22B:
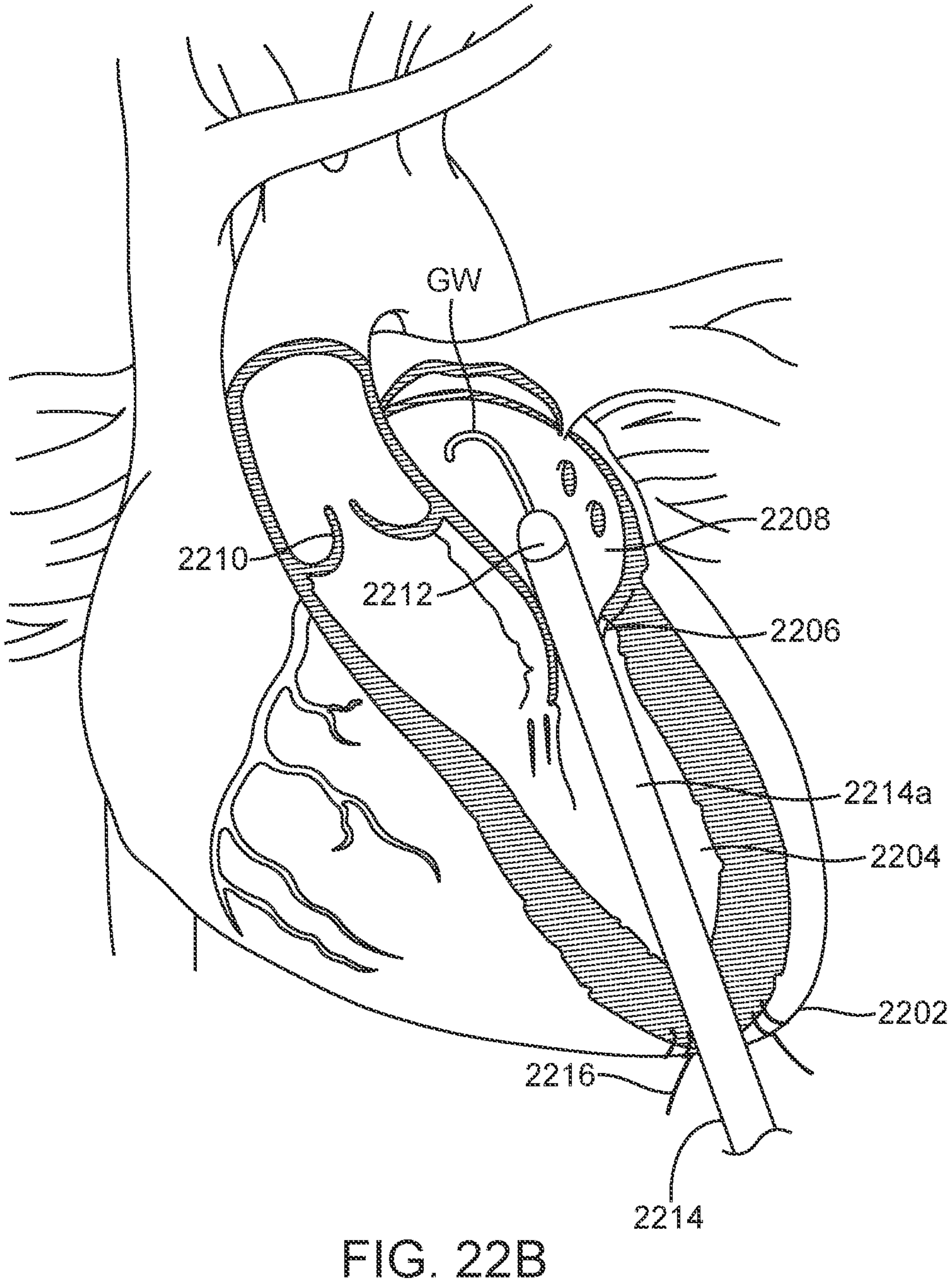

In FIG. 22B a delivery device 2214 is introduced through an incision in the apex 2202 and over a guidewire GW through the ventricle 2204, past the mitral valve 2206 with a distal portion of the delivery device 2214 disposed in the atrium 2208. The delivery device has a rounded tip 2212 that is configured to pass through and dilate the incision, and can be advanced through the heart without causing unwanted trauma to the mitral valve 2206 or adjacent tissue. Suture 2216 may be stitched around the delivery device 2214 at the apex 2202 using a purse string stitch or other patterns known in the art in order to prevent excessive bleeding and to help hold the delivery device in position.

Figure 22C:
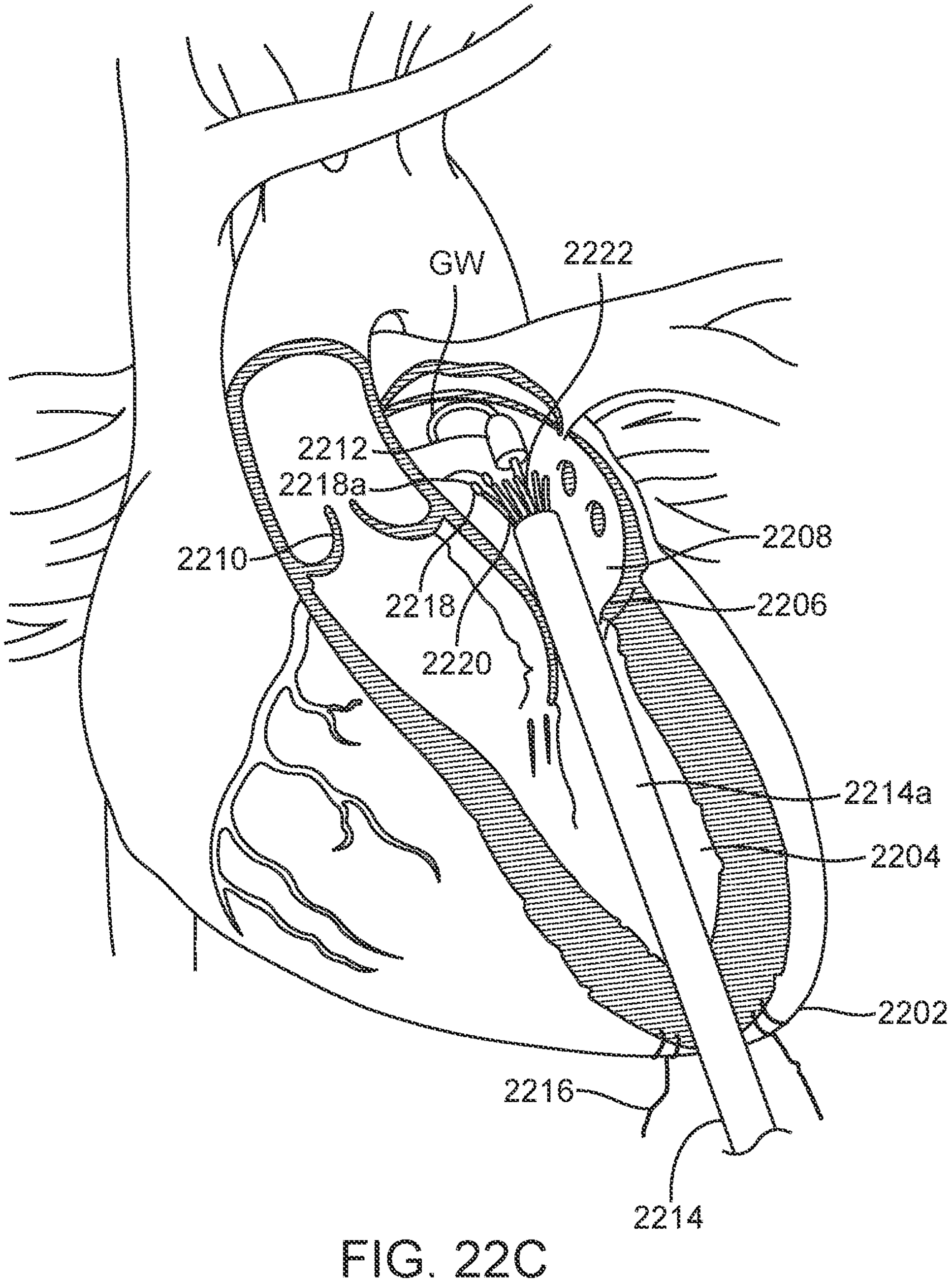

In FIG. 22C, the outer sheath 2214*a* of the delivery device 2214 is retracted proximally relative to the prosthetic mitral valve 2220 (or the prosthetic mitral valve is advanced distally relative to the outer sheath 2214*a*) to expose the alignment element 2218 and a portion of the atrial skirt region 2222 on the prosthetic mitral valve 2220 which allows the atrial skirt region 2222 to begin to partially radially expand outward and flare open. Alignment element 2218 may include a pair of radiopaque markers 2218*a* which facilitate visualization under fluoroscopy. The physician can then align the alignment element so that the radiopaque markers 2218*a* are disposed on either side of the anterior mitral valve leaflet. Delivery device 2214 may be rotated in order to help align the alignment element. The alignment element may be situated adjacent the aortic root and between the fibrous trigones of the native anterior leaflet.

Figure 22D:
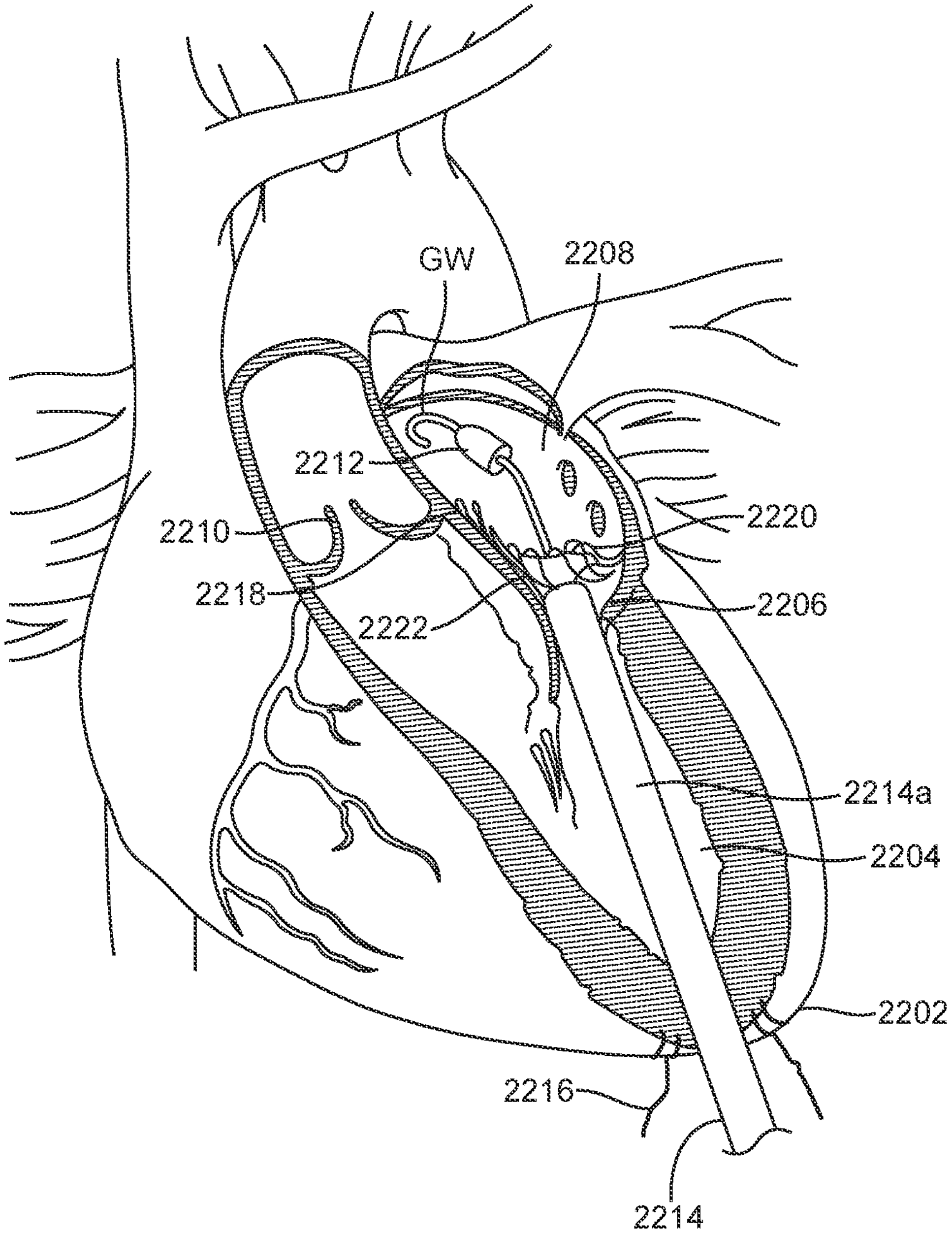

In FIG. 22D once alignment has been obtained, the sheath 2214*a* is further retracted proximally, allowing radial expansion of the atrial skirt 2222 which flares outward to form a flange. Proximal retraction of the delivery device 2214 and prosthetic valve 2220 seat the atrial skirt 2222 against an atrial surface adjacent the mitral valve 2206 thereby anchoring the prosthetic valve in a first position.

Figure 22E:
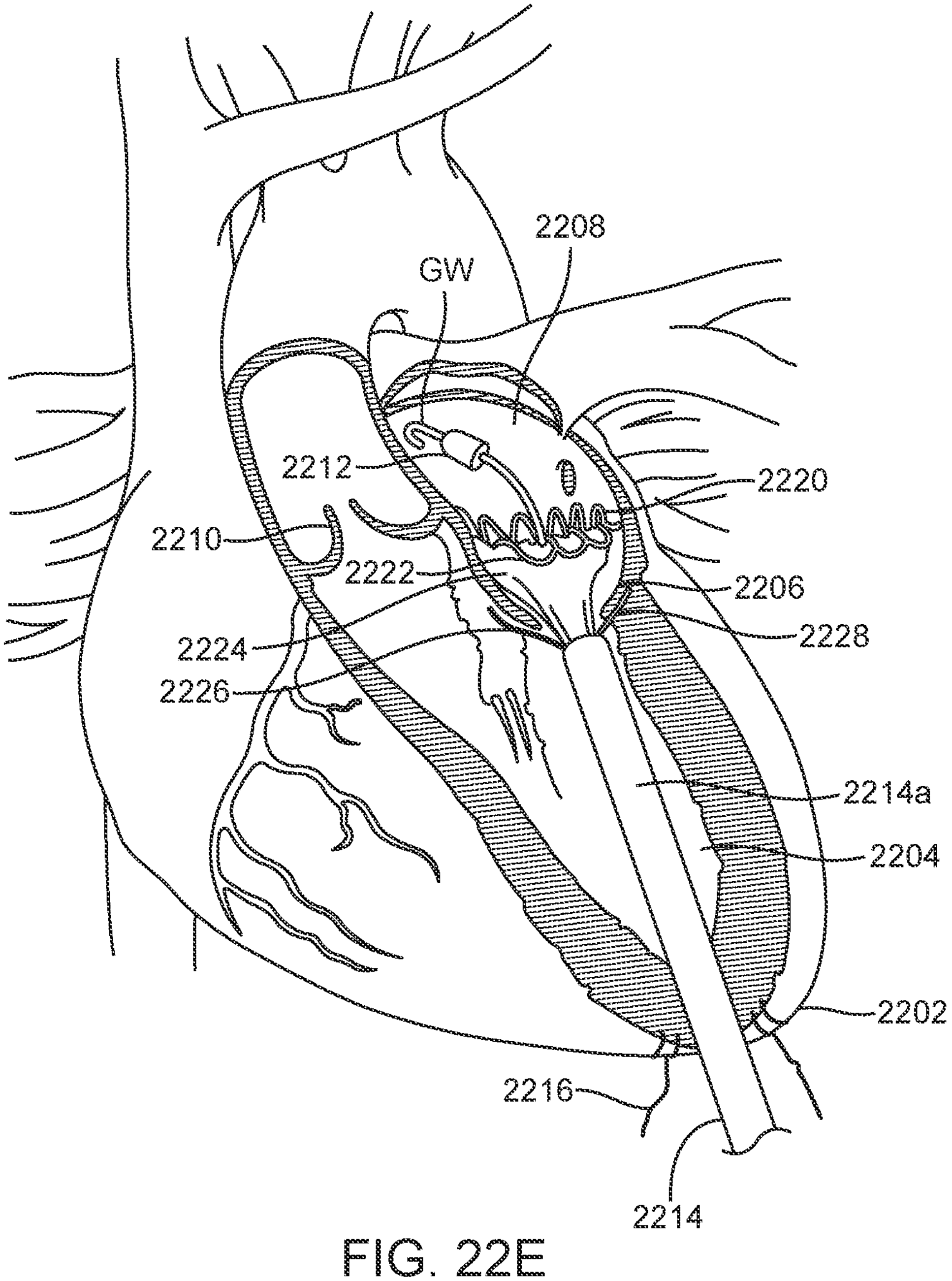

FIG. 22E shows that further proximal retraction of sheath 2214*a* exposes and axially removes additional constraint from the prosthetic valve 2220, thereby allowing more of the valve to self-expand. The annular region 2224 expands into engagement with the mitral valve annulus and the ventricular trigonal tabs 2226 and the posterior tab 2228 radially expand. Portions of the ventricular skirt serve as deployment control regions and prevent the entire ventricular skirt from expanding because they are still constrained. The tabs are captured between the anterior and posterior mitral valve leaflets and the ventricular wall. The posterior ventricular anchoring tab 2228 may be aligned in the middle of the posterior mitral valve leaflet where there is an absence of chordae attachments, and is passed over the posterior leaflet to seat between the posterior leaflet and the ventricular wall. The two ventricular trigonal anchoring tabs 2226 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 22F:
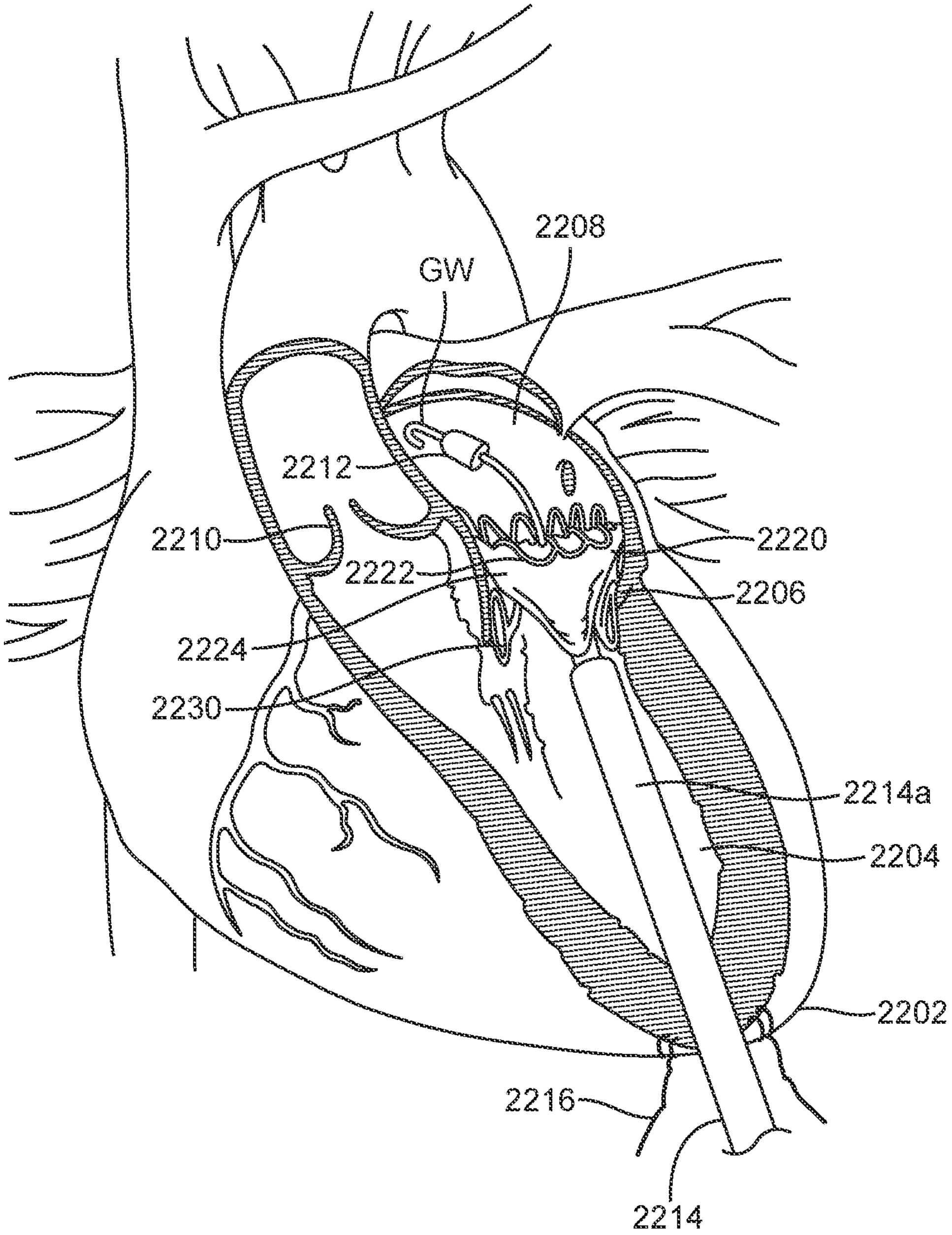
Figure 22G:
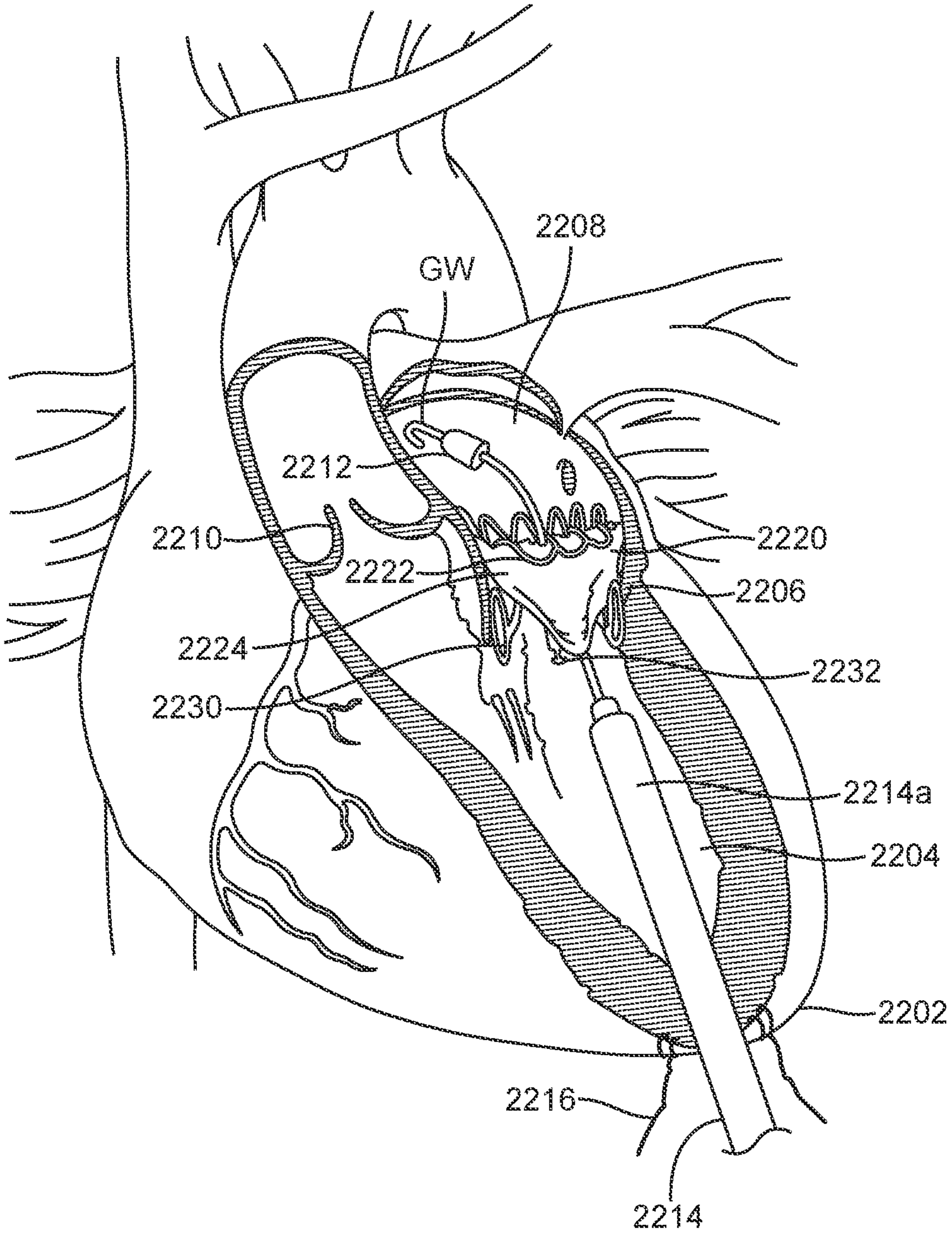

FIG. 22F shows that further retraction of sheath 2214*a* releases the ventricular trigonal tabs and the posterior tab and the deployment control regions of the ventricular skirt 2230 are also released and allowed to radially expand outward against the native mitral valve leaflets. This creates a sealing funnel within the native leaflets and helps direct blood flow through the prosthetic mitral valve. With the commissures of the prosthesis still captured within the delivery system, very minor adjustments may still be made to ensure accurate positioning, anchoring and sealing. The prosthetic valve is now anchored in four positions. The anchor tabs 2232 are then released from the delivery device by retraction of an inner shaft, allowing the tabs to self-expand out of slots on the delivery catheter as previously discussed above and shown in FIG. 22G. The prosthetic valve is now implanted in the patient's heart and takes over the native mitral valve. The delivery device 2214 may then be removed from the heart by proximally retracting it and removing it from the apex incision. The suture 2216 may then be tied off, sealing the puncture site.

Transseptal Delivery Methods

Figure 23A:
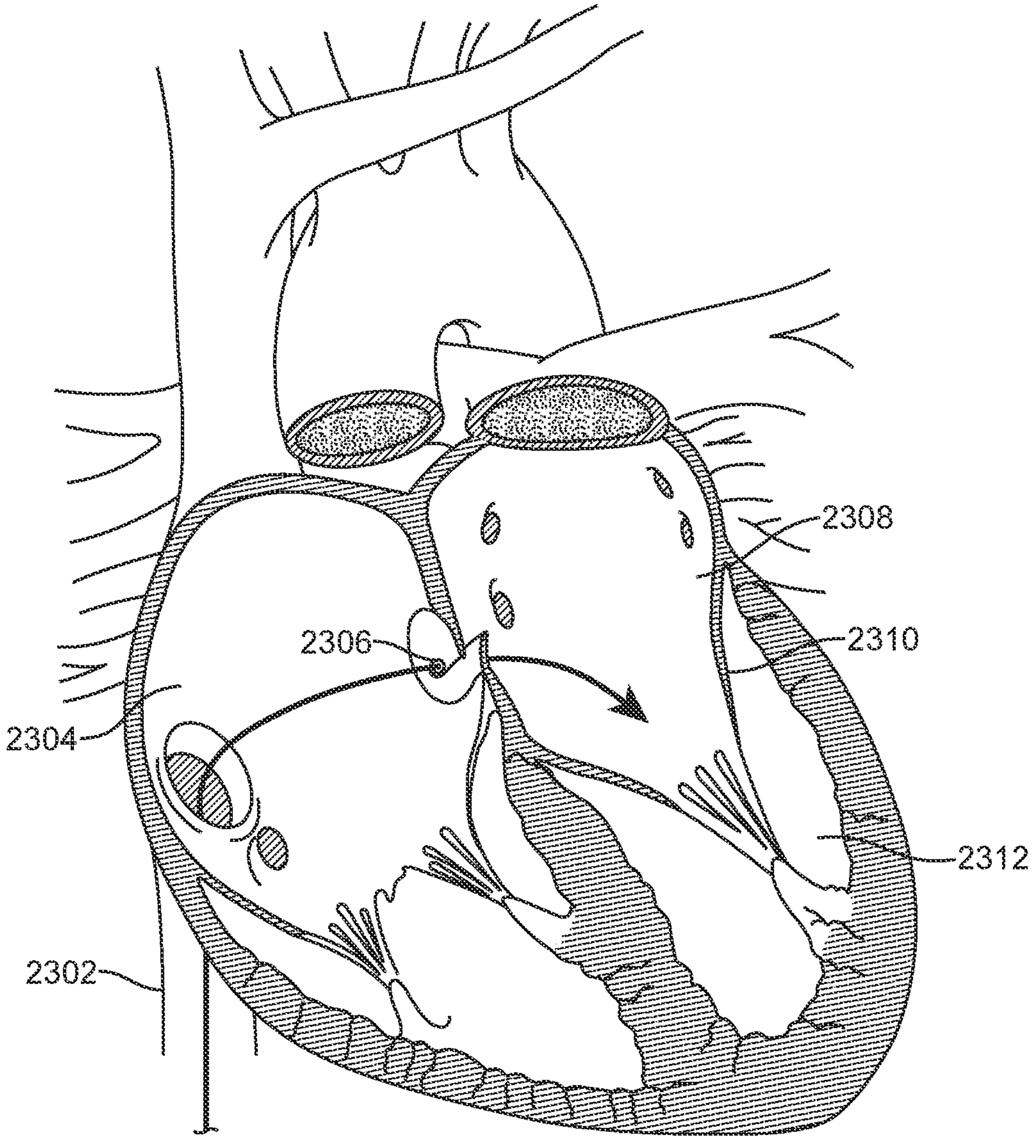
FIGS. 23A-23G illustrate an example of a method of transseptally delivering a prosthetic mitral valve.

FIGS. 23A-23G illustrate an example of transseptally delivering a prosthetic mitral valve. This example may use any of the prosthetic valves described herein, and may use any of the delivery devices described herein if modified appropriately. One of skill in the art will appreciate that relative motion of the various shafts in the delivery system examples disclosed above may need to be reversed in order to accommodate a transseptal approach. FIG. 23A illustrates the general transseptal pathway that is taken with the delivery device passing up the vena cava 2302 into the right atrium 2304. A transseptal puncture 2306 is created through the atrial septum, often through the foramen ovale, so that the device may be passed into the left atrium 2308, above the mitral valve 2310 and adjacent the left ventricle 2312. Transseptal techniques have been published in the patent and scientific literature, such as in U.S. Patent Publication No. 2004/0181238 to Zarbatany et al., the entire contents of which are incorporated herein by reference.

Figure 23B:
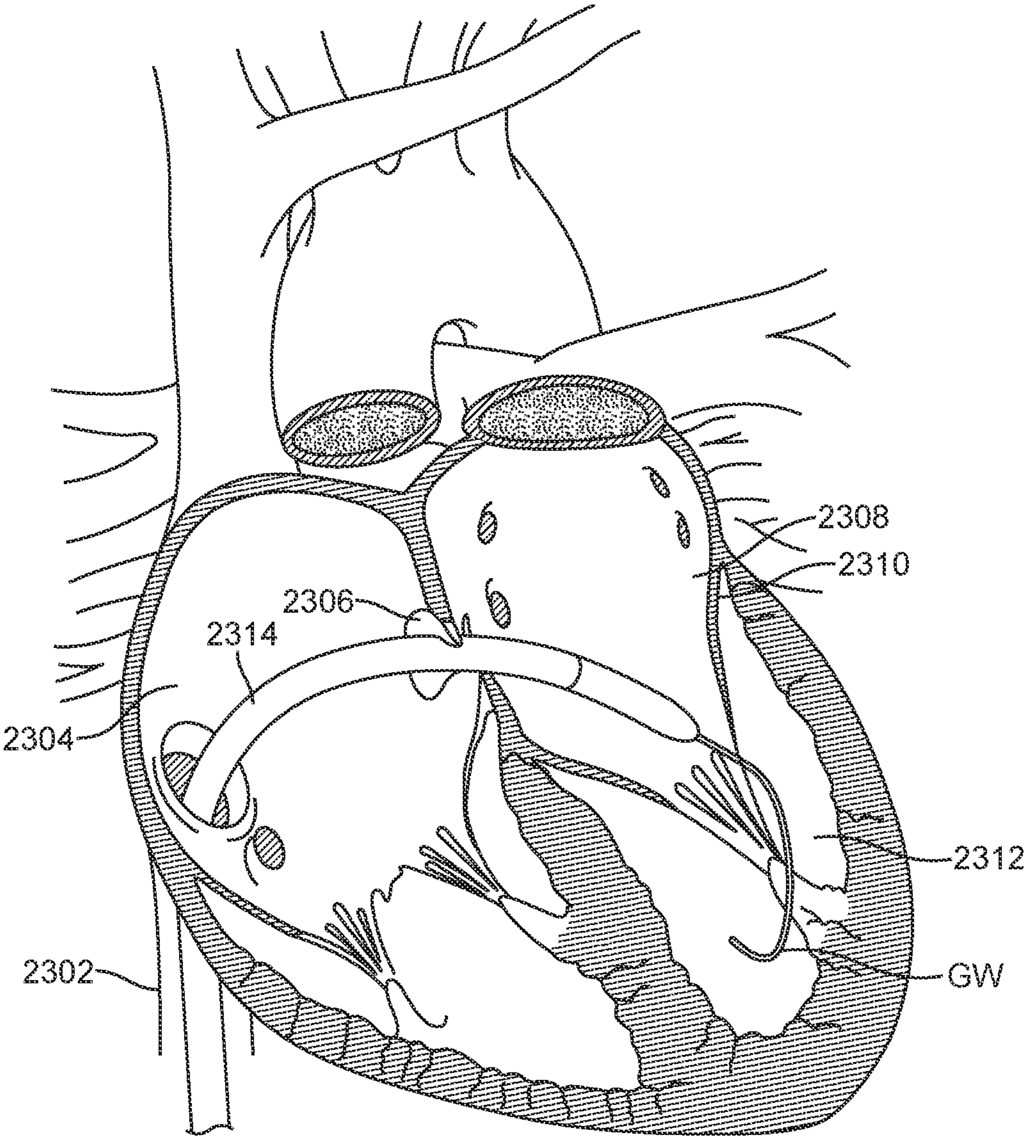

In FIG. 23B a delivery device 2314 is passed over a guidewire GW through the vena cava 2302 into the right atrium 2306. The delivery device 2314 is then transseptally passed through the atrial wall into the left atrium 2308 adjacent the mitral valve 2310. The guide-wire GW may be disposed across the mitral valve 2310 in the left ventricle 2312. The distal tip of the delivery device typically includes a nose cone or other atraumatic tip to prevent damaging the mitral valve or adjacent tissue.

Figure 23C:
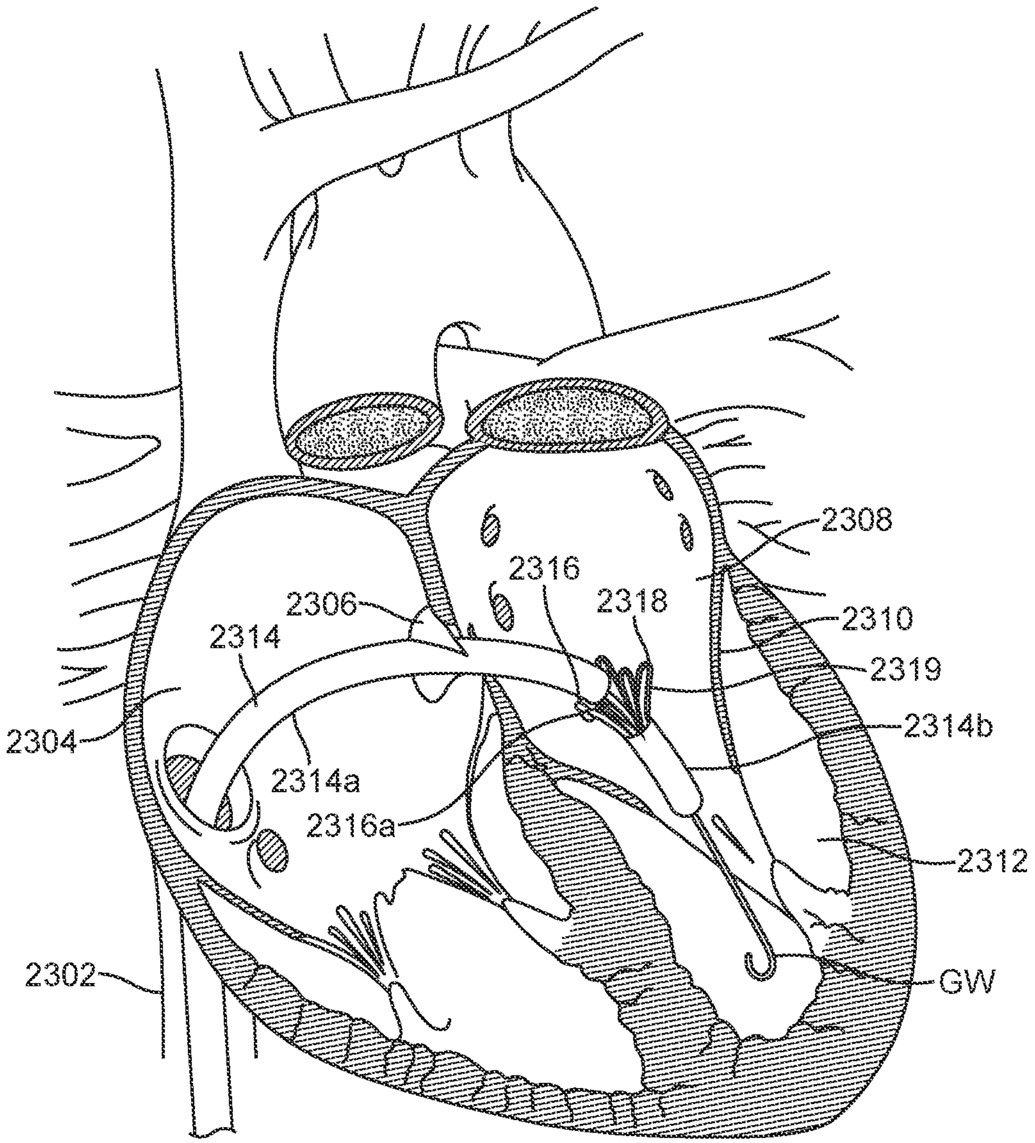

In FIG. 23C, the outer sheath 2214*a* of the delivery device 2214 is retracted proximally relative to the prosthetic mitral valve 2319. Alternatively, a distal portion 2314*b* of the delivery device 2214 may be advanced distally relative to the prosthetic valve 2319 to expose the alignment element 2316 and a portion of the atrial skirt region 2318 on the prosthetic mitral valve 2319 which allows the atrial skirt region 2318 to begin to partially radially expand outward and flare open. Alignment element 2316 may include a pair of radiopaque markers 2316*a* which facilitate visualization under fluoroscopy. The physician can then align the alignment element so that the radiopaque markers 2316*a* are disposed on either side of the anterior mitral valve leaflet. The alignment element may be situated adjacent the aortic root and between the fibrous trigones of the native anterior leaflet. Delivery device 2214 may be rotated in order to help align the alignment element.

Figure 23D:
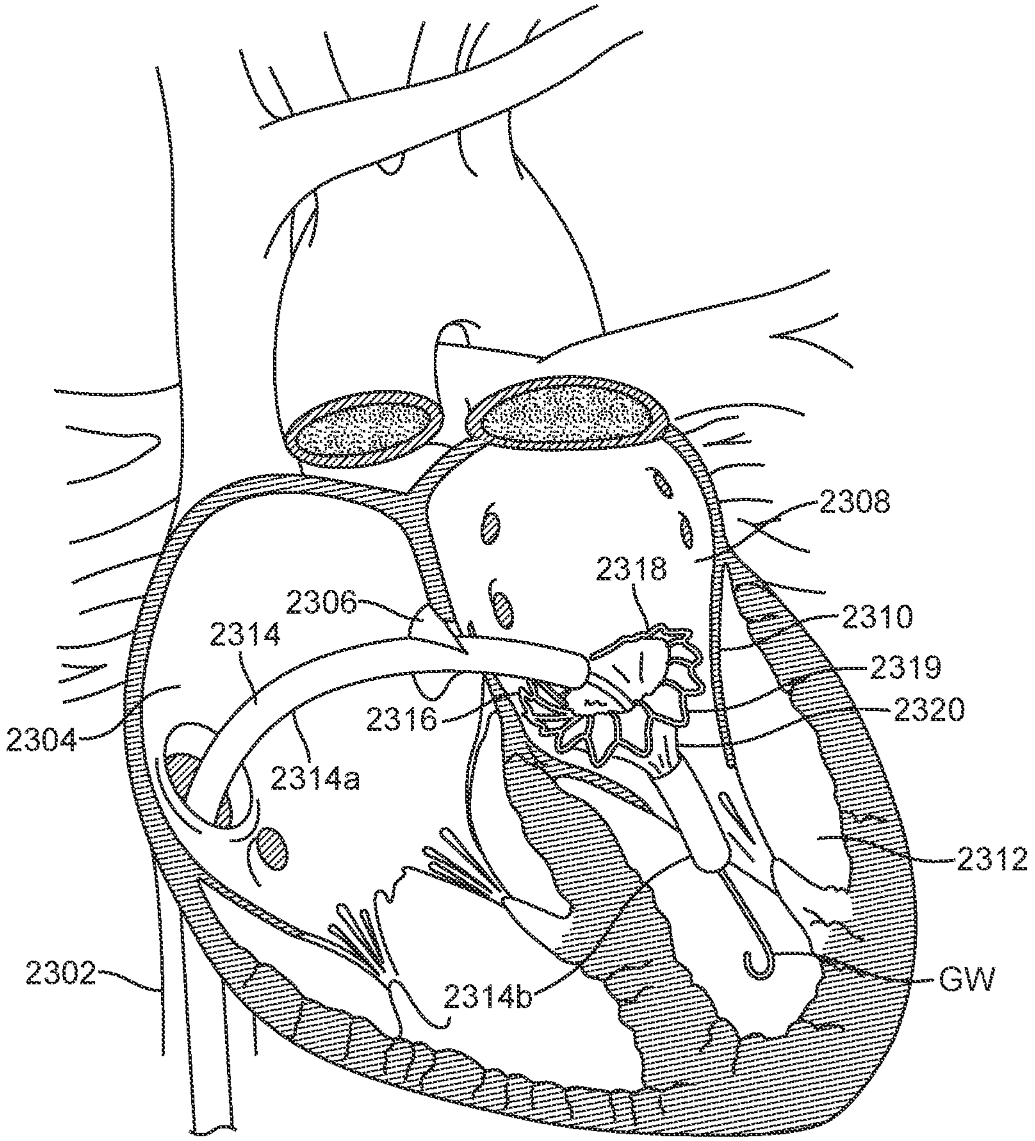

In FIG. 23D once alignment has been obtained, the distal portion 2314*b* is further advanced distally allowing radial expansion of the atrial skirt 2318 which flares outward to form a flange. Distally advancing the delivery device 2214 and prosthetic valve 2319 seats the atrial skirt 2318 against an atrial surface adjacent the mitral valve 2310 thereby anchoring the prosthetic valve in a first position.

Figure 23E:
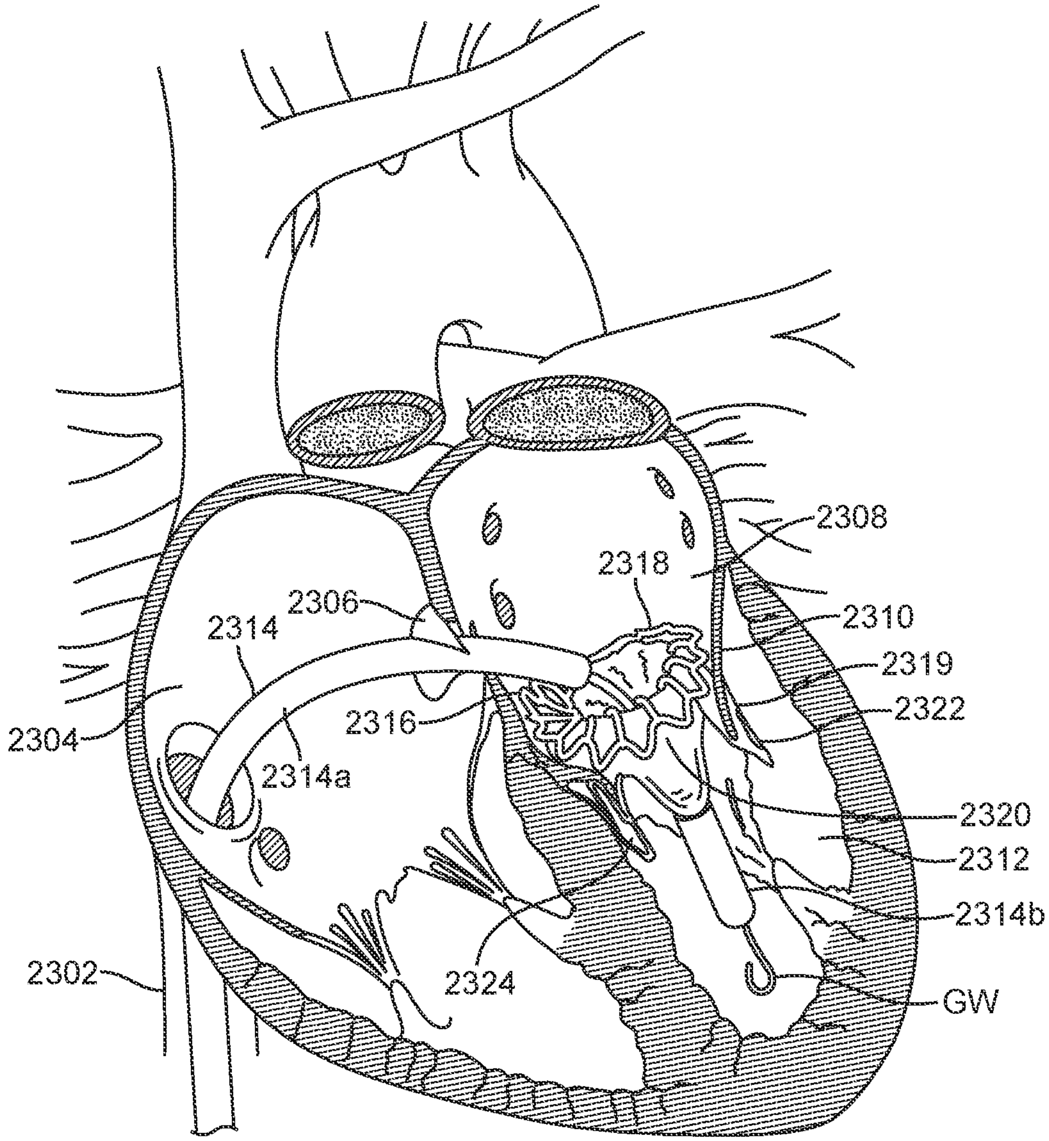

FIG. 23E shows that further distal advancement of distal portion 2314*b* exposes and axially removes additional constraint from the prosthetic valve 2319, thereby allowing more of the valve to self-expand. The annular region 2320 expands into engagement with the mitral valve annulus and the ventricular trigonal tabs 2324 and the posterior tab 2322 radially expand. Portions of the ventricular skirt serve as deployment control regions since they remain constrained and thus the entire ventricular skirt cannot expand. The tabs are captured between the anterior and posterior mitral valve leaflets and the ventricular wall. The posterior ventricular anchoring tab 2322 may be aligned in the middle of the posterior mitral valve leaflet where there is an absence of chordae attachments, and is passed over the posterior leaflet to seat between the posterior leaflet and the ventricular wall. The two ventricular trigonal anchoring tabs 2324 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 23F:
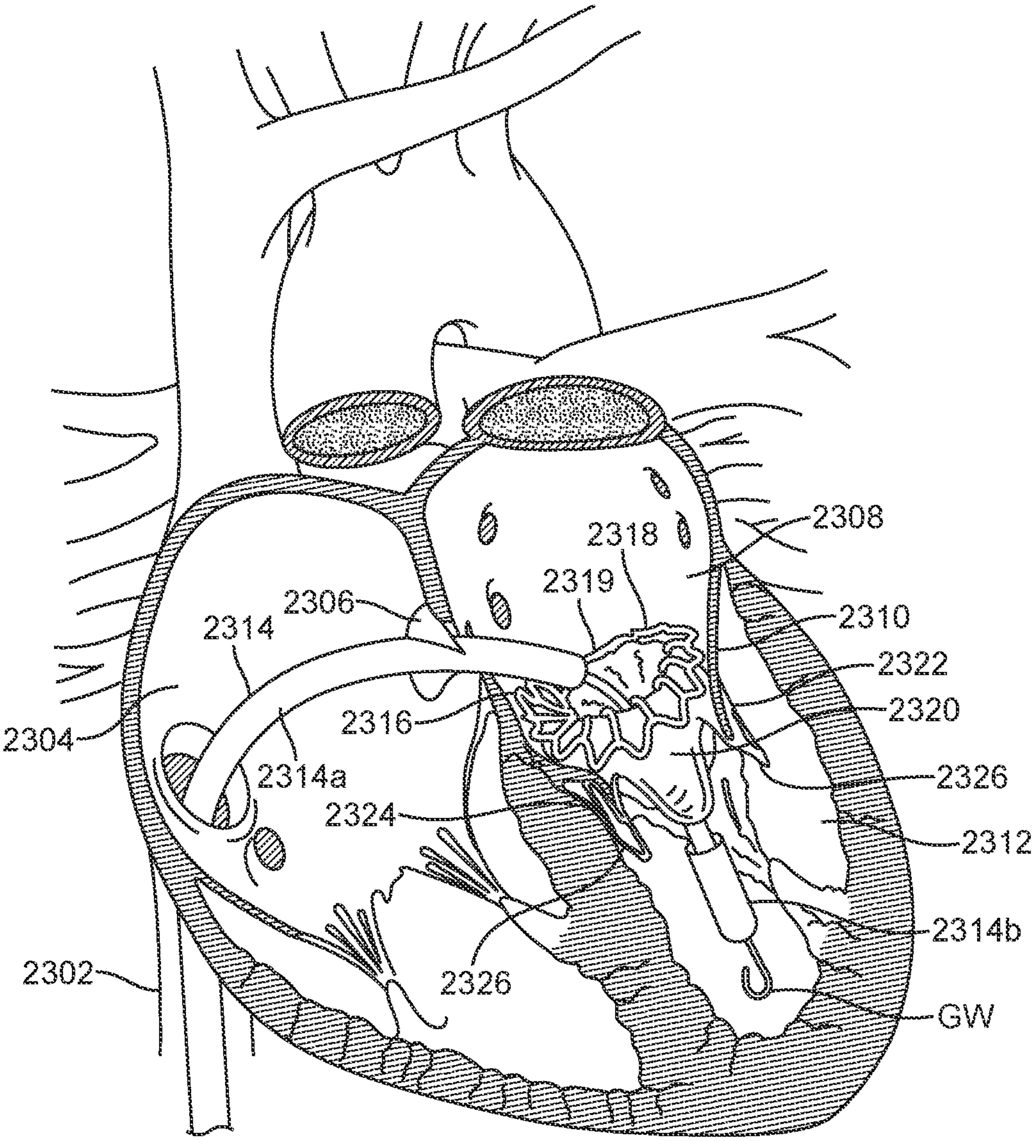
Figure 23G:
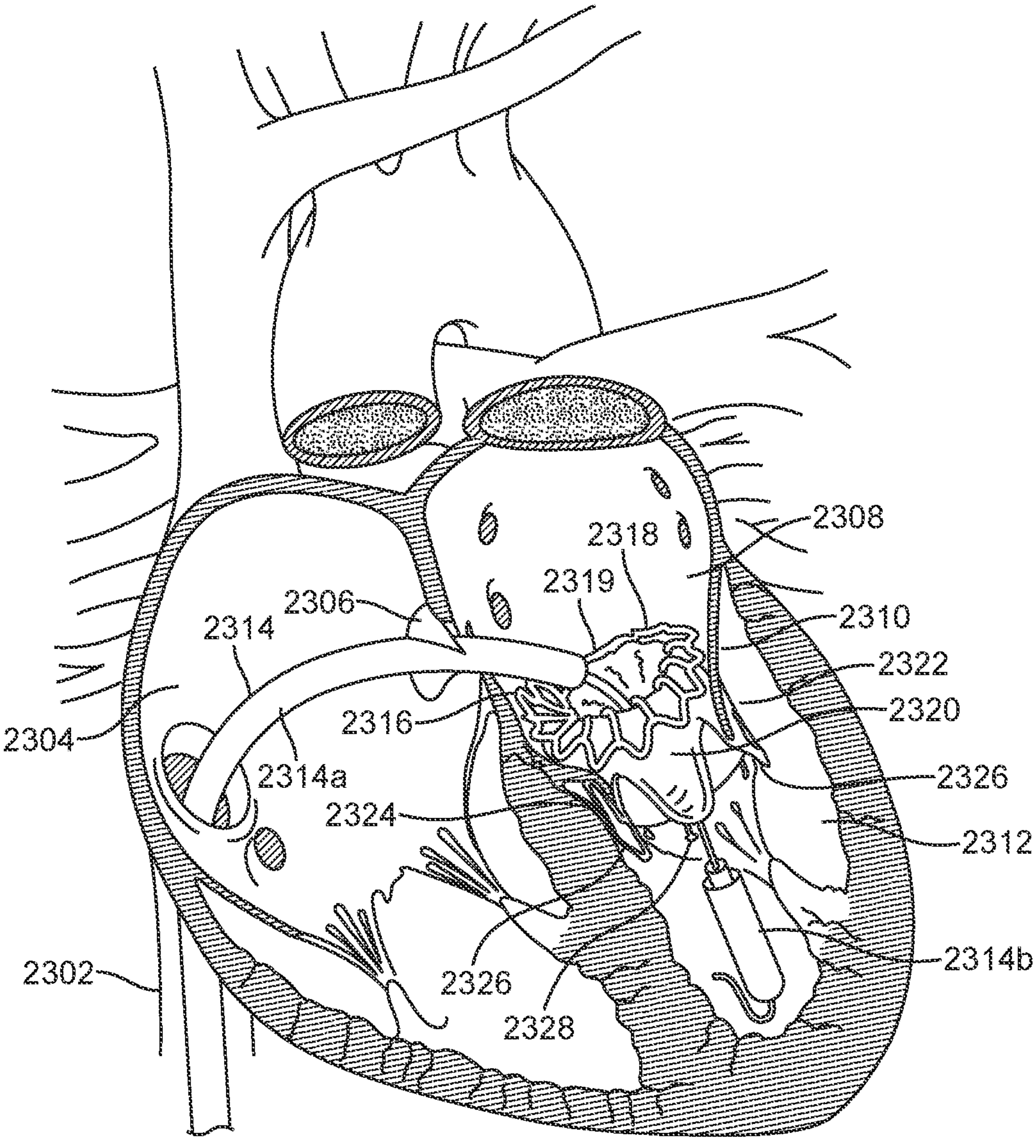

FIG. 23F shows that further distal advancement of distal portion 2314*b* releases the ventricular trigonal tabs and the posterior tab and the ventricular skirt 2326 is also released and allowed to radially expand outward against the native mitral valve leaflets without engaging the ventricular wall. This creates a sealing funnel within the native leaflets and helps funnel blood flow through the prosthetic valve. With the commissures of the prosthetic valve still captured by the delivery system, very minor adjustments may still be made to ensure accurate positioning, anchoring and sealing. The prosthetic valve is now anchored in four positions. The anchor tabs 2328 are then released from the delivery device by further advancement of an inner shaft, allowing the tabs to self-expand out of slots on the delivery catheter as previously discussed above and shown in FIG. 23G. The prosthetic valve is now implanted in the patient's heart and takes over the native mitral valve. The delivery device 2314 may then be removed from the heart by proximally retracting it back through the atrial septum, and out of the vena cava.

Figure 24:
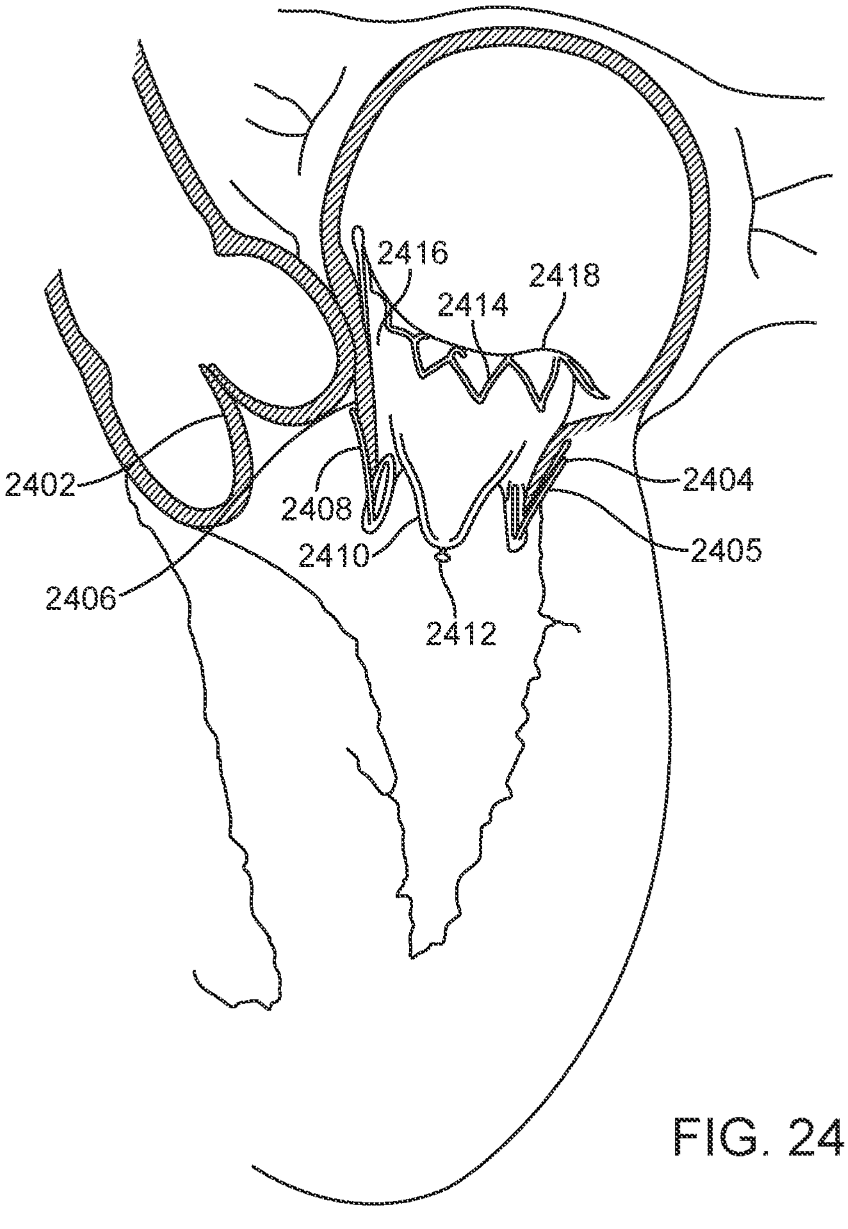
FIG. 24 illustrates a prosthetic mitral valve implanted in the mitral space.

FIG. 24 shows the prosthetic valve 2418 anchored in the mitral space after transapical or transseptal delivery. Prosthetic valve 2418 may be the prosthetic mitral valve illustrated in FIG. 8A or any of the other prosthetic valves disclosed herein, and delivered by methods shown in FIGS. 22A—ventricular skirt 2410 is also radially expanded outward to engage and press outwardly 22G or FIGS. 23A-23G. The prosthetic valve 2418 has radially self-expanded into engagement with the mitral valve to anchor it in position without obstructing other portions of the heart including the left ventricular outflow tract such as aortic valve 2402. The anterior trigonal tabs 2408 (only 1 seen in this view) and the posterior ventricular tab 2405 are radially expanded outward from the rest of the ventricular skirt 2410 and the anterior leaflet 2406 and posterior leaflet 2404 are captured between the respective tab and the ventricular skirt 2410 to form an anchor point. The at least some of the chordae tendineae and papillary muscles but may not press against the ventricular wall. The annular region 2416 is expanded radially outward to engage and press against the mitral valve annulus, and the atrial skirt 2414 has also expanded outwardly to form a flange that rests on top of the mitral valve against the atrium. Thus, the prosthetic valve 2418 is anchored in four positions in the mitral space which prevents the prosthetic valve from migrating or dislodging during contraction of the heart. Moreover, using four anchor points lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. Valve leaflets 2420 form a tricuspid valve which opens with antegrade blood flow and closes with retrograde blood flow. Tab 2412 on a tip of the commissures 2421 (best seen in FIG. 25) remains free after disengagement from the delivery device.

Figure 25:
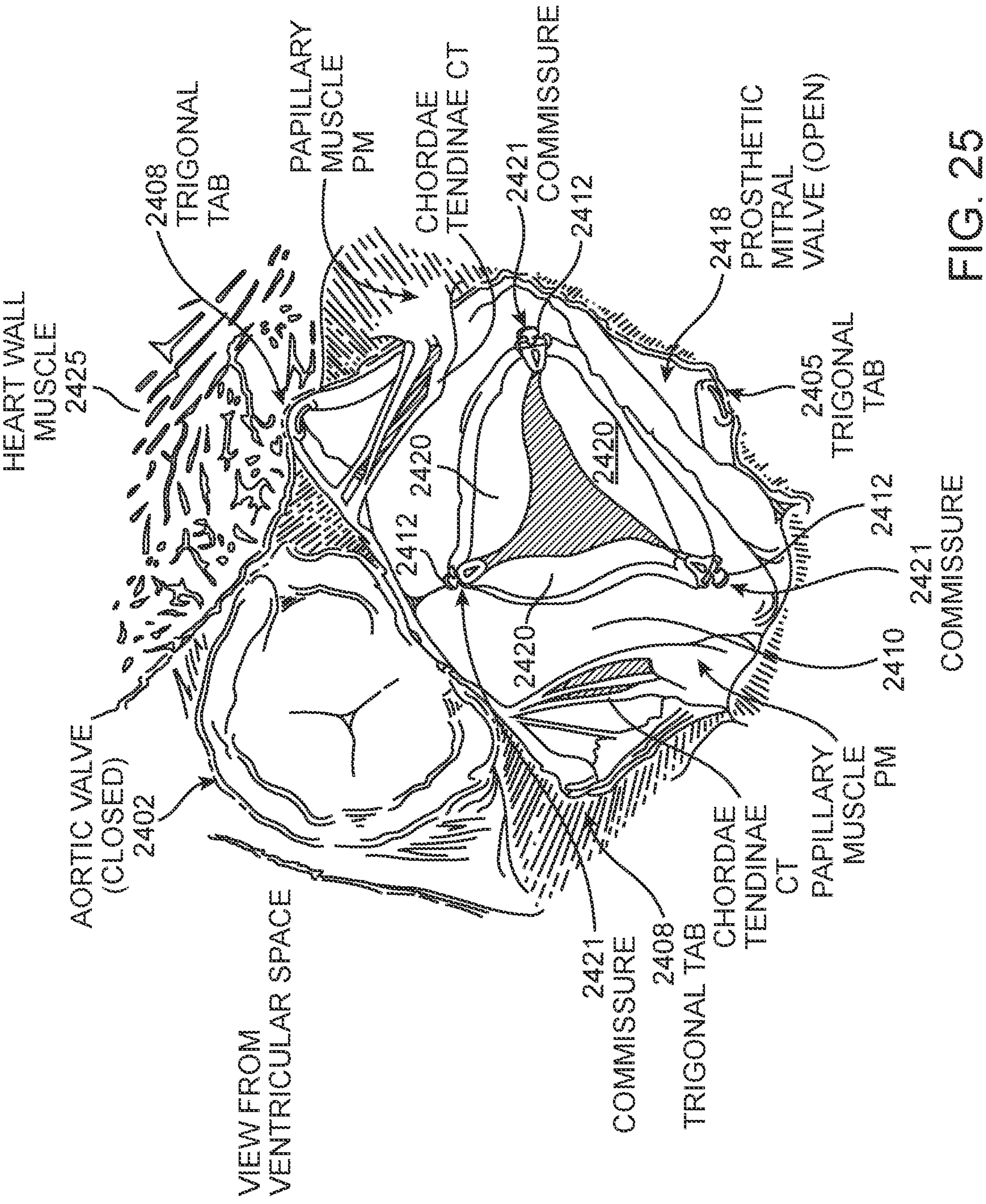
FIG. 25 illustrates a bottom view of a mitral valve implanted in the mitral space looking upward from the left ventricle.

FIG. 25 illustrates the prosthetic valve 2418 of FIG. 24 anchored in the mitral space and viewed from the left ventricle, looking upward toward the atrium. As previously mentioned, the prosthetic valve 2418 may be transapically or transseptally delivered and may be the prosthetic mitral valve illustrated in FIG. 8A, delivered by methods shown in FIGS. 22A-22G or FIGS. 23A-23G. This view more clearly illustrates anchoring and engagement of the prosthetic mitral valve 2418 with the adjacent tissue. For example, the three valve leaflets 2420 forming the tricuspid valve are shown in the open position, allowing blood flow therepast. Additionally, the anterior trigonal tabs 2408 and the posterior ventricular tab 2405 are shown radially expanded outward into engagement with the ventricular heart tissue 2425. The anterior portion of the prosthetic valve in between anterior trigonal tabs 2408 is approximately flat to match the corresponding flat anatomy as previously discussed above. The flat shape of the anterior portion of the prosthetic valve prevents the prosthetic valve from impinging on and obstructing adjacent anatomy such as the left ventricular outflow tract including the aortic valve. FIG. 25 also illustrates how the ventricular skirt 2410 expands radially outward against the native mitral valve leaflets.

Drug Delivery

Any of the prosthetic valves may also be used as a drug delivery device for localized drug elution. The therapeutic agent may be a coated on the prosthetic valve, on the tissue covering the anchor, on both, or otherwise carried by the prosthetic valve and controllably eluted therefrom after implantation. Examples of drugs include anti-calcification drugs, antibiotics, anti-platelet aggregation drugs, anti-inflammatory drugs, drugs which inhibit tissue rejection, anti-restenosis drugs, anti-thrombogenic drugs, thrombolytic drugs, etc. Drugs which have these therapeutic effects are well known to those of skill in the art.

Anchor Tabs

Any example of a prosthetic valve disclosed herein may include one or more anterior anchor tabs and/or one or more posterior anchor tabs, or anchor tabs may be positioned elsewhere on the expandable frame (e.g. laterally or medially). While these examples are promising, in certain situations, it can be challenging to observe the anchor tabs under fluoroscopy or echocardiography. Moreover, under certain circumstances, the tips of the anchor tabs may engage and irritate the tissue against which the tab anchors or cause trauma. Therefore, improved anchor tabs may be desirable in overcoming at least some of these challenges.

Figure 26E:
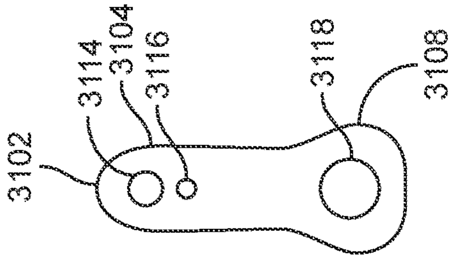
FIGS. 26A-26E show examples of anchor tabs.
Figure 26D:
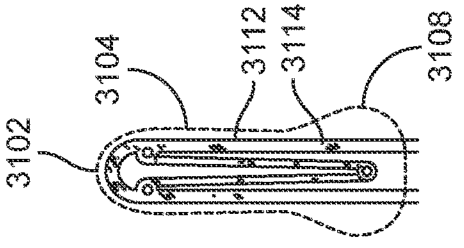
Figure 26C:
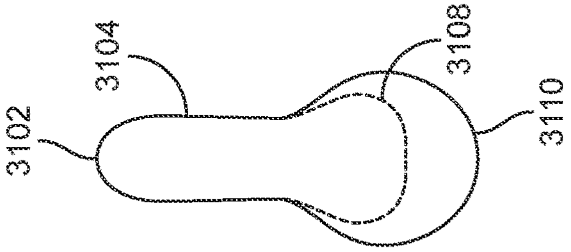

In any of the examples of prosthetic valves with anchor tabs, it may be desirable to modify the anchor tabs so that they are more easily observed under fluoroscopy, echocardiography or other visualization techniques used in a catheterization laboratory or during any medical procedure including visits to a physician. FIG. 26A shows a prosthetic valve 3100 with an anchor tab 3102 on the ventricular end (the prosthesis is inverted with the atrial flange on the lower end). The prosthetic valve 3100 may be any of the prosthetic valves disclosed herein and the anchor tab 3102 may be an anterior anchor tab, a posterior anchor tab, or any of the anchor tabs disclosed herein. FIGS. 26B-26E illustrate some examples of anchor tabs 3102 that may be used with any anchor tab of any prosthesis disclosed herein. The anchor tabs may be formed from struts that are covered with a covering such as Dacron, or the anchor tabs may be solid.

Figure 26B:
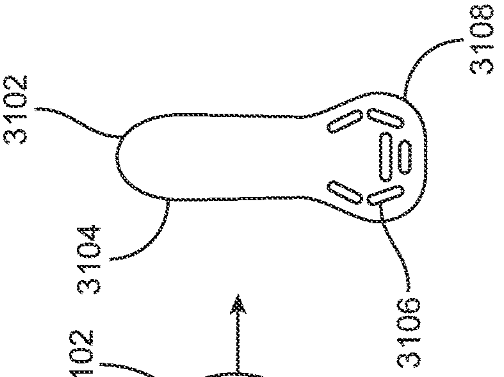
Figure 26A:
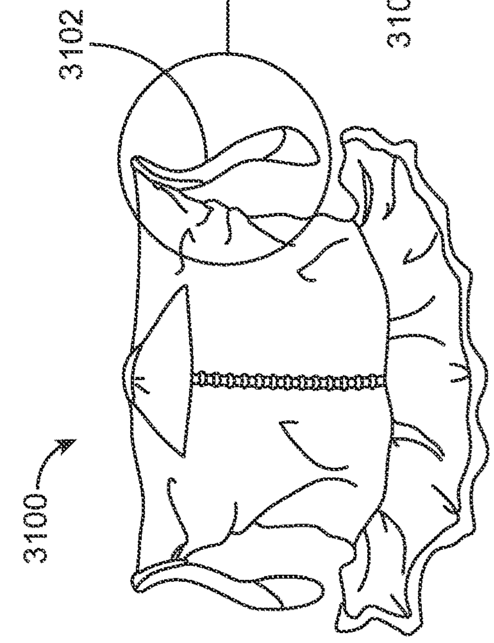

FIG. 26B shows anchor tab 3102 with a base 3104 and the free end 3108. The base is coupled to the prosthetic valve and may be coupled to the ventricular skirt. The base has a narrow elongate section with a rounded end that is coupled to the prosthetic valve. The free end 3108 is the end that engages and anchors against tissue, for example against a fibrous trigone if the anchor is an anterior anchor, or against a posterior portion of the annulus if the anchor is a posterior anchor. The free end has an enlarged head region relative to the base and the enlarged head portion provides greater contact surface area therefore distributing forces over a larger surface area thereby reducing the potential of tissue trauma, as well as providing a more radiopaque or echogenic area for visualization. Optionally, the free end may include a plurality of slots that extend partially or entirely through the tab to provide a pattern that also may facilitate visualization under radiography or ultrasound. Here, the optional pattern includes two unconnected slots on either side of the free end that form a chevron, and two horizontal slots adjacent the engagement edge of the free end. One of the horizontal slots is longer than the other horizontal slot. Again, this optional pattern may help with visualization.

Additionally, having slots in the anchor tab will allow the anchor tab to have desirable mechanical properties, such as a tip flexibility or stiffness, thereby further avoiding tissue trauma. The slots may be replaced with radiopaque or echogenic filaments or other materials that enhance visibility.

FIG. 26C illustrates another example of an anchor tab that may be used with any anchor tab on any prosthetic valve disclosed herein. Here the tab 3102 generally takes the same form as the tab in FIG. 26B with the major difference being that there are no slots and this example includes a cover or coating. The tab 3102 includes a base 3104 and also a free end 3108 that are substantially the same as the free end in FIG. 26B. However, here the free end 3108 does not include the slots of FIG. 26B. Also, the free end includes a cover or coating 3110 that is disposed over or otherwise coupled to the free end 3108. The cover or coating may be any material that increases visualization under x-rays or ultrasound. For example, the coating or cover may include silicone to promote echogenicity, or a dense material to promote radiopacity. In addition to facilitating visualization, the cover or coating also provides a cushion and/or larger surface area to distribute forces thereby minimizing or preventing trauma to tissue when the tab is anchored against tissue and hence the cover or coating may be used to control the mechanical properties of the anchor tab.

FIG. 26D illustrates another example of an anchor tab 3102 which generally takes the same form as the tab in FIG. 26B with the major difference being the use of surface features. Tab 3102 includes a base 3104 and a free end 3108 that generally take the same form as the base and free end in FIG. 26B. In this example, the anchor tab is formed from a plurality of interconnected struts 3112 and a covering is disposed over the struts. The covering may be any material such as Dacron, ePTFE, Teflon, tissue, etc. The individual struts 3112 may have surface features or be etched to have surface features 3114 to enhance radiopacity or echogenicity. The surface features may also enhance the mechanical properties. Some or all of the struts may have the surface features or etching.

FIG. 26E shows another example of an anchor tab with features that may be used to enhance visualization or the mechanical properties of the tab. Tab 3120 generally takes the same form as the tab in FIG. 26B and has a base 3104 and free end 3108 substantially similar to those described in FIG. 26B. The anchor tab may have one or more apertures extending through the anchor tab. Here, the anchor tab includes an aperture 3108 in the free end, and two apertures 3114, 3116 in the base. Aperture 3108 is the larger aperture and may be a circular hole or another pattern, while the two base apertures 3114, 3116 also are circular and both smaller than the free end aperture 3108 but one aperture closest to the edge of the base being larger than the other aperture in the base. An operator is able to see the apertures and determine the position of the free end and the base end. The apertures also may be adjusted to increase or decrease flexibility or other mechanical properties of the anchor tabs as desired.

FIGS. 27A-27E illustrate additional examples of anchor tabs that may be used with any of the prosthetic valves disclosed herein.

Figure 27A:
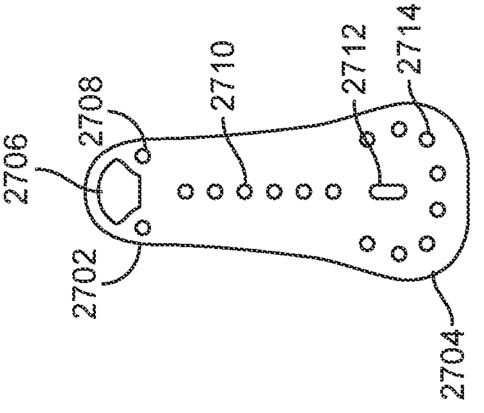
FIGS. 27A-27E illustrate additional examples of anchor tabs.

FIG. 27A shows an anchor tab having a base 2702 and a free end 2704 similar to those previously described in FIGS. 26A-26E above. The free end includes a plurality of round holes 2714 disposed around the perimeter of the free end with an axially oriented racetrack shaped slot 2712 parallel with the longitudinal axis of the anchor tab in the free end region. A linear array of round holes 2710 is disposed in between the base and free end, and a wide hole 2706 is disposed on the base. The wide hole 2706 allows tethers or other objects to be coupled to the base of the anchor tab (also sometimes referred to as an elbow) to control elbow deployment. Round holes 2708 are disposed on either side of the wide hole 2706. Again, the holes help facilitate visualization of the anchor tab and provide desirable mechanical properties to the anchor tab. The holes may also be used to pass suture through in order to secure objects (e.g. a cover) to the anchor tab.

Figure 27B:
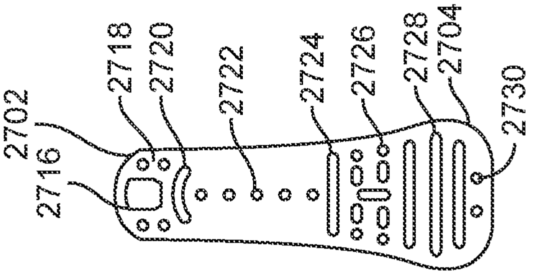

FIG. 27B is similar to the example of FIG. 27A with a different pattern of slots and holes. The base 2702 includes a wide hole 2716 through which a tether or other control element may be disposed or coupled to in order to control elbow deployment. Either side of wide hole 2716 includes a linear array of holes 2718 to mark the base with an arcuate slot 2720 under the wide hole 2716. The middle portion of the anchor tab between the base and free end includes a linear array of holes 2722 with horizontal linear slots 2724, 2728 of varying length extending down into the free end with round and oval holes 2726 disposed between some of the horizontal slots. A vertical oval slot maybe disposed in between horizontal slots. A final linear array of round holes 2730 may be horizontally oriented along the free end.

Figure 27C:
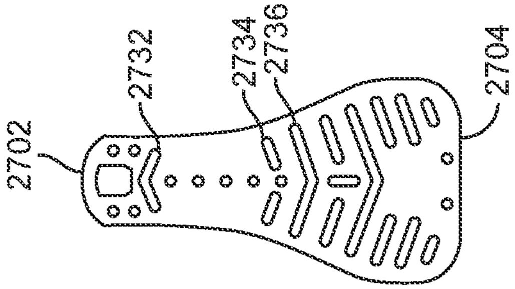

FIG. 27C illustrates another example of hole and slot patterns which may be used in an anchor tab to control radiopacity or echogenicity as well as mechanical characteristics of the anchor tab. The hole pattern is substantially the same as in FIG. 27B with a few modifications. For example, the arcuate slot 2720 has been replaced with a chevron shaped slot 2732 pointing toward the base, and the horizontal slots 2724, 2728 have been replaced with linear slots that form chevrons pointing toward the free end. The chevrons may be open 2734 or closed 2736 in the region between the base 2702 to the free end 2704.

Figure 27D:
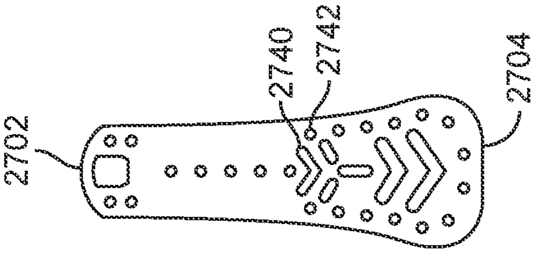

FIG. 27D shows another hole and slot pattern that may be used in any anchor tab. The anchor tab includes a base 2702 and a free end 2704. The hole pattern near the base is similar to that of FIG. 27C except without chevron 2732. Closed chevrons 2740 pointing toward the free end extend from the mid-section of the anchor toward the free end, and a plurality of round holes extend along the perimeter of the free end similar to FIG. 27A. Other aspects of the hole pattern are similar to FIGS. 27A-27C.

Figure 27E:
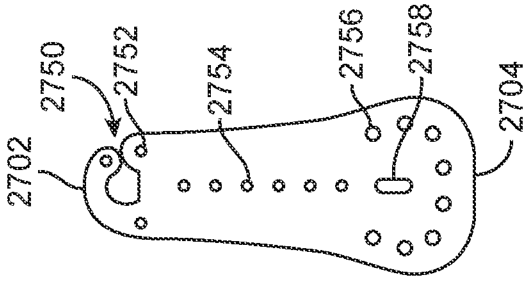

FIG. 27E illustrates still another hole and slot pattern that may be used in an anchor tab. Here, the base 2702 includes an open slot 2750 that allows a tether, filament or other object to be easily coupled or decoupled from the aperture in the base and round holes 2752 surround the slot and aperture. A linear array of holes 2754 extends vertically down the tab in the middle section between the base and the free end. A vertically oriented oval slot 2758 marks a central region of the free end and the perimeter of the free end 2704 is outlined with a plurality of round holes 2756.

The examples in FIGS. 27A-27E are not intended to be limiting and are disclosed only to illustrate how slots, holes and other surface features may be incorporated into the anchor tabs in order to facilitate visualization and control mechanical properties of the anchor tab.

Figure 28A:
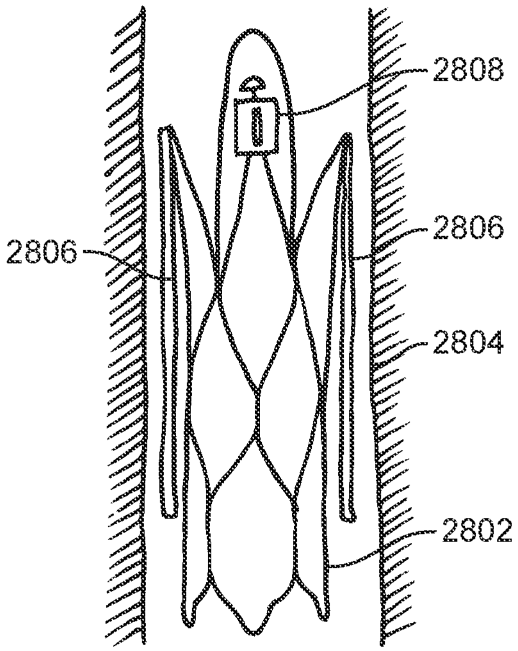
FIGS. 28A-28C illustrate an example of atraumatic anchors in the collapsed and in the expanded configurations.
Figure 28B:
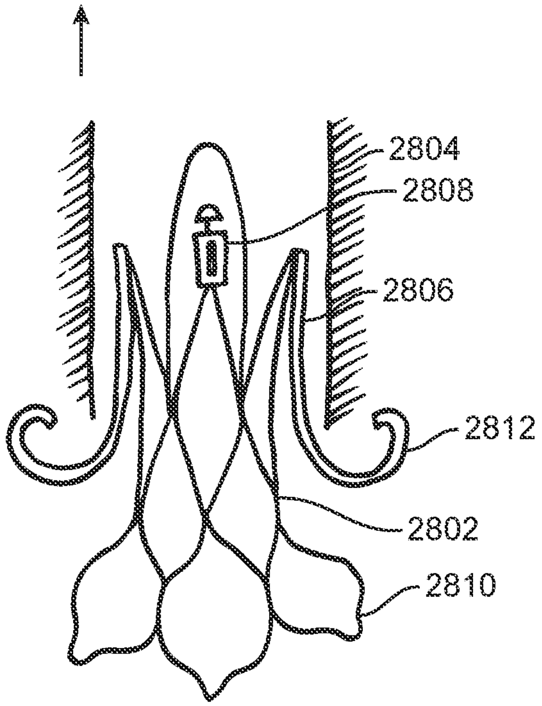
Figure 28C:
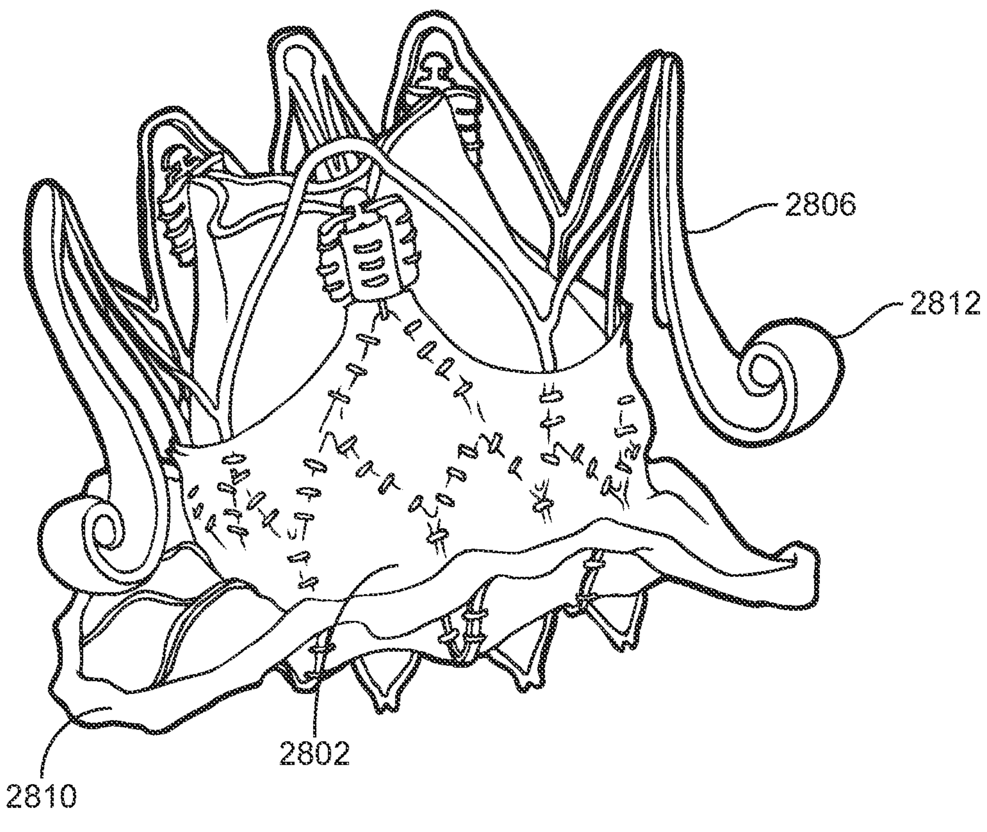

FIGS. 28A-28C illustrate another example of an anchor tab that will be more visible as well as providing reduced contact pressure and therefore a less traumatic anchor. This anchor tab may be used as an anterior anchor tab, a posterior anchor tab, or any anchor tab in any of the prosthetic valve examples disclosed herein.

FIG. 28A illustrates a prosthetic valve 2802 in a collapsed configuration and constrained by an outer tubular element 2804 such as a sheath or catheter shaft and this facilitates delivery to the treatment region in the collapsed configuration. The prosthetic valve 2802 may be any of the prosthetic valves disclosed herein and includes anchor tabs 2806 which may be anterior anchor tabs, posterior anchor tabs, combinations thereof, or other anchor tabs. In this example, only two anchor tabs are seen, but a third anchor tab is hidden and therefore this example includes two anterior anchor tabs and one posterior anchor tab. The prosthetic valve also includes commissure post 2808 with an enlarged head for releasably coupling with a delivery catheter as previously disclosed above. The anchor tabs 2806 are also constrained by sheath 2804 in a collapsed configuration such that the anchor tabs are disposed in a substantially linear shape that extends substantially parallel with the longitudinal axis of the prosthetic valve.

In FIG. 28B, the sheath 2804 is retracted away from the prosthesis 2802 as indicated by the arrow such that the atrial portion of the prosthetic valve self-expands to form an atrial skirt or flange 2810 as previously described. As the sheath 2804 is further retracted, the anchor tabs 2806 become unconstrained and they self-expand substantially the same way as the other anchor tabs described earlier in this specification. However, the free ends of the anchor tabs are also biased to roll up into coils 2812. The coiled ends may form a flat spiral spring (sometimes also referred to as a clock spring). Once the sheath is fully retracted (not illustrated in FIG. 28B), the remainder of the prosthesis self-expands and the commissures are released from the catheter.

FIG. 28C shows the prosthesis fully expanded and released from the delivery catheter. The prosthesis in the fully expanded configuration takes substantially the same form as the expanded configurations of other valve prostheses described herein. The major difference being the coiled tips 2812 of the anchor tabs. Because there is more material in the coiled tips, mass and/or density is also increased and the tips will be more visible under x-ray or ultrasound. Additionally, because the engagement portion of the anchor tab is smooth and curved as well as having a larger surface area, trauma to tissue will also be minimized or avoided.

The prosthetic valve may be formed from any number of self-expanding or shape memory materials such as Nitinol, resilient polymers or other materials known in the art. The prosthetic valve may also be formed from balloon expandable materials and a balloon catheter may be used to expand the prosthesis.

The coiled anchor tab may also be combined with any of the covering, coating, slotted, textured, or otherwise modified anchor tabs disclosed herein.

Deployment Control Mechanisms

As discussed previously, the prosthetic valve may be self-expanding, balloon expandable or it may be expandable by other techniques known in the art. In certain circumstances such as during self-expansion, the prosthesis can spring open abruptly causing the prosthesis to move or jump from its targeted deployment location. Therefore, it may be desirable to provide additional deployment control mechanisms to the prosthesis in order to ensure more accurate deployment and anchoring at the target treatment site.

A cinching or lasso mechanism may be coupled to any portion of the prosthetic valve in order to control radial expansion. For example, the lasso may be coupled to the atrial flange, the annular region, the anchor tabs, or the lasso may extend circumferentially around the ventricular portion of the prosthetic valve.

Figure 29A:
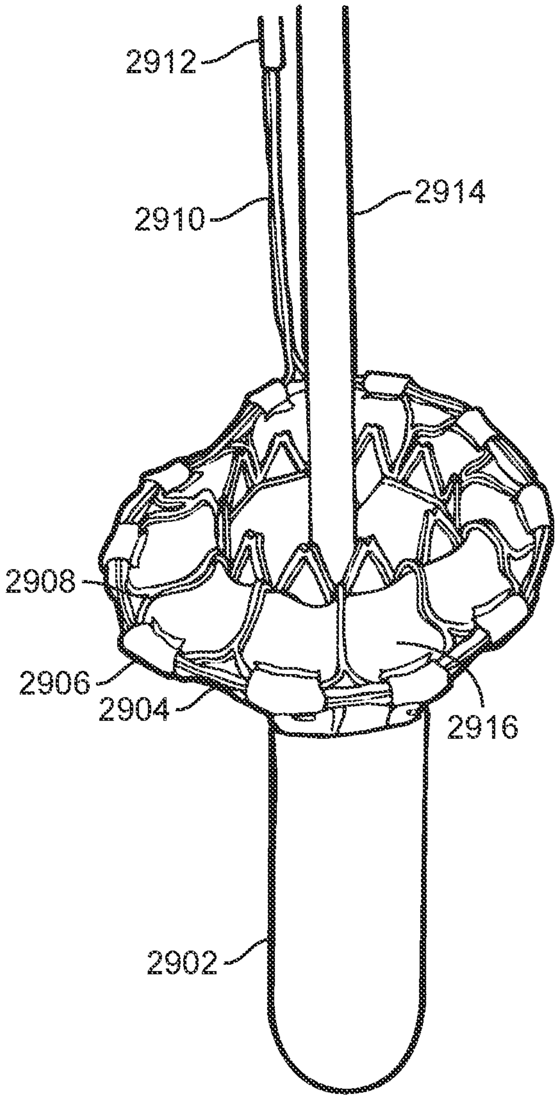
FIGS. 29A-29B show an example of a lasso control mechanism.
Figure 29B:
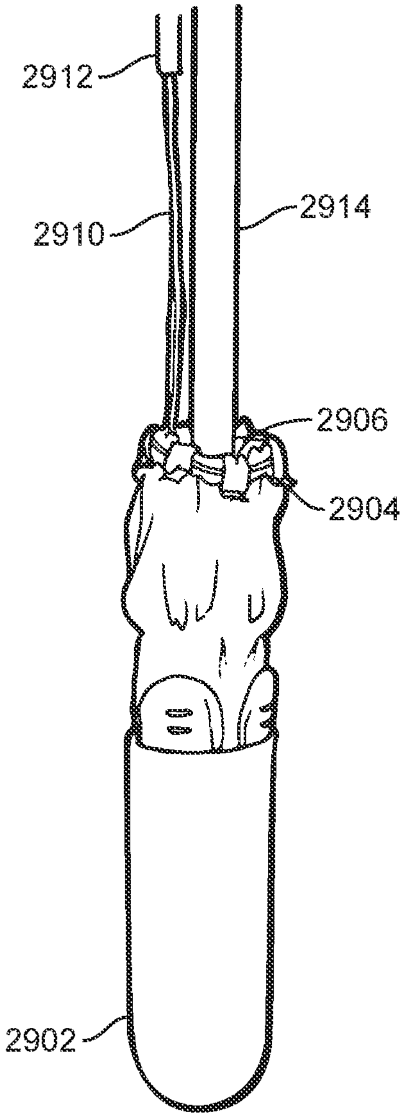

For example, FIGS. 29A-29B show a lasso coupled to the perimeter of the atrial flange in the expanded and collapsed configurations, respectively.

FIG. 29A shows the prosthetic valve in a partially expanded configuration. The prosthetic valve may be any of the prosthetic valves disclosed herein, and the atrial flange is in the expanded configuration while the remainder of the prosthetic valve is housed in a collapsed configuration in a distal capsule 2902 coupled to an elongate shaft 2914 in the delivery system. The loop portion 2904 of the lasso extends circumferentially around the perimeter of the flange and the free ends 2910 of the lasso extend proximally away from the prosthetic valve. The free ends 2910 of the lasso maybe extend proximally, and run substantially parallel to the longitudinal axis of the delivery system. The free ends may be slidably disposed in a lumen of another shaft 2912 that is part of the delivery system, or the free ends may run along an outer surface or in a lumen or annular space of the delivery catheter in order to prevent entanglement. Shaft 2912 may be disposed inside a lumen or annular space of the delivery catheter, or shaft 2912 may run alongside an outer surface of the delivery catheter. The free ends extend proximally to the proximal end of the delivery catheter where they may be manually controlled by an operator, or the free ends may be coupled to an actuator that allows the operator to manipulate the lasso. Appling tension to the lasso will generally tighten the lasso and therefore collapse the atrial flange while releasing tension will relax the lasso thereby allowing the atrial flange to expand. Collapsing the atrial flange allows the prosthetic valve to be recaptured and re-sheathed in a capsule or lumen of the delivery catheter and repositioned or removed from the patient.

The lasso may be formed from any filament such as a flexible wire or a suture. The lasso (whether a suture, wire, or other component) is passed through eyelets 2906 which are disposed around the perimeter of the atrial flange, or the lasso may be disposed through other connector features which are disposed on the prosthetic valve frame. The eyelets 2906 may be fabric tabs which are folded over themselves to form a channel through which the filament passes and then the ends of the tabs are coupled to the struts 2908 of the prosthetic valve (e.g. by suturing) or coupled to the cover 2916 (e.g. Dacron cover) disposed over the prosthetic valve.

Once the prosthetic valve has been deployed in a desired location correctly, the free ends of the lasso may be released at the proximal end and one end of the filament pulled until the lasso is pulled out of the eyelets and released from the atrial flange thereby removing the lasso completely from the prosthetic valve.

FIG. 29B shows the prosthetic valve of FIG. 29A when tension is applied to the lasso, thereby collapsing the atrial flange on the prosthetic valve so that it may be re-sheathed and then either repositioned and redeployed or removed from the patient.

In some examples, the lasso may be fixedly attached the prosthetic valve such that at least a portion of the lasso remains with the prosthetic valve after implantation.

Figure 30:
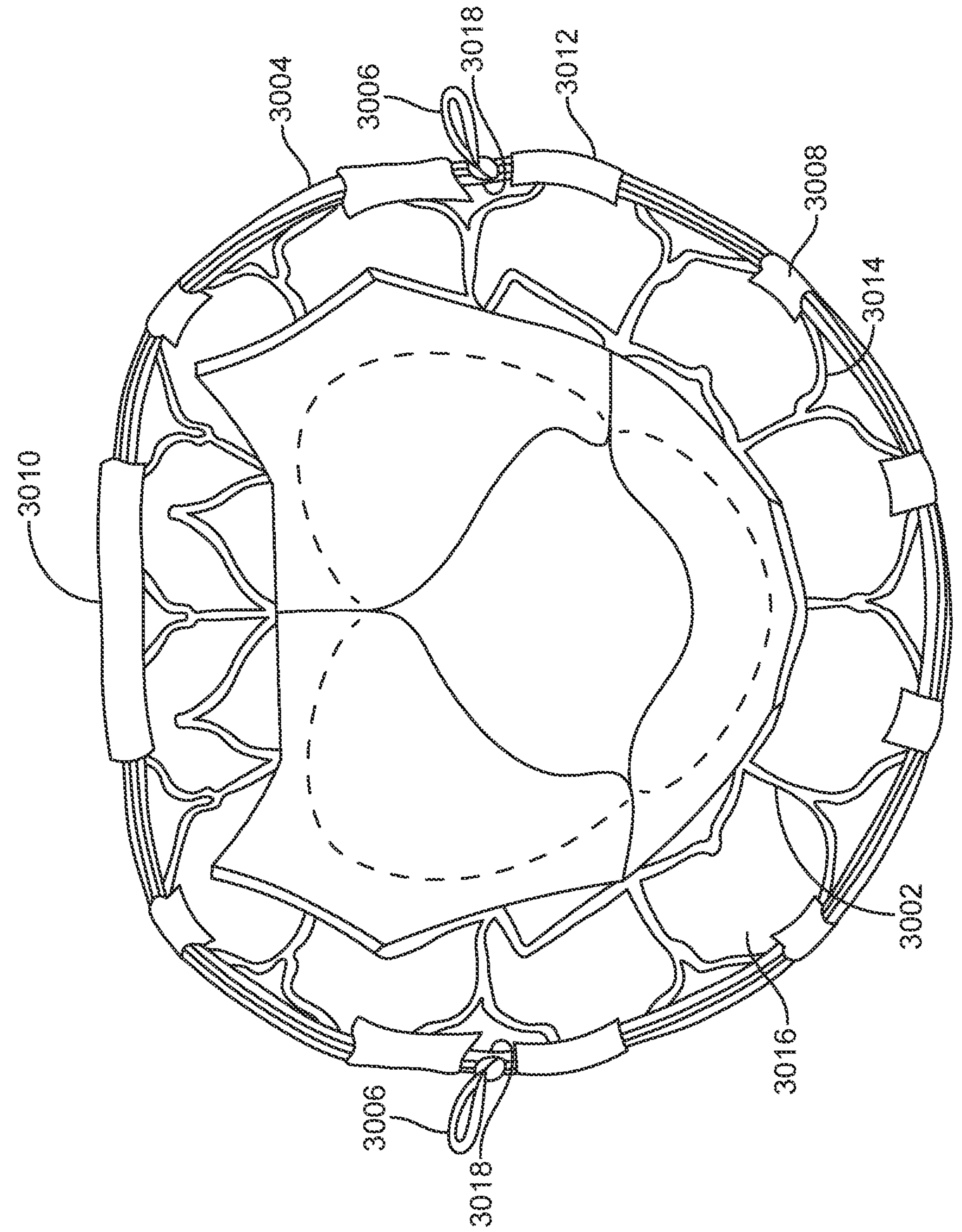
FIG. 30 illustrates another example of a lasso mechanism.

FIG. 30 illustrates another example of a lasso 3004 that is fixedly attached to the prosthetic valve 3002 which may be any of the prosthetic valves disclosed herein. Here, the lasso 3004 is attached to the perimeter of the atrial flange of the prosthetic valve. The lasso is formed from a single filament such as a wire or suture that forms a closed loop around the atrial flange. In other examples, more than one filament may be used to form the filament. One or more (here there are two) connectors 3006 such as loops are formed in the filament and extend outward and away from the lasso and provide an eyelet that may be releasably coupled to an actuation element such as a catheter shaft or tether. The lasso is fixed to the prosthetic valve by passing the filament through tabs 3010, 3008 coupled to the struts 3014 of the prosthetic valve or coupled to the covering 3016 (e.g. a Dacron cover) disposed over the struts 3014 of the prosthetic valve frame. The tabs may include short tabs 3008, or long tabs 3010. The long tabs 3012 may include a slot or open window portion 3018 to allow the connectors 3006 to extend through the slot or window to provide access to the looped portion of the connector. The looped portion of the connector may be formed by bunching a portion of the filament together and knotting it or crimping it with a crimping ring to form the loop which can act as an eyelet.

The lasso of FIG. 30 may be tensioned to collapse the atrial flange or tension may be reduced in order to permit the atrial flange to self-expand. Again, this allows controlled expansion of the atrial flange, or if desired the atrial flange may be collapsed, re-sheathed and repositioned or removed from the patient.

Figure 31C:
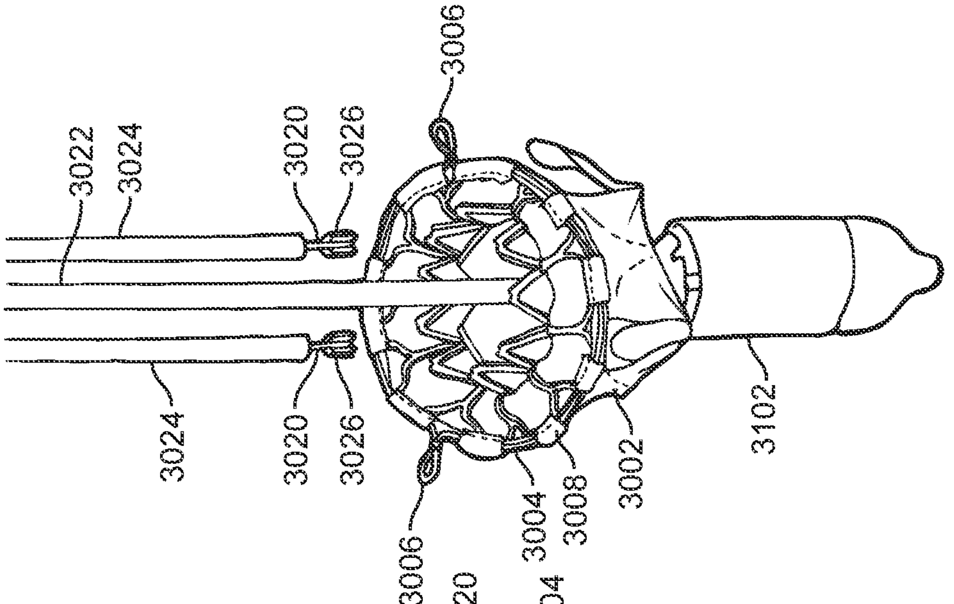
FIGS. 31A-31C show the prosthetic valve and lasso mechanism in FIG. 30 in the expanded and collapsed configurations.
Figure 31B:
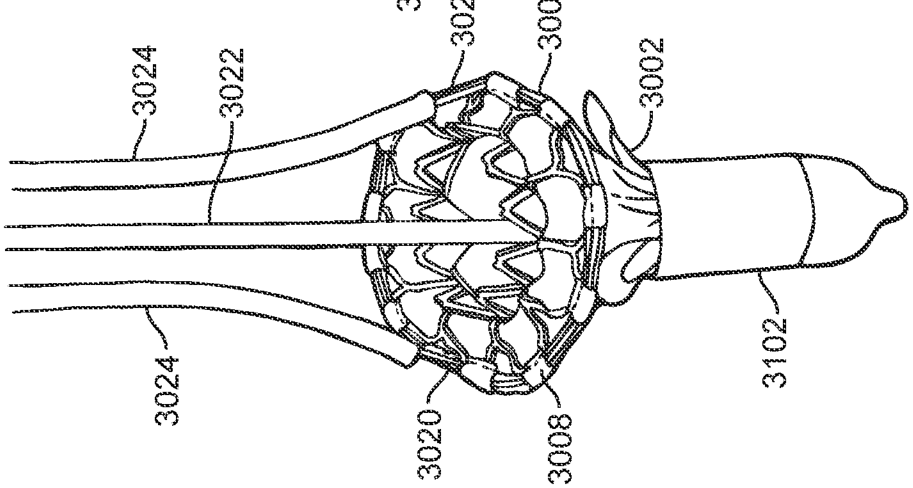
Figure 31A:
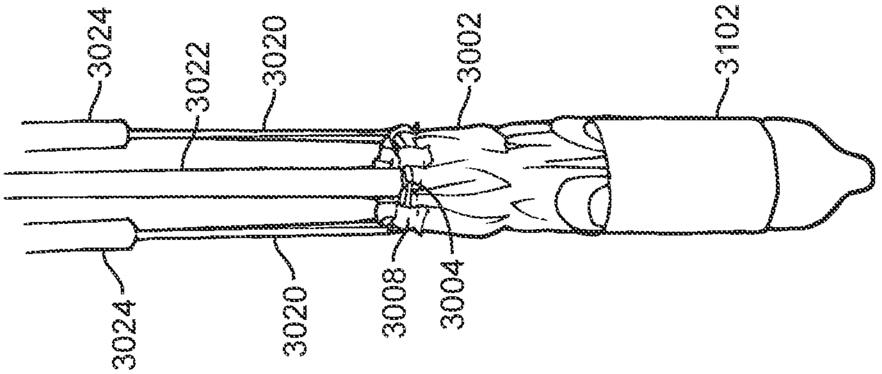

FIGS. 31A-31C illustrate the prosthetic valve of FIG. 30 in different configurations. FIG. 31A shows the prosthetic valve 3002 with tension applied to the lasso 3004 thereby collapsing the atrial flange into the collapsed configuration. The ventricular portion of the prosthetic valve is also in a collapsed configuration and housed in a capsule 3102. Tabs 3008 hold the lasso to the prosthetic valve 3002 as previously described. Two tethers 3020 are releasably coupled to the loops 3006 formed in the lasso (best seen in FIG. 31C). The tethers may be filaments such as wire or suture, and the tethers extend proximally substantially parallel to the longitudinal axis of the delivery catheter shaft 3022 which carries the prosthetic valve. The tethers may be housed in a lumen of another catheter shaft 3024 to prevent entanglement and control friction, or the tethers may simply run alongside the delivery catheter or in a lumen or annular space of the delivery catheter. The proximal ends of the tethers may be manually controlled by an operator or coupled to an actuator on a handle which can be actuated by an operator, thereby controlling the tension in the tethers and therefore controlling the expanded or collapsed configuration of the atrial flange.

FIG. 31B shows tension relaxed in the tethers 3020 thereby allowing the atrial flange to expand while the ventricular portion of the prosthetic valve remains collapsed or partially collapsed in the capsule 3102. If the operator needs to reposition the prosthetic valve or remove it from the patient, tension may be re-applied to the tethers to collapse the atrial flange so that it can be re-sheathed and repositioned or removed.

FIG. 31C shows the atrial flange fully expanded and once deployed correctly, the operator may remove all tension from the tethers 3020 and connectors 3026 are released from the loops 3006 in the lasso thereby decoupling the tethers from the lasso. The tethers 3020 and their protective sheaths 3024 may then be removed from the patient while the lasso 3004 remains attached to the prosthetic valve and implanted in the patient. The connectors may be any connector element which allows releasable coupling of the tethers with the loops, such as any of those described below.

Figure 31F:
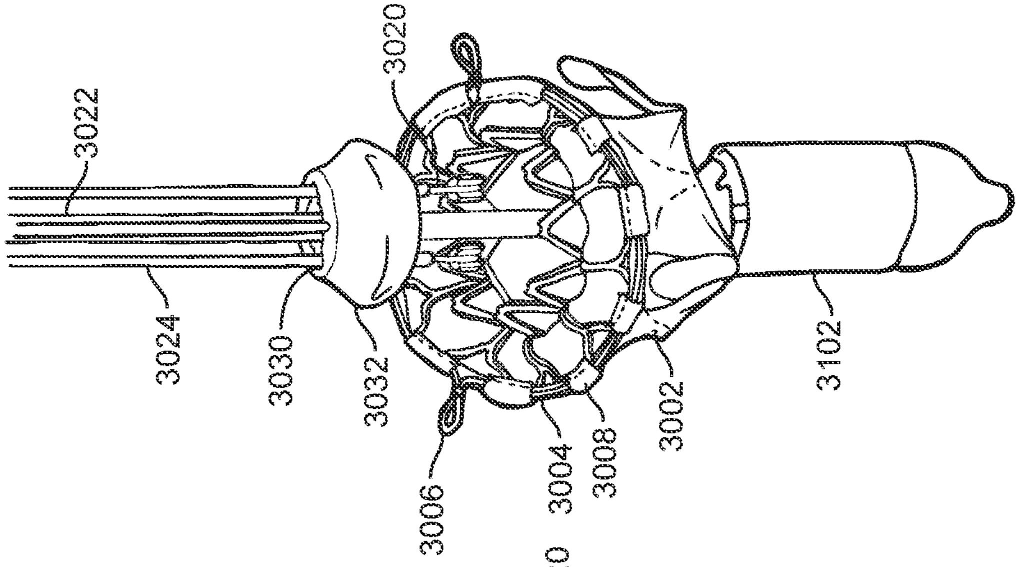
FIGS. 31D-31F show the prosthetic valve and lasso mechanism in FIGS. 31A-31C with a tether control element.
Figure 31E:
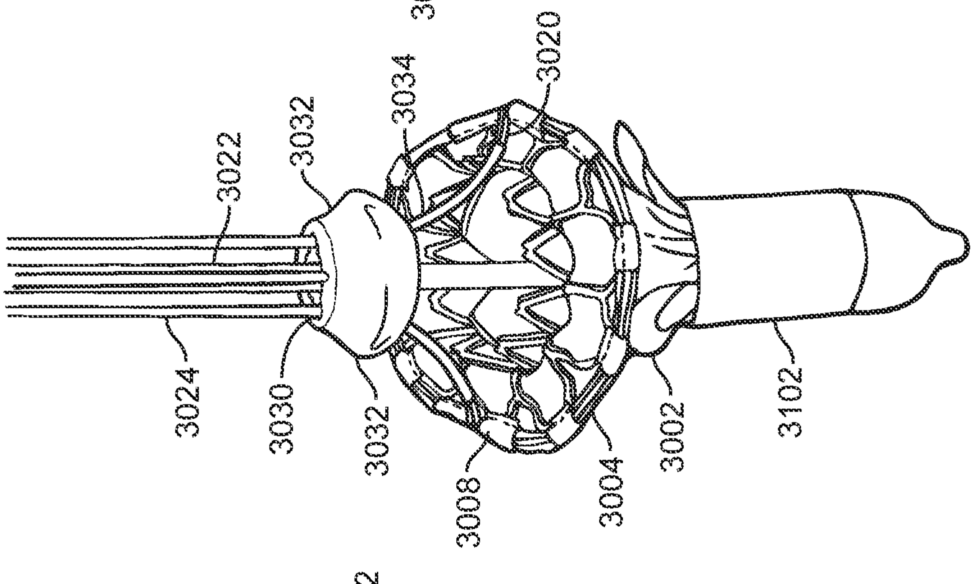
Figure 31D:
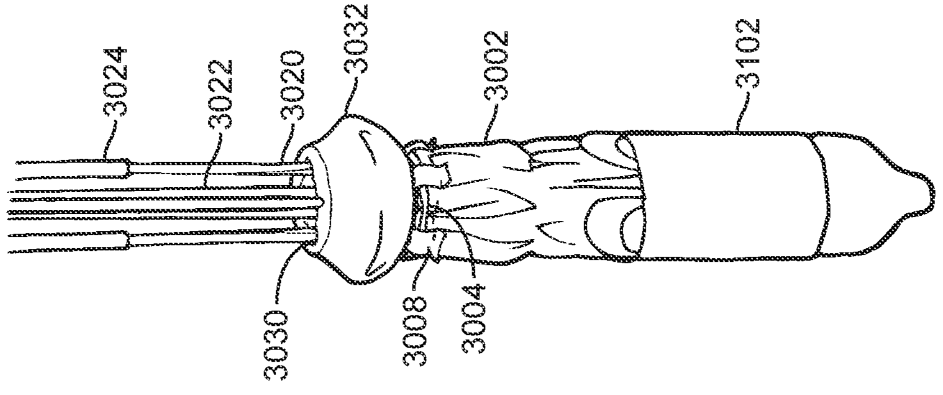

FIGS. 31D-31F illustrate a similar lasso deployment control mechanism as in FIGS. 31A-31C above, with the main difference being the tether control mechanism 3032 included. Other aspects of FIGS. 31D-31F are substantially the same as in FIGS. 31A-31C.

In FIG. 31D, tethers 3020, here three tethers, enter channels 3030 in a tether control element 3032 in a direction that is substantially parallel to the longitudinal axis of the delivery catheter 3022. The channels 3030 are formed so that the tethers exit the tether control element 3032 in a direction that is transverse or orthogonal to the longitudinal axis of the delivery catheter 3022. This helps prevent entanglement of the tethers and also directs tensile forces delivered to the lasso by the tethers to more radially inwardly directed to the lasso which will facilitate collapse of the lasso and atrial flange when tension is applied, as seen in FIG. 31D. The tether control element may have proximal and distal facing surfaces which are beveled to ensure that the tension control element does not get caught on any adjacent surfaces or cause any trauma to adjacent tissue which it may contact. Other aspects of FIG. 31D are substantially the same as FIG. 31A.

In FIG. 31E, the tension is released from the tethers, releasing the lasso and allowing the atrial flange to expand. Other aspects of FIG. 31E are generally the same as in FIG. 31B.

FIG. 31F shows the tethers 3020 released from the connector loops 3006 on the lasso. The tethers and connector element may then be removed from the patient. Other aspects of FIG. 31F are generally the same as in FIG. 31C.

Figures 31G, 31H, 31I:
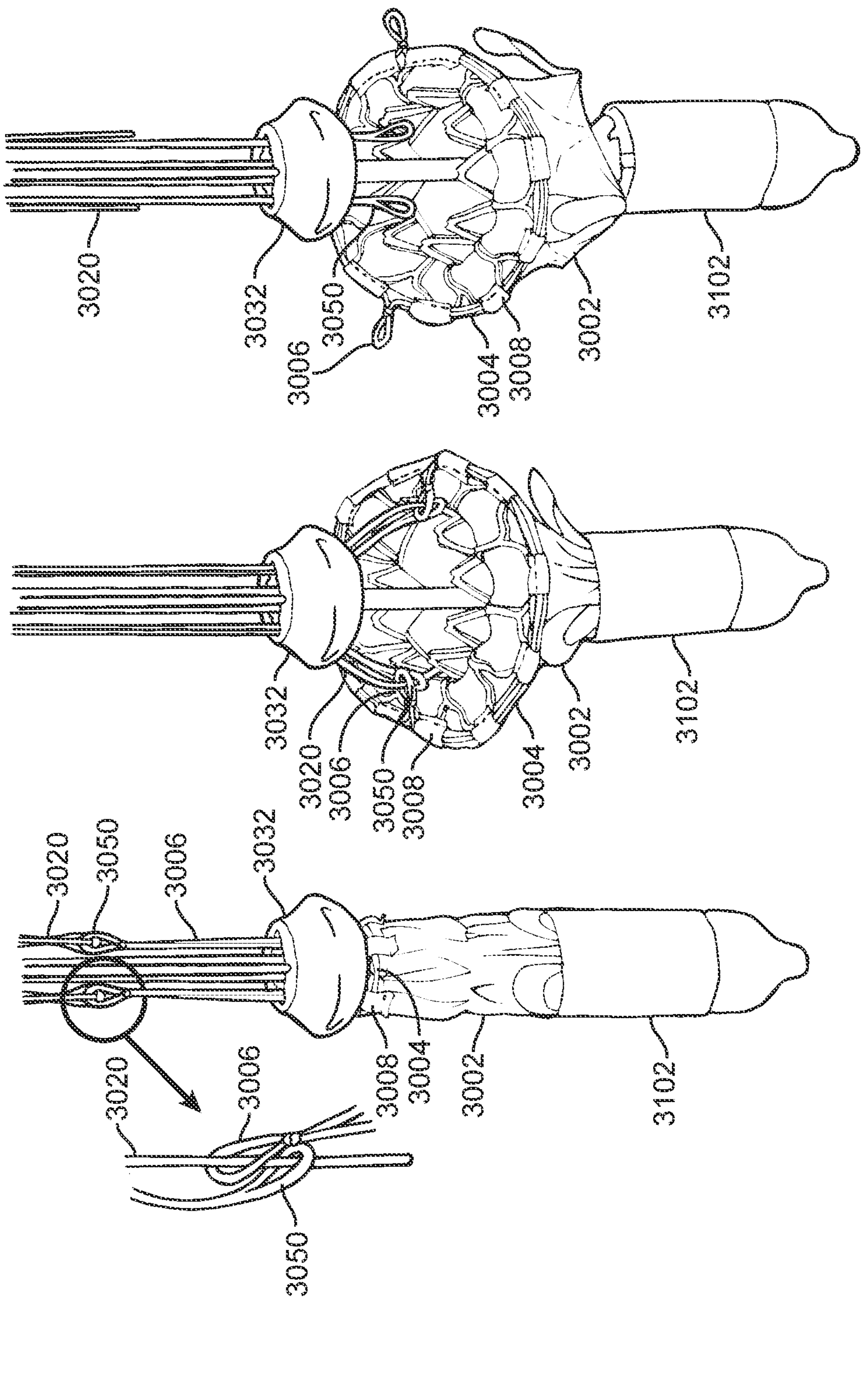
FIGS. 31G-31I show another example of a tether control element.

FIGS. 31G-31I illustrate another example of a mechanism that may be used to control actuation of a lasso such as in FIG. 30. FIGS. 31G-31I are generally the same as discussed with respect to FIGS. 31D-31F with the major difference being the coupling/uncoupling of the tethers to the loops in the lasso.

FIG. 31G shows the prosthetic valve 3002 which may be any of the valves disclosed herein, in a collapsed configuration with the ventricular portion disposed in a capsule 3102. A lasso 3004 passed around the perimeter of the atrial flange through tabs or eyelets 3008 coupled to the expandable frame or a cover over the frame, is tensioned to hold the atrial flange in a collapsed configuration. The loops 3006 connected to the tether extend through the tether control element 3032 so that the loops are superior to the tether control element 3032. The tether control element helps prevent entanglement of the various shafts and filaments as well as helping to direct forces provided by the tether as previously discussed above. A tether 3050 having a looped end is coupled to the lasso tether 3006 by disposing the tether 3050 loop under the loop 3006 of the lasso and a filament such as a wire 3020 is then passed through both loops. Thus, when tension is applied to the tether 3050, the loops remain interlocked because of the filament 3020 and the lasso may be tightened to collapse the atrial flange. The filament 3050 may extend alongside the delivery catheter or may be disposed in a lumen in a shaft or sheath (not illustrated). The tether 3050 and/or the shaft or sheath may run alongside the delivery catheter or be housed in a lumen or annular space of the delivery catheter.

When the operator desires to release tension in the lasso, tension may be released in the tether 3050 while it is still coupled to the lasso loop 3006 (the filament is still disposed in both tether loop and lasso loop). This allows the atrial flange to self-expand as seen in FIG. 31H. If the operator desires, tension may be re-applied and the atrial flange collapsed and then the valve may be repositioned and redeployed or removed from the patient.

FIG. 31I shows that once the prosthetic valve is correctly positioned and the atrial flange is expanded, the filament 3020 may be retracted proximally and removed from the loops 3006, 3050 decoupling the loops from one another. The loop 3006 on the lasso is coupled to the prosthetic valve and therefore remains implanted in the patient while the filament 3020 and tether 3050 are removed from the patient.

In any of the tether examples, the tethers coupled to the lasso may be disposed in a lumen of a shaft or sheath, or the tether may remain disposed free of any lumen and extend toward a proximal end of the delivery catheter. Any tether may only be a short segment of a tether that may also be joined to a catheter shaft that initiates the pulling action and controls tension and thus the actual tether segment does not have to extend all the way back to the proximal end of the delivery catheter.

Figure 32A:
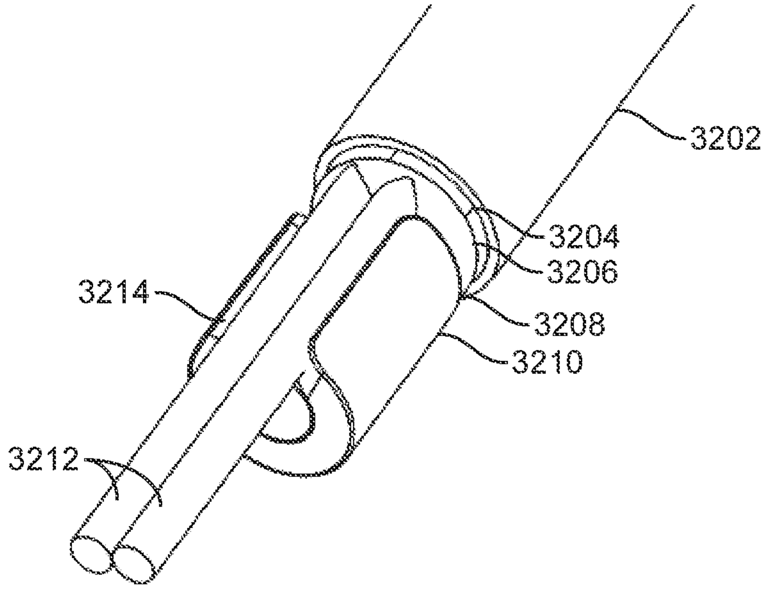
FIGS. 32A-32C illustrate examples of lasso connectors.
Figure 32B:
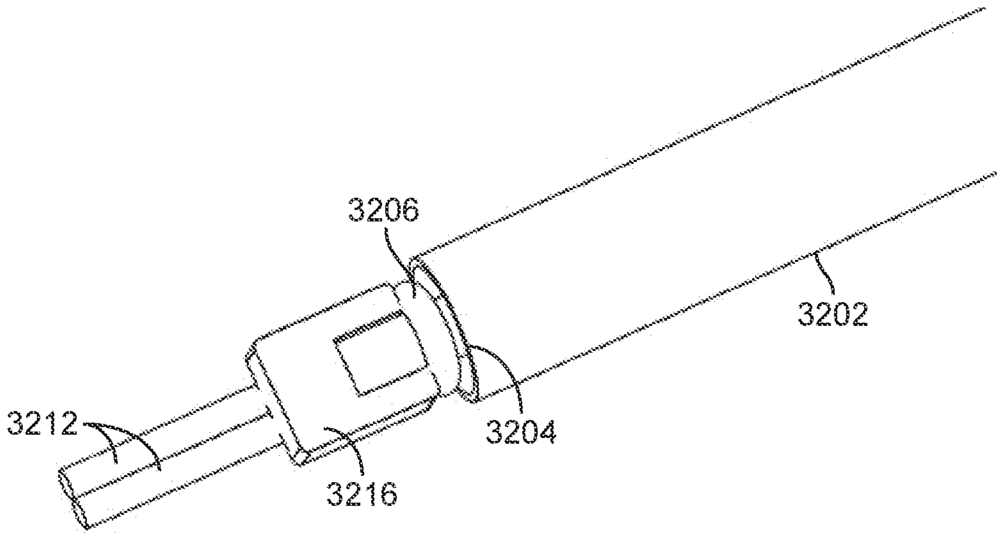
Figure 32C:
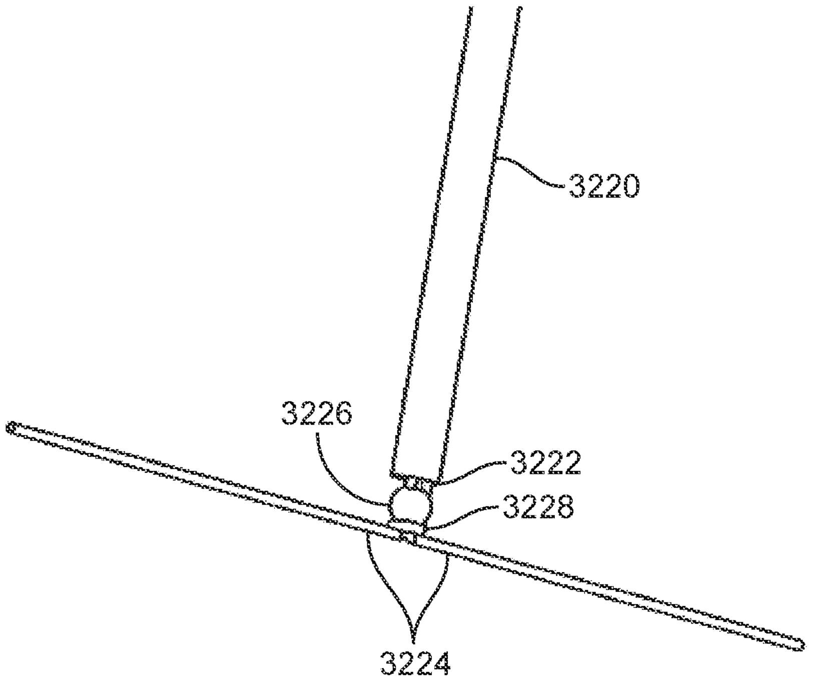

FIGS. 32A-32C illustrate examples of connectors which may be used to releasably couple a tether with any of the lasso examples disclosed above, such as in FIGS. 31A-31D. FIG. 32A shows a tether 3204 slidably disposed in a lumen of an outer shaft 3202 with a connector 3210 at the distal free end of the tether as previously described in FIG. 31C. The connector 3210 is a partially cylindrically shaped element with a shoulder region 3208 that extends radially outward from the tether to provide a region on which the loop 3206 of the lasso may rest without falling off and a grooved region 3214 extending along the longitudinal axis of the cylinder provides a channel in which both ends of tether 3212 may lie after looping around the shoulder region. When tension is applied to the loop, the loop will remain coupled to the connector. When tension is removed, the loop may be uncoupled from the connector element releasing the lasso from the tethers. The tension may be adjusted to vary the hoop stress applied to the lasso and this controls the speed of expansion or contraction, or the size of the atrial flange. The outer shaft 3202 may lie alongside the delivery catheter (not illustrated) or it may be disposed in a lumen or an annular region of the delivery catheter (also not illustrated).

FIG. 32B shows another example of a connector which may be used to releasably coupled the tether to the loops of a lasso. This example is similar to the example in FIG. 32A with the major difference being the connector 3216. Again, a tether 3204 is slidably disposed in a lumen of an outer catheter or shaft 3202. A connector 3216 is attached to the free end (distal end) of tether 3204. The connector is a rectangular block and therefore has a wide shoulder region on which the looped portion 3206 may lie when wrapped therearound and the opposite ends of the loop 3212 also lie flat against one side of the rectangular block connector. Other aspects of this example of connector a generally the same as previously described with respect to FIG. 32A.

FIG. 32C shows another example of a connector which may be used to releasably couple the tether to the lasso. In this example, the tether 3222 is a filament of wire or suture that passes through a lumen of outer shaft 3220. The tether 3222 then forms a loop 3228 and wraps around a ball connector 3226 that is attached to the lasso 3224. When tension is applied to tether 3222, the ball connector 3226 is pulled toward the distal end of the outer shaft 3220 preventing the loop 3228 in the tether from uncoupling from the ball, holding the lasso in a tensioned configuration. When tension on the tether 3222 is released, the loop 3228 maybe released from the ball connector 3226 releasing tension on the lasso 3224 and thereby allowing the atrial flange to open. Other aspects of this example of connector are generally the same as previously described in FIGS. 32A-32B.

In another example (not illustrated), the ball may be coupled to the tether 3222 and the loops 3006 (best seen in FIG. 31C) may be releasably coupled to the ball.

The lasso in these examples was applied to the atrial flange of the prosthetic valve. This is not intended to be limiting. The lasso may be applied to any one or more regions of the prosthetic valve to control expansion or collapse of one or more regions of the prosthetic valve. For example, a lasso may be applied to a ventricular portion of the prosthetic valve and the anchor tabs to control the radial distance between the free end of the anchor tab and the outer surface of the ventricular skirt of the prosthesis (sometimes also referred to as the tab elbow distance). This distance may be adjusted as a part of the manufacturing process, prior to delivery or after delivery to control tab contact with the adjacent tissue. Or the lasso may be applied to the ventricular skirt, or the annular region, or combinations of two or more regions of the prosthetic valve.

Figure 33A:
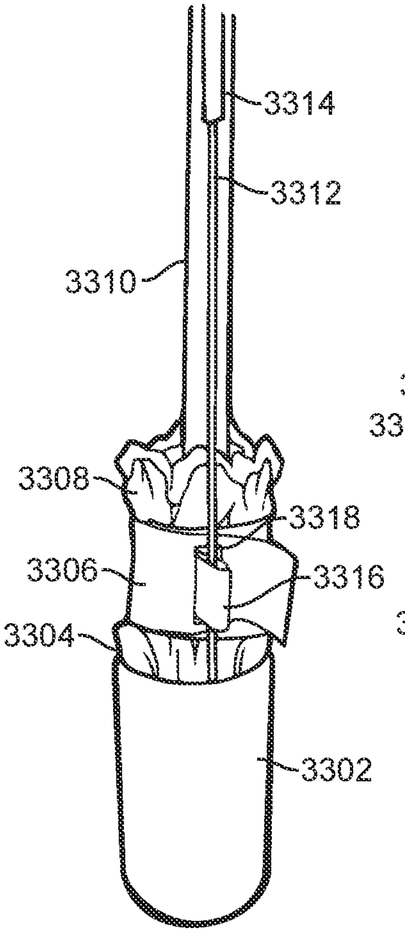
FIGS. 33A-33B illustrate a straitjacket control mechanism.
Figure 33B:
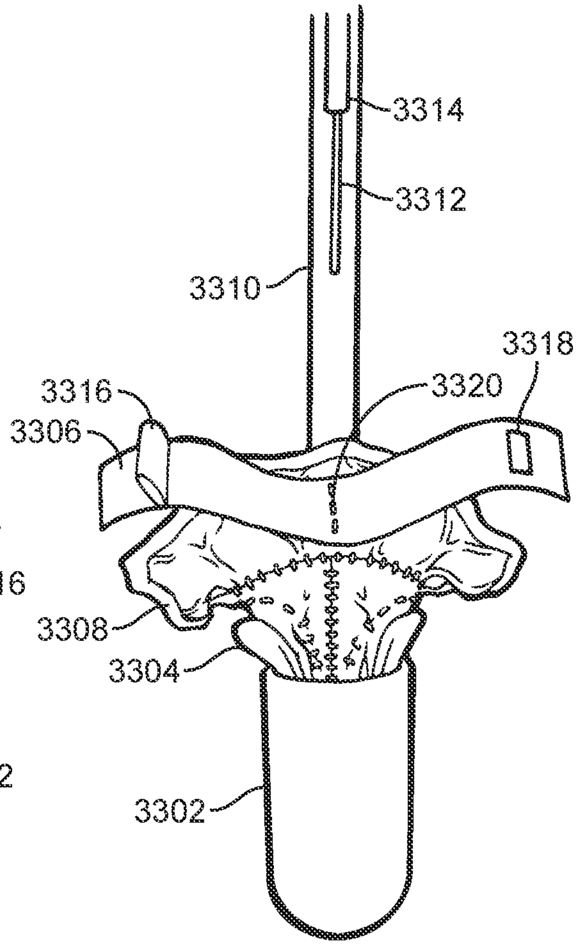

FIGS. 33A-33B illustrate another example of deployment control mechanism used control expansion of a prosthetic valve which may be any of the prosthetic valves disclosed herein, and any of which may be used as a prosthetic mitral valve.

In FIG. 33A, a prosthetic valve 3304 is in the collapsed configuration. The ventricular portion is collapsed and housed in a capsule 3302. The atrial portion 3308 is constrained and held in a collapsed configuration by a ribbon or straitjacket 3306 that is wrapped therearound. The straitjacket 3306 is an elongate ribbon that may have a length longer than the width such that the ratio of length to width is greater than one. A tab 3316 is formed in one end of the ribbon and a slot 3318 is formed in the other end of the ribbon. The straitjacket may be held in the locked configuration by passing the tab 3316 through the slot 3318, and then a wire, pin, or other filament 3312 is disposed in the tab to prevent it from slipping through the slot. When an operator wishes to release the straitjacket, the filament may be removed from the tab and then the tab will fall out of the slot, allowing release of the ends of the ribbon from one another so that the ribbon opens up, and this will release compression applied to the prosthetic valve such that the constrained region, here the atrial flange 3308 is then allowed to self-expand.

The pin or filament may be an elongate filament that extends proximally toward the proximal end of the delivery catheter 3310 where an operator can manually control the pin or filament. The filament may be coupled to an actuator on the proximal end of the delivery catheter that allows the operator to control the filament from a handle on the delivery catheter (not shown). The filament may be slidably disposed in a lumen of an outer shaft 3314 to prevent entanglement and control friction. The outer shaft 3314 may run alongside an outer surface of the delivery catheter 3310 or the outer shaft may be disposed in a lumen or annular space of the delivery catheter. In any example, the filament may run alongside the delivery catheter or in a lumen or annular space of the delivery catheter without the outer shaft 3314.

In FIG. 33B, the filament 3312 has been retracted proximally removing the filament from the looped tab 3316 allowing it to disengage from slot 3318 thereby releasing the straitjacket and opening so the atrial flange can self-expand while the ventricular portion remains collapsed by the capsule. The straitjacket may be sutured 3320 or otherwise attached to the prosthetic valve and therefore remains implanted with the prosthetic valve, or in any example the straitjacket may be removed from the patient. Once the atrial flange has deployed, the remainder of the prosthetic valve may be deployed similarly as previously described.

Figure 34A:
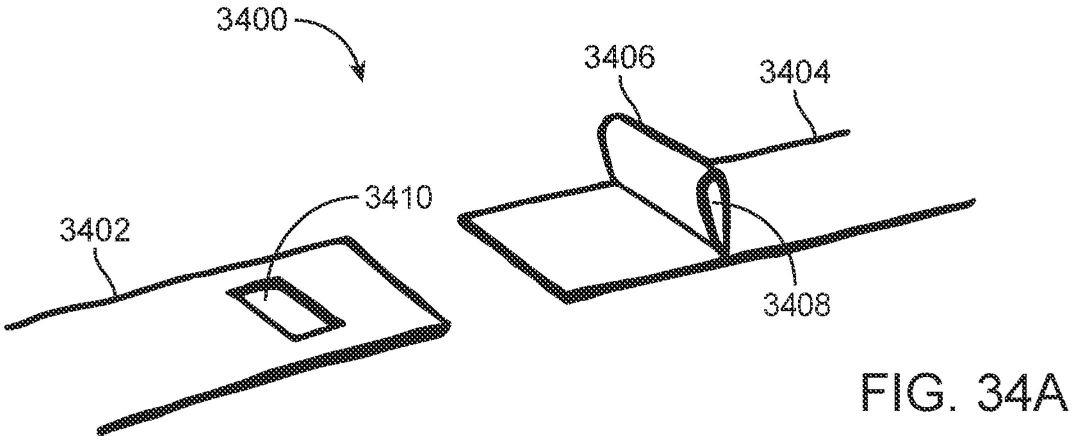
FIGS. 34A-34B illustrate the straitjacket in FIGS. 34A-34B.
Figure 34B:
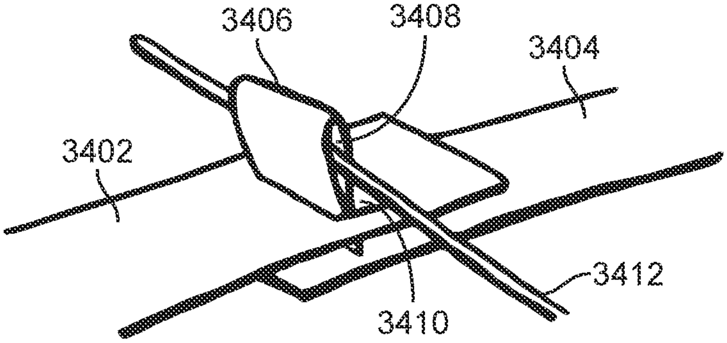

FIGS. 34A-34B illustrate the locking mechanism that may be used to hold the straitjacket of FIGS. 33A-33B. In FIG. 34A, the straitjacket 3400 includes a loop formed by joining opposite ends 3402, 3404 of a ribbon. One end 3402 includes a slotted region 3410 and the opposite end 3404 includes a tab 3406 with a channel 3408 extending through the tab. The slot is sized to receive the tab and the channel has a longitudinal axis which is transverse to or substantially orthogonal to the longitudinal axis of the ribbon.

In FIG. 34B, the opposite ends 3402, 3404 of the ribbon have been overlapped with one another and tab 3406 is inserted into slot 3410. Pin or filament 3412 is then inserted into channel 3408 locking the straitjacket into the closed position and constraining the prosthetic valve from self-expansion. When the operator is ready, the pin or filament 3412 may be removed from channel 3408 which releases the straitjacket and allowing the prosthetic valve to self-expand. The straitjacket may also be referred to as a belt or cinching element/mechanism.

The straitjacket may be disposed around any one or more regions of the prosthetic valve including the atrial flange, the annular region, the anchor tabs, the ventricular skirt, etc. It may be formed from any material including metals, fabrics such as Dacron, polymers, etc.

Optional Valve Body Configurations

The prosthetic valves previously described above may be modified to optionally include any of the following features which may facilitate delivery, deployment, or valve function.

For example, in any example of the valve body may be configured with a D-shaped cross-section to better fit the native valve anatomy. In still other examples, other cross-sectional shapes maybe desirable such as round, elliptical, square, rectangular, etc. to conform to, or anchor to the native anatomy.

Whether a D-shape or another shape, in some examples it may be desirable to form the prosthetic valve body so that upon expansion it does not engage the native valve annulus and thus anchoring is only accomplished via the upper atrial flange and the anchor tabs. Sizes of the anchoring elements may be adjusted to accommodate varying annular sizes. The valve body may have a perimeter that has a smaller diameter than the diameter of the perimeter of the native valve annulus. This may be advantageous for patients with small ventricles with degenerative mitral regurgitation (DMR) and a high ejection fraction.

Other expandable valve frame geometries may also provide advantages. For example, an expandable frame with fewer strut connection nodes reduces the amount of material in the prosthetic valve and thereby allows the valve frame to be collapsed into a lower profile which is desirable during delivery.

Figure 35:
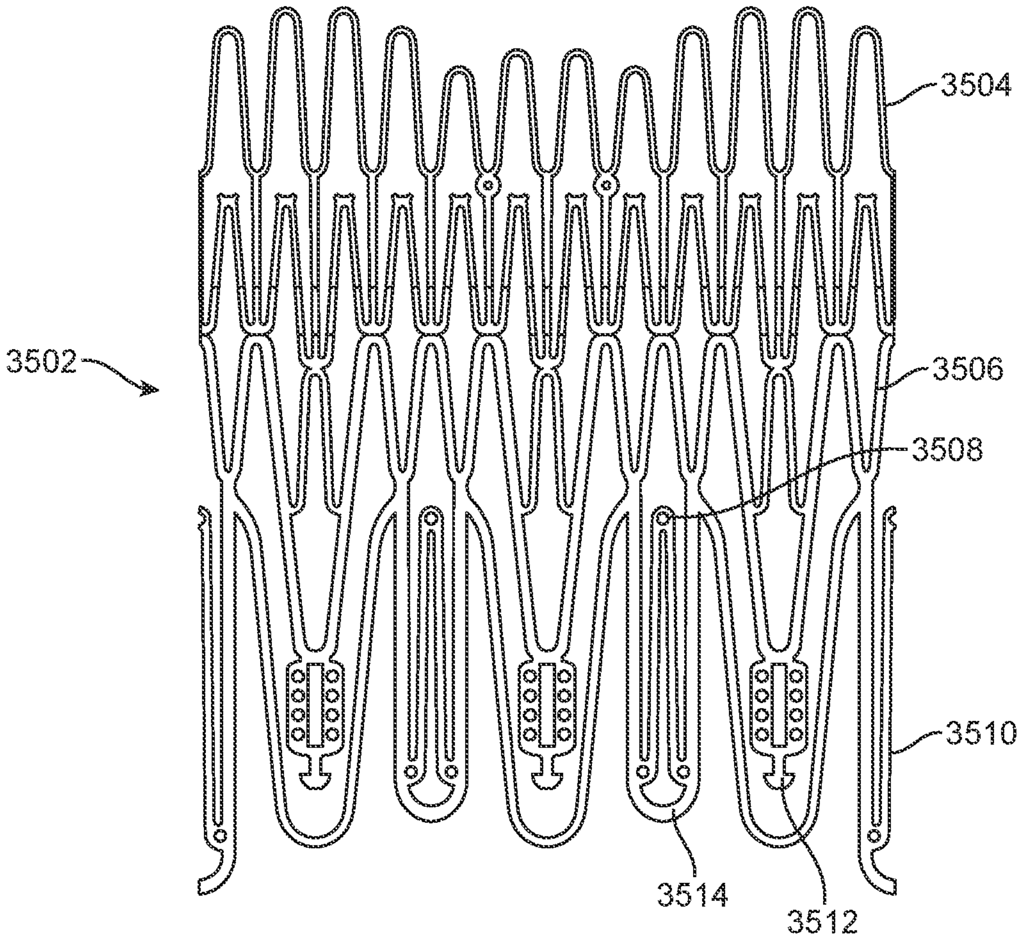
FIG. 35 illustrates an example of an expandable frame.

FIG. 35 shows an example of an expandable frame that can collapse into a smaller profile relative to earlier examples which not only helps with delivery of a smaller delivery system but also allows the frame to be more tightly crimped onto the delivery system ensuring safer delivery with less chance of the frame ejecting from the delivery system. The expandable frame 3502 generally takes the same form as previously described in other frames above, but has less metal forming the expandable frame and therefore collapses into a lower profile which facilitates delivery and also facilitates navigation through tortuous vessels. A reduced number of diamond shaped cells in the annular region allows for the reduced crimp. The smaller profile allows the frame to be more tightly crimped onto the delivery system ensuring safer delivery. Also, the lower profile allows a smaller percutaneous puncture to be used during introduction and delivery, thereby reducing the change of vascular trauma and bleeding and potentially speeding up sealing of the puncture site after the procedure.

The expandable frame 3502 includes an atrial region 3504, annular region 3506 and ventricular region 3510. The atrial region 3504 includes a plurality of elongate linear struts that are coupled together with a connector strut to form a sinusoidal pattern with peaks and valleys. The atrial region may be heat treated to form the atrial flange previously described above.

The annular region 3506 similarly is formed from a plurality of elongate linear struts coupled together with a connector to form a sinusoidal pattern with peaks and valleys. The annular region may be round and cylindrical or have a D-shaped cross-section, or any other cross-sectional shape. Linear connector struts join the atrial region with the annular region.

The ventricular region 3510 includes elongate linear struts connected together to form a sinusoidal pattern with peaks and valleys. Other aspects of the ventricular region are similar to those previously described in other examples of expandable frames. For example, the expandable frame includes commissure posts 3512 with enlarged mushroom shaped heads that releasably coupled the expandable frame with the delivery catheter, and also the commissure posts allow tissue or other material to be coupled to the commissure posts to form the prosthetic valve leaflets. In some examples, the commissure posts may have differently shaped connector heads on the anterior commissure posts to allow an operator to visualize under radiography or ultrasound the prosthetic valve orientation relative to the anatomy of the native valve. For example, the posterior commissure heads may be mushroom shaped while the anterior commissure posts may have trapezoidal shaped heads. Ventricular anchors 3508 such as anterior and/or posterior anchor tabs are also included in the expandable frame as well as a ventricular skirt 3514. In this example, the commissure posts are nested within struts that form the ventricular skirt. Moreover, the commissure posts do not extend past the edge of the ventricular skirt.

The frame design may also include commissure posts that are longer than the anchor tabs when crimped or collapsed onto the delivery system. This simplifies attachment to the delivery catheter and reduces the depth of contact between the commissure posts and the delivery system.

Figure 36:
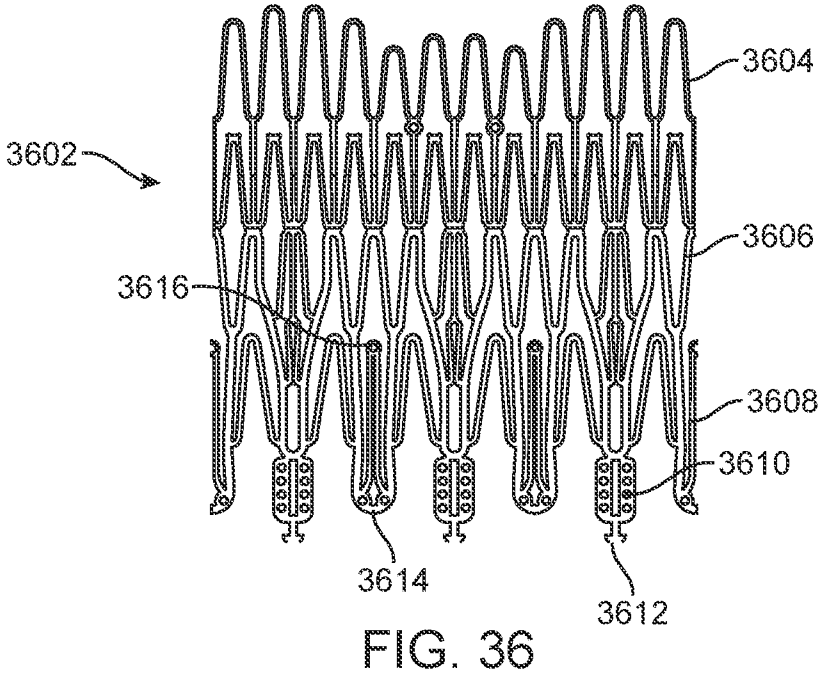
FIG. 36 illustrates another example of an expandable frame.

FIG. 36 illustrates an example of an expandable frame 3602 with commissure posts 3610 that extend past the edge of the ventricular skirt 3614. This example shows the anchoring tabs 3616 axially shorter than the commissure posts 3610. Also, the commissure posts are no longer encircled by adjacent struts (ventricular arches) to simplify anchoring to the delivery system since the anchoring points are now at the furthest end of the frame. Also removed are the "S" bars. Only the support bars remain which attach directly to the commissure rail in this example. The overall shorter design (the removal of the eyelets also helps) also improves navigation of the device through tight anatomy. The removal of the ventricular arches also removes bulk near the anchoring points in the crimp state. Also, the mounting of the valve to the delivery system is more easily visualized without the arches. Other aspects of the anchor frame 3602 are generally the same as described in FIG. 35 including the atrial portion 3604 which forms an atrial flange, the annular region 3606, and the ventricular region 3608. Each of these regions includes elongate struts coupled together to form a sinusoidal pattern with peaks and valleys. The regions are coupled together with connector struts.

As disclosed previously, enlarged mushroom head regions 3612 on the commissure posts allow the prosthesis to be disposed in recessed or slotted regions on the delivery system. An outer catheter is slidably disposed over the commissure posts thereby constraining the commissure posts in the catheter recesses and releasably engaging the prosthesis to the delivery system. Retraction of the outer catheter allows the commissure posts to be released from the recessed regions of the delivery system thereby uncoupling the prosthesis from the delivery catheter. In some examples, the free ends of the commissure posts with or without enlarged mushroom heads maybe angled radially inward or radially outward to facilitate prosthesis loading onto the delivery system and to help prevent premature release. Angling of the commissure posts also may impact valve sealing, left ventricular outflow tract (LVOT) obstruction, as well as providing desirable mechanical properties to the prosthetic valve frame. Additional disclosure regarding angle commissure posts may be found below.

Also, as previously disclosed, the connectors heads 3612 on the commissure posts 3610 may be mushroom heads, or they may be different from one another. For example, the anterior commissure head may have one shape (e.g. trapezoidal) while the posterior commissure heads may have a different shape so that the operator can determine the orientation of the prosthesis during delivery by visualizing the prosthesis with radiographic or ultrasound techniques.

A porous valve may also be helpful since this allows a seal to form more gradually over time rather than instantaneously upon implantation because leaking allows compliance initially. A mesh or porous material may be coupled to the ventricular skirt and flow is reduced progressively over time as tissue in grows into the mesh material.

A reduced ventricular skirt may also be employed to allow for washout. This may be accomplished by leaving some or all of the ventricular skirt uncovered and this helps prevent blood flow stasis thereby permitting more natural blood flow through the prosthetic valve and avoids or minimizes thrombus formation.

Similarly, PTFE, ePTFE, or other materials maybe coupled to various portions of the prosthetic valve to help inhibit thrombus formation and growth. For example, PTFE may be disposed along or adjacent the prosthetic leaflets including adjacent the region where the prosthetic leaflet is coupled to the commissure posts and/or expandable frame. Anti-thrombus agents may also be coupled to the prosthetic valve and delivered or eluted therefrom the reduce thrombus formation.

In still other examples the prosthetic valve leaflets may include one or two or more mobile leaflets and one or two or more stationary leaflets. The stationary leaflets may be easier to design. Prosthetic leaflet height during closing may also be easier to control. The mobility of the prosthetic leaflets may also be controlled either all together or each with a unique mobility.

In any example, it may be desirable to provide commissure posts that are angled radially inward. This may help with flow dynamics as the blood or other fluid passes through the prosthetic valve leaflets which are attached to the commissures.

Figure 37:
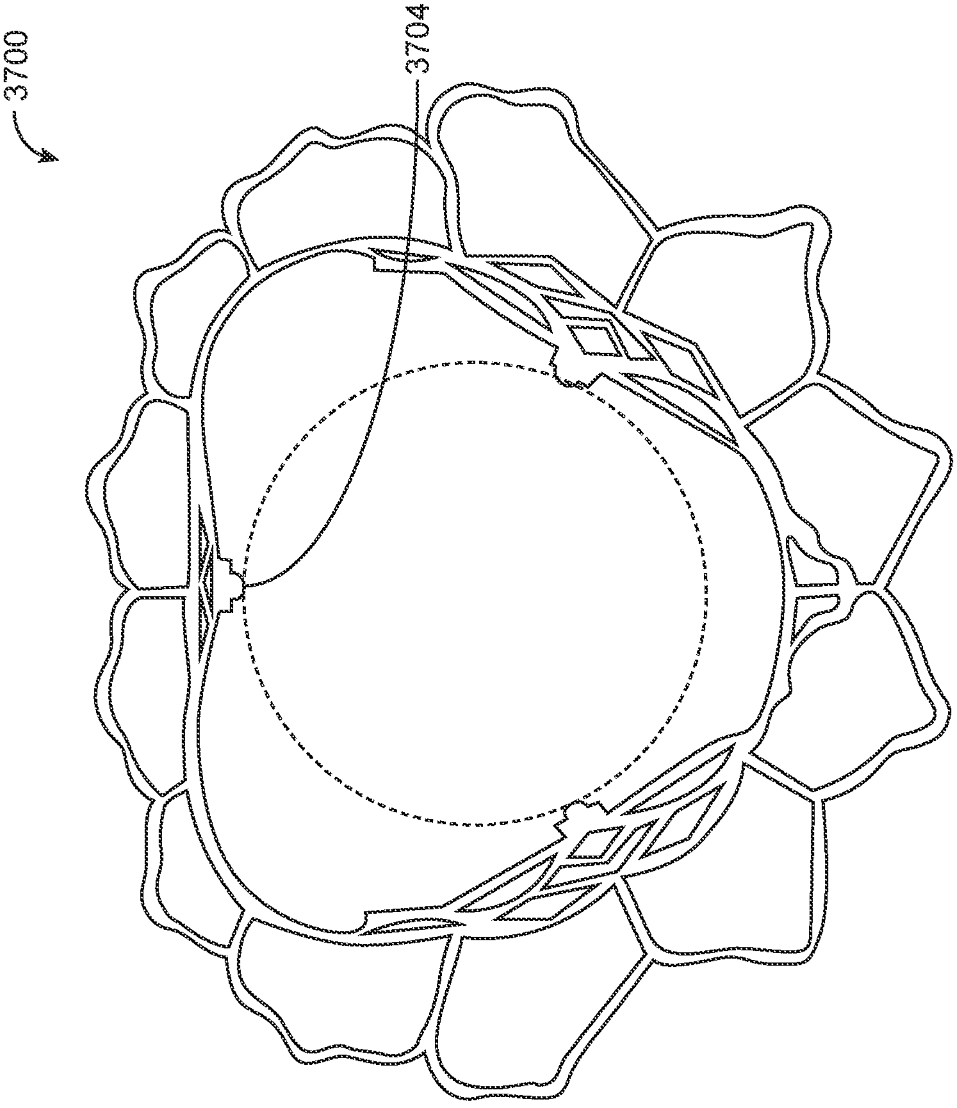
FIG. 37 shows an example of an expandable frame with angled commissure posts.

FIG. 37 shows a prosthetic valve 3700 with commissure posts 3704 angled radially inward so that it is orthogonal to or transverse to the longitudinal axis of the prosthetic valve. Each post may be angled inwardly in equal amounts so that a circular line is tangent to the tips of each post, or the posts may be bent in differing amounts. In other examples, the commissure posts may be angled outwardly, or some commissure posts may be angled inwardly and some angled outwardly. In still other examples, any permutation or combination of commissure posts angled inwardly, angled outwardly, or remaining straight and substantially parallel with the longitudinal axis of the prosthetic valve frame may be used. For example, in one example one or more posterior commissure posts may be straight and substantially parallel with the longitudinal axis of the prosthetic valve frame, while the prosthetic valve also has one or more anterior commissure posts which are angled radially outward (the angled commissure post is orthogonal to or transverse to the longitudinal axis of the valve). In any example, some or all of the commissure posts may be parallel with the longitudinal axis of the prosthetic valve or the commissure posts maybe curvilinear relative to the longitudinal axis of the prosthetic valve. Thus, any variation of commissure posts may be transverse to or orthogonal to the valve longitudinal axis, or parallel, or curvilinear thereto. Commissure angle can be used to impact effective orifice area, ease of valve loading, radial force to facilitate valve sealing, potential LVOT obstruction, valve hydrodynamic performance and frame mechanical properties, and therefore angle may be adjusted during manufacturing or the commissure angle may be adjusted during implantation in a patient to provide desired performance characteristics.

NOTES AND EXAMPLES

The following, non-limiting examples, detail certain aspects of the present subject matter to solve the challenges and provide the benefits discussed herein, among others.

While the present disclosure focuses on the use of a prosthetic valve for treating mitral regurgitation, this is not intended to be limiting. The prosthetic valves disclosed herein may also be used to treat other body valves including other heart valves or venous valves. Examples of heart valves include the aortic valve, the tricuspid valve, or the pulmonary valve.

Example 1 is a prosthetic valve comprises a radially expandable frame comprising an atrial flange, a ventricular skirt, an annular region, and a ventricular anchor tab, wherein the atrial flange is disposed on one end of the expandable frame and the ventricular skirt is disposed on an opposite end of the expandable frame, wherein the annular region is disposed between the atrial flange and the ventricular skirt, wherein the anchor tab is coupled to the ventricular skirt; and a constraining element coupled to the expandable frame, the constraining element configured to apply a hoop force to the expandable frame thereby controlling an amount of expansion or an amount of collapse of the expandable frame.

Example 2 is the valve of Example 1, wherein the constraining element is an adjustable constraining element configured to apply an adjustable hoop force to the expandable frame.

Example 3 is the valve of any of Examples 1-2, wherein the adjustable constraining element comprises a lasso disposed around a perimeter of the atrial flange.

Example 4 is the valve of any of Examples 1-3, wherein the expandable frame comprises a plurality of eyelets coupled to the perimeter of the atrial flange, and wherein the lasso is slidably disposed through the plurality of eyelets.

Example 5 is the valve of any of Examples 1-4, wherein the lasso comprises one or more elongate tethers coupled to the lasso, and wherein actuation of the one or more elongate tethers applies or releases the hoop force, thereby causing the atrial flange to expand or collapse.

Example 6 is the valve of any of Examples 1-5, wherein the constraining element is fixedly attached to the expandable frame.

Example 7 is the valve of any of Examples 1-6, wherein the constraining element is releasably attached to the expandable frame.

Example 8 is the valve of any of Examples 1-7, wherein the constraining element comprises a straitjacket disposed around a perimeter of the atrial flange.

Example 9 is the valve of any of Examples 1-8, wherein the straitjacket comprises a first free end and a second free end opposite the first free end, wherein the first free end comprises a slot and the second free end comprises an eyelet protruding outward, and wherein the eyelet is disposed in the slot, such that when an elongate tether is releasably and slidably disposed in the eyelet the straitjacket is held in a closed loop that constrains expansion of the atrial flange, and wherein removal of the elongate tether from the eyelet allows the straitjacket to open and permit expansion of the atrial flange.

Example 10 is the valve of any of Examples 1-9, wherein the constraining element is disposed over the ventricular anchor tab and the ventricular skirt, and wherein adjustment of the hoop force controls a radial distance between the ventricular anchor tab and the ventricular skirt.

Example 11 is the valve of any of Examples 1-10, further comprising a tether having a first end and a second end opposite the first end, wherein the first end is coupled to the constraining element, and wherein the second end is configured to be carried in or alongside a delivery catheter carrying the prosthetic valve, and wherein the second end is configured to be actuated or manipulated by an operator.

Example 12 is a prosthetic valve system comprising the prosthetic valve of any of Examples 1-11; a delivery catheter having a longitudinal axis and carrying the prosthetic valve; and a tether coupled to the constraining element, wherein the tether runs axially along the longitudinal axis of the delivery catheter, and wherein actuation of the tether controls the hoop force applied to the expandable frame.

Example 13 is the system of Example 12, wherein the tether is releasably coupled to the constraining element.

Example 14 is a method of delivering a prosthetic valve to a treatment area in a patient, the method comprising: providing a prosthetic valve having a radially expandable frame, the radially expandable frame comprising an atrial flange, a ventricular skirt, an annular region disposed between the atrial flange and the ventricular skirt, and a ventricular anchor tab coupled to the ventricular skirt; causing a hoop force to be applied to the prosthetic valve with a constraining element that holds at least a portion of the prosthetic valve in a collapsed configuration; advancing the prosthetic valve to the treatment area in the collapsed configuration; adjusting the hoop force and allowing the portion of the prosthetic valve to radially expand; and anchoring the prosthetic valve to tissue in the treatment area.

Example 15 is the method of Example 14, wherein the constraining element comprises a lasso, and wherein causing the hoop force to be applied to the prosthetic valve comprises maintaining the lasso securely around the prosthetic valve.

Example 16 is the method of any of Examples 14-15, wherein maintaining the lasso comprises tensioning a tether coupled to the lasso.

Example 17 is the method of any of Examples 14-16, wherein adjusting the hoop force comprises loosening the lasso.

Example 18 is the method of any of Examples 14-17, wherein loosening the lasso comprises reducing tension in a tether coupled to the lasso or decoupling the tether from the lasso.

Example 19 is the method of any of Examples 14-18, wherein the constraining element comprises a straitjacket, and wherein causing the hoop force to be applied to the prosthetic valve comprises maintaining the straitjacket around the prosthetic valve.

Example 20 is the method of any of Examples 14-19, wherein adjusting the hoop force comprises loosening the straitjacket.

Example 21 is the method of any of Examples 14-20, wherein loosening the straitjacket comprises decoupling a tether from the straitjacket.

Example 22 is the method of any of Examples 14-21, further comprising applying a second hoop force to the prosthetic valve after adjusting the hoop force, thereby collapsing the prosthetic valve.

Example 23 is the method of any of Examples 14-22, wherein the constraining element is coupled to the atrial flange.

Example 24 is a prosthetic valve comprising a radially expandable frame comprising an atrial flange, a ventricular skirt, an annular region disposed between the atrial flange and the ventricular skirt, and a ventricular anchor tab, wherein the atrial flange is disposed on one end of the expandable frame and the ventricular skirt is disposed on an opposite end of the expandable frame, wherein the ventricular anchor tab is coupled to the ventricular skirt, and wherein the ventricular anchor tab comprises an atraumatic tip or a tip that is echogenic when visualized with ultrasound or radiopaque when visualized with radiography.

Example 25 is the valve of Example 24, wherein the tip is an echogenic tip formed from an echogenic material, or wherein the echogenic tip comprises an echogenic material coupled to the anchor tab, or wherein the echogenic tip is formed from surface features disposed on the anchor tab that impart echogenicity thereto.

Example 26 is the valve of any of Examples 24-25, wherein the atraumatic tip comprises a polymer or other material coupled to the anchor tab and configured to engage tissue in the heart without piercing the tissue.

Example 27 is the valve of any of Examples 24-26, further comprising an atraumatic tip coupled to the anchor tab, the atraumatic tip having a greater surface area relative to the anchor tab without the atraumatic tip, the atraumatic tip configured to distribute anchoring forces over a larger surface area thereby reducing or eliminating trauma to tissue in which the atraumatic tip anchors.

Example 28 is the valve of any of Examples 24-27, wherein the atraumatic tip comprises a self-expanding tip having an expanded configuration and a collapsed configuration, wherein the atraumatic tip is biased to remain in the expanded configuration and the atraumatic tip is held in the collapsed configuration with a constraint, and wherein in the expanded configuration the atraumatic tip is configured to engage tissue without piercing the tissue, and wherein in the collapsed configuration the valve has a profile configured for delivery to the heart.

Example 29 is the valve of any of Examples 24-28, wherein the atraumatic tip comprises a spiral torsion spring.

Example 30 is the valve of any of Examples 24-29, wherein the atraumatic tip comprises one or more slots or apertures disposed in the atraumatic tip to increase flexibility thereof.

Example 31 is the valve of any of Examples 24-30, further comprising a plurality of commissure posts coupled to the expandable frame, the plurality of commissure posts configured to hold a plurality of prosthetic valve leaflets, and wherein one or more of the plurality of commissure posts are transverse to a longitudinal axis of the radially expandable frame.

Example 32 is the valve of any of Examples 24-31, further comprising a plurality of commissure posts coupled to the expandable frame, one or more of the plurality of commissure posts adjustably angulatable relative to a longitudinal axis of the radially expandable frame.

Example 33 is a prosthetic valve comprising a radially expandable frame comprising an atrial flange, a ventricular skirt, an annular region disposed between the atrial flange and the ventricular skirt, a ventricular anchor tab, and a plurality of commissure posts, wherein the atrial flange is disposed on one end of the expandable frame and the ventricular skirt is disposed on an opposite end of the expandable frame, wherein the ventricular skirt has a ventricular edge that is the downstream-most edge of the prosthetic valve, wherein the ventricular anchor tab is coupled to the ventricular skirt, and wherein the plurality of commissure posts comprise a free end and a connected end, the connected end coupled to the expandable frame, and wherein the free end extends beyond the ventricular edge of the ventricular skirt.

Example 34 is the valve of Example 33, wherein the prosthetic valve is a prosthetic mitral valve.

Example 35 is the valve of any of Examples 33-34, wherein the commissure posts comprise a coupling element on the free end, the coupling element configured to releasably engage the prosthetic valve with a delivery catheter.

Example 36 is the valve of any of Examples 33-35, wherein one or more of the plurality of commissure posts are transverse to a longitudinal axis of the radially expandable frame.

Example 37 is the valve of any of Examples 33-36, wherein at least one of the plurality of commissure posts is adjustably angulatable relative to a longitudinal axis of the radially expandable frame.

Example 38 is the valve of any of Examples 33-37, wherein at least one coupling element is a radiopaque marker configured to allow an operator to visualize an anterior portion of the prosthetic valve with radiographic imaging.

In Example 39, the apparatuses or methods of any one or any combination of Examples 1-38 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A prosthetic valve comprising:

a radially expandable frame comprising an atrial flange, a ventricular skirt, an annular region, and a ventricular anchor tab, wherein the atrial flange is disposed on one end of the expandable frame and the ventricular skirt is disposed on an opposite end of the expandable frame, wherein the annular region is disposed between the atrial flange and the ventricular skirt, wherein the ventricular anchor tab is coupled to the ventricular skirt; and a straitjacket disposed around a perimeter of the atrial flange and configured to apply a hoop force to the expandable frame thereby controlling an amount of expansion or an amount of collapse of the expandable frame, wherein the straitjacket comprises a first free end that comprises a slot and a second free end opposite the first free end, the second free end comprising an eyelet protruding outward and disposed in the slot, wherein, when a tether is releasably and slidably disposed in the eyelet, the straitjacket is held in a closed loop that constrains expansion of the atrial flange, and wherein removal of the tether from the eyelet allows the straitjacket to open and permit expansion of the atrial flange.

2. The prosthetic valve of claim 1, wherein the straitjacket is configured to apply an adjustable hoop force to the expandable frame.

3. The prosthetic valve of claim 1, wherein the straitjacket is fixedly attached to the expandable frame.

4. The prosthetic valve of claim 1, wherein the straitjacket is releasably attached to the expandable frame.

5. The prosthetic valve of claim 1, further comprising the tether, wherein the tether has a first end coupled to the straitjacket and a second end opposite the first end, wherein the second end is configured to be carried in or alongside a delivery catheter carrying the prosthetic valve, and wherein the second end is configured to be actuated or manipulated by an operator.

6. A prosthetic valve system, comprising: the prosthetic valve of claim 1; a delivery catheter having a longitudinal axis and carrying the prosthetic valve; and the tether, wherein the tether is coupled to the straitjacket and runs axially along the longitudinal axis of the delivery catheter, and wherein actuation of the tether controls the hoop force applied to the expandable frame.

7. The prosthetic valve system of claim 6, wherein the tether is releasably coupled to the straitjacket.

8. A prosthetic valve comprising:

a radially expandable frame comprising an atrial flange, a ventricular skirt, an annular region, and a ventricular anchor tab, wherein the atrial flange is disposed on one end of the expandable frame and the ventricular skirt is disposed on an opposite end of the expandable frame, wherein the annular region is disposed between the atrial flange and the ventricular skirt, wherein the ventricular anchor tab is coupled to the ventricular skirt; and a straitjacket disposed around a perimeter of the atrial flange and configured to apply a hoop force to the expandable frame thereby controlling an amount of expansion or an amount of collapse of the expandable frame, wherein the straitjacket is disposed over the ventricular anchor tab and the ventricular skirt, wherein adjustment of the hoop force controls a radial distance between the ventricular anchor tab and the ventricular skirt, wherein the straitjacket comprises a first free end that comprises a slot and a second free end opposite the first free end, the second free end comprising an eyelet protruding outward and disposed in the slot, wherein, when a tether is releasably and slidably disposed in the eyelet, the straitjacket is held in a closed loop that constrains expansion of the atrial flange, and wherein removal of the tether from the eyelet allows the straitjacket to open and permit expansion of the atrial flange.

9. The prosthetic valve of claim 8, wherein the straitjacket is fixedly attached to the expandable frame.

10. The prosthetic valve of claim 8, wherein the straitjacket is releasably attached to the expandable frame.

11. The prosthetic valve of claim 8, further comprising the tether, wherein the tether has a first end coupled to the straitjacket and a second end opposite the first end, wherein the second end is configured to be carried in or alongside a delivery catheter carrying the prosthetic valve, and wherein the second end is configured to be actuated or manipulated by an operator.

12. A prosthetic valve system, comprising: the prosthetic valve of claim 8; a delivery catheter having a longitudinal axis and carrying the prosthetic valve; and the tether, wherein the tether is coupled to the straitjacket and runs axially along the longitudinal axis of the delivery catheter, wherein actuation of the tether controls the hoop force applied to the expandable frame, and wherein the tether is releasably coupled to the straitjacket.

13. A prosthetic valve, comprising:

a radially expandable frame comprising an atrial flange, a ventricular skirt, an annular region disposed between the atrial flange and the ventricular skirt, a ventricular anchor tab, and a plurality of commissure posts, wherein the atrial flange is disposed on one end of the expandable frame and the ventricular skirt is disposed on an opposite end of the expandable frame, wherein the ventricular skirt has a ventricular edge that is a downstream-most edge of the prosthetic valve, wherein the ventricular anchor tab is coupled to the ventricular skirt, and wherein the plurality of commissure posts comprises a free end and a connected end, the connected end coupled to the expandable frame, and wherein the free end extends beyond the ventricular edge of the ventricular skirt; and a straitjacket disposed around a perimeter of the atrial flange and configured to apply a hoop force to the expandable frame, thereby controlling an amount of expansion or an amount of collapse of the expandable frame, wherein the straitjacket comprises a first free end that comprises a slot and a second free end opposite the first free end, the second free end comprising an eyelet protruding outward and disposed in the slot, wherein, when a tether is releasably and slidably disposed in the eyelet, the straitjacket is held in a closed loop that constrains expansion of the atrial flange, and wherein removal of the tether from the eyelet allows the straitjacket to open and permit expansion of the atrial flange.

14. The prosthetic valve of claim 13, wherein the prosthetic valve is a prosthetic mitral valve.

15. The prosthetic valve of claim 13, wherein the plurality of commissure posts comprises a coupling element on the free end, the coupling element configured to releasably engage the prosthetic valve with a delivery catheter.

16. The prosthetic valve of claim 13, wherein at least one of the plurality of commissure posts are transverse to a longitudinal axis of the radially expandable frame.

17. The prosthetic valve of claim 13, wherein at least one of the plurality of commissure posts is adjustably angulatable relative to a longitudinal axis of the radially expandable frame.

18. The prosthetic valve of claim 15, wherein at least one of the coupling elements is a radiopaque marker configured to allow an operator to visualize an anterior portion of the prosthetic valve with radiographic imaging.

* * * * *